(12) United States Patent
Vivek et al.

(10) Patent No.: US 12,431,238 B2
(45) Date of Patent: Sep. 30, 2025

(54) IDENTITY-BASED SECURE MEDICAL DEVICE COMMUNICATIONS

(71) Applicant: ICU Medical, Inc., San Clemente, CA (US)

(72) Inventors: S. Sree Vivek, Chennai (IN);
Hrishikesh Anil Dandekar, Pune (IN);
Mark C. Rohlwing, Mesa, AZ (US);
Chaitanya Mattur Srinivasamurthy, Lake Forest, IL (US)

(73) Assignee: ICU Medical, Inc., San Clemente, CA (US)

( * ) Notice: Subject to any disclaimer, the term of this patent is extended or adjusted under 35 U.S.C. 154(b) by 293 days.

(21) Appl. No.: 17/648,652

(22) Filed: Jan. 21, 2022

(65) Prior Publication Data

US 2022/0165404 A1    May 26, 2022

Related U.S. Application Data

(63) Continuation of application No. PCT/US2021/048262, filed on Aug. 30, 2021.
(Continued)

(30) Foreign Application Priority Data

Sep. 5, 2020   (IN) .............................. 202011038396

(51) Int. Cl.
| | |
|---|---|
| *G16H 40/20* | (2018.01) |
| *H04L 9/08* | (2006.01) |
| *H04L 9/32* | (2006.01) |

(52) U.S. Cl.
CPC ........... *G16H 40/20* (2018.01); *H04L 9/0869* (2013.01); *H04L 9/0894* (2013.01); *H04L 9/3263* (2013.01); *H04L 2209/88* (2013.01)

(58) Field of Classification Search
CPC ........ G16H 40/20; G16H 40/67; G16H 20/17; H04L 9/0869; H04L 9/0894;
(Continued)

(56) References Cited

U.S. PATENT DOCUMENTS

| | | |
|---|---|---|
| 4,024,864 A | 5/1977 | Davies et al. |
| 4,055,175 A | 10/1977 | Clemens et al. |

(Continued)

FOREIGN PATENT DOCUMENTS

| | | |
|---|---|---|
| AU | 2004226440 | 10/2004 |
| AU | 2004305087 | 7/2005 |

(Continued)

OTHER PUBLICATIONS

Ahn et al., "Towards Scalable Authentication in Health Services", Eleventh IEEE International Workshops on Enabling Technologies: Infrastructure for Collaborative Enterprises, Jun. 2002, pp. 83-88.

(Continued)

*Primary Examiner* — Abu S Sholeman
(74) *Attorney, Agent, or Firm* — Knobbe, Martens, Olson & Bear, LLP

(57) ABSTRACT

The present disclosure is directed to managing the operation of devices using identity-based cryptography. These techniques may include provisioning a master public key to each system that will communicate with a medical device using device-identifier specific cryptography. A master secret key is provisioned in a trusted processor of the medical device, and the medical device provisions its own device identifier-specific secret key using the master secret key. This setup facilitates several management features, including automatic initial configuration, signed logging, signed backup files, and secure binding of medication containers to the medical device.

13 Claims, 9 Drawing Sheets

Related U.S. Application Data

(60) Provisional application No. 63/108,141, filed on Oct. 30, 2020.

(58) Field of Classification Search
CPC ............... H04L 9/3263; H04L 2209/88; H04L 9/0861; H04L 9/3247
See application file for complete search history.

(56) References Cited

U.S. PATENT DOCUMENTS

| | | |
|---|---|---|
| 4,151,845 A | 5/1979 | Clemens |
| 4,213,454 A | 7/1980 | Shim |
| 4,240,438 A | 12/1980 | Updike et al. |
| 4,280,494 A | 7/1981 | Cosgrove et al. |
| 4,308,866 A | 1/1982 | Jeliffe |
| 4,370,983 A | 2/1983 | Lichtenstein et al. |
| 4,373,527 A | 2/1983 | Fischell |
| 4,392,849 A | 7/1983 | Petre et al. |
| 4,395,259 A | 7/1983 | Prestele et al. |
| 4,457,751 A | 7/1984 | Rodler |
| 4,464,170 A | 8/1984 | Clemens |
| 4,469,481 A | 9/1984 | Kobayashi |
| 4,475,901 A | 10/1984 | Kraegen et al. |
| 4,494,950 A | 1/1985 | Fischell |
| 4,498,843 A | 2/1985 | Schneider et al. |
| 4,515,584 A | 5/1985 | Abe et al. |
| 4,526,568 A | 7/1985 | Clemens et al. |
| 4,529,401 A | 7/1985 | Leslie et al. |
| 4,543,955 A | 10/1985 | Schroeppel |
| 4,551,133 A | 11/1985 | Zegers de Beyl et al. |
| 4,553,958 A | 11/1985 | LeCocq |
| 4,559,037 A | 12/1985 | Franetzki et al. |
| 4,613,937 A | 9/1986 | Batty |
| 4,624,661 A | 11/1986 | Arimond |
| 4,633,878 A | 1/1987 | Bombardieri |
| 4,634,426 A | 1/1987 | Kamen |
| 4,634,427 A | 1/1987 | Hannula et al. |
| 4,674,652 A | 6/1987 | Aten et al. |
| 4,676,776 A | 6/1987 | Howson et al. |
| 4,679,562 A | 7/1987 | Luksha |
| 4,685,903 A | 8/1987 | Cable et al. |
| 4,695,954 A | 9/1987 | Rose |
| 4,696,671 A | 9/1987 | Epstein et al. |
| 4,714,462 A | 12/1987 | DiDomenico |
| 4,722,734 A | 2/1988 | Kolin |
| 4,730,849 A | 3/1988 | Siegel |
| 4,731,051 A | 3/1988 | Fischell |
| 4,741,732 A | 5/1988 | Crankshaw et al. |
| 4,756,706 A | 7/1988 | Kerns et al. |
| 4,776,842 A | 10/1988 | Franetzki et al. |
| 4,785,969 A | 11/1988 | McLaughlin |
| 4,803,625 A | 2/1989 | Fu et al. |
| 4,835,372 A | 5/1989 | Gombrich et al. |
| 4,838,275 A | 6/1989 | Lee |
| 4,838,856 A | 6/1989 | Mulreany et al. |
| 4,838,857 A | 6/1989 | Strowe et al. |
| 4,854,324 A | 8/1989 | Hirschman et al. |
| 4,857,716 A | 8/1989 | Gombrich et al. |
| 4,858,154 A | 8/1989 | Anderson et al. |
| 4,898,578 A | 2/1990 | Rubalcaba, Jr. |
| 4,908,017 A | 3/1990 | Howson et al. |
| 4,933,873 A | 6/1990 | Kaufman et al. |
| 4,943,279 A | 7/1990 | Samiotes et al. |
| 4,946,439 A | 8/1990 | Eggers |
| 4,953,745 A | 9/1990 | Rowlett |
| 4,978,335 A | 12/1990 | Arthur, III |
| 5,000,739 A | 3/1991 | Kulisz et al. |
| 5,010,473 A | 4/1991 | Jacobs |
| 5,014,698 A | 5/1991 | Cohen |
| 5,016,172 A | 5/1991 | Dessertine |
| 5,026,084 A | 6/1991 | Paisfield |
| 5,034,004 A | 7/1991 | Crankshaw |
| 5,041,086 A | 8/1991 | Koenig et al. |
| 5,058,161 A | 10/1991 | Weiss |
| 5,078,683 A | 1/1992 | Sancoff et al. |
| 5,084,828 A | 1/1992 | Kaufman et al. |
| 5,088,981 A | 2/1992 | Howson et al. |
| 5,097,505 A | 3/1992 | Weiss |
| 5,100,380 A | 3/1992 | Epstein et al. |
| 5,102,392 A | 4/1992 | Sakai et al. |
| 5,104,374 A | 4/1992 | Bishko et al. |
| 5,109,850 A | 5/1992 | Blanco et al. |
| 5,131,816 A | 7/1992 | Brown |
| 5,142,484 A | 8/1992 | Kaufman et al. |
| 5,153,827 A | 10/1992 | Coutre et al. |
| 5,157,640 A | 10/1992 | Backner |
| 5,161,222 A | 11/1992 | Montejo et al. |
| 5,177,993 A | 1/1993 | Beckman et al. |
| 5,181,910 A | 1/1993 | Scanlon |
| 5,190,522 A | 3/1993 | Wocicki et al. |
| 5,199,439 A | 4/1993 | Zimmerman et al. |
| 5,200,891 A | 4/1993 | Kehr et al. |
| 5,216,597 A | 6/1993 | Beckers |
| 5,221,268 A | 6/1993 | Barton et al. |
| 5,230,061 A | 7/1993 | Welch |
| 5,243,982 A | 9/1993 | Möstl et al. |
| 5,244,463 A | 9/1993 | Cordner, Jr. et al. |
| 5,249,260 A | 9/1993 | Nigawara et al. |
| 5,254,096 A | 10/1993 | Rondelet et al. |
| 5,256,156 A | 10/1993 | Kern et al. |
| 5,256,157 A | 10/1993 | Samiotes et al. |
| 5,261,702 A | 11/1993 | Mayfield |
| 5,317,506 A | 5/1994 | Coutre et al. |
| 5,319,355 A | 6/1994 | Russek |
| 5,319,363 A | 6/1994 | Welch et al. |
| 5,330,634 A | 7/1994 | Wong et al. |
| 5,338,157 A | 8/1994 | Blomquist |
| 5,341,476 A | 8/1994 | Lowell |
| 5,364,346 A | 11/1994 | Schrezenmeir |
| 5,366,346 A | 11/1994 | Danby |
| 5,368,562 A | 11/1994 | Blomquist et al. |
| 5,373,454 A | 12/1994 | Kanda et al. |
| 5,376,070 A | 12/1994 | Purvis et al. |
| 5,378,231 A | 1/1995 | Johnson et al. |
| 5,389,071 A | 2/1995 | Kawahara et al. |
| 5,389,078 A | 2/1995 | Zalesky et al. |
| 5,417,222 A | 5/1995 | Dempsey et al. |
| 5,423,748 A | 6/1995 | Uhala |
| 5,429,602 A | 7/1995 | Hauser |
| 5,431,627 A | 7/1995 | Pastrone et al. |
| 5,432,777 A | 7/1995 | Le Boudec et al. |
| 5,445,621 A | 8/1995 | Poli et al. |
| 5,447,164 A | 9/1995 | Shaya et al. |
| 5,455,851 A | 10/1995 | Chaco et al. |
| 5,461,365 A | 10/1995 | Schlager et al. |
| 5,464,392 A | 11/1995 | Epstein et al. |
| 5,465,082 A | 11/1995 | Chaco |
| 5,485,408 A | 1/1996 | Blomquist |
| 5,486,286 A | 1/1996 | Peterson et al. |
| 5,493,430 A | 2/1996 | Lu et al. |
| 5,496,273 A | 3/1996 | Pastrone et al. |
| 5,505,828 A | 4/1996 | Wong et al. |
| 5,507,288 A | 4/1996 | Bocker et al. |
| 5,507,786 A | 4/1996 | Morgan et al. |
| 5,508,499 A | 4/1996 | Ferrario |
| 5,515,713 A | 5/1996 | Saugues et al. |
| 5,520,637 A | 5/1996 | Pager et al. |
| 5,522,798 A | 6/1996 | Johnson et al. |
| 5,547,470 A | 8/1996 | Johnson et al. |
| 5,554,013 A | 9/1996 | Owens et al. |
| 5,562,615 A | 10/1996 | Nassif |
| 5,577,169 A | 11/1996 | Prezioso |
| 5,582,323 A | 12/1996 | Kurtenbach |
| 5,582,593 A | 12/1996 | Hultman |
| 5,594,786 A | 1/1997 | Chaco et al. |
| 5,598,519 A | 1/1997 | Narayanan |
| 5,620,608 A | 4/1997 | Rosa et al. |
| 5,630,710 A | 5/1997 | Tune et al. |
| 5,636,044 A | 6/1997 | Yuan et al. |
| 5,643,212 A | 7/1997 | Coutre et al. |
| 5,651,775 A | 7/1997 | Walker et al. |
| 5,658,131 A | 8/1997 | Aoki et al. |
| 5,658,250 A | 8/1997 | Blomquist et al. |
| 5,665,065 A | 9/1997 | Colman et al. |

(56) References Cited

U.S. PATENT DOCUMENTS

| | | |
|---|---|---|
| 5,669,877 A | 9/1997 | Blomquist |
| 5,672,154 A | 9/1997 | Sillén et al. |
| 5,681,285 A | 10/1997 | Ford et al. |
| 5,685,844 A | 11/1997 | Marttila |
| 5,687,717 A | 11/1997 | Halpern et al. |
| 5,689,229 A | 11/1997 | Chaco et al. |
| 5,697,899 A | 12/1997 | Hillman et al. |
| 5,699,509 A | 12/1997 | Gary et al. |
| 5,708,714 A | 1/1998 | Lopez et al. |
| 5,713,350 A | 2/1998 | Yokota et al. |
| 5,713,856 A | 2/1998 | Eggers et al. |
| 5,718,562 A | 2/1998 | Lawless et al. |
| 5,719,761 A | 2/1998 | Gatti et al. |
| 5,733,259 A | 3/1998 | Valcke et al. |
| 5,738,102 A | 4/1998 | Lemelson |
| 5,744,027 A | 4/1998 | Connell et al. |
| 5,752,621 A | 5/1998 | Passamante |
| 5,754,111 A | 5/1998 | Garcia |
| 5,764,034 A | 6/1998 | Bowman et al. |
| 5,764,159 A | 6/1998 | Neftel et al. |
| 5,772,635 A | 6/1998 | Dastur et al. |
| 5,774,865 A | 6/1998 | Glynn |
| 5,778,256 A | 7/1998 | Darbee |
| 5,778,345 A | 7/1998 | McCartney |
| 5,781,442 A | 7/1998 | Engleson et al. |
| 5,782,805 A | 7/1998 | Meinzer et al. |
| 5,788,669 A | 8/1998 | Peterson |
| 5,797,515 A | 8/1998 | Liff et al. |
| 5,800,387 A | 9/1998 | Duffy et al. |
| 5,814,015 A | 9/1998 | Gargano et al. |
| 5,822,544 A | 10/1998 | Chaco et al. |
| 5,822,715 A | 10/1998 | Worthington et al. |
| 5,827,179 A | 10/1998 | Lichter et al. |
| 5,832,448 A | 11/1998 | Brown |
| 5,836,910 A | 11/1998 | Duffy et al. |
| 5,850,344 A | 12/1998 | Conkright |
| 5,867,821 A | 2/1999 | Ballantyne et al. |
| 5,870,733 A | 2/1999 | Bass et al. |
| 5,871,465 A | 2/1999 | Vasko |
| 5,873,731 A | 2/1999 | Predergast |
| 5,885,245 A | 3/1999 | Lynch et al. |
| 5,897,493 A | 4/1999 | Brown |
| 5,897,498 A | 4/1999 | Canfield, II et al. |
| 5,910,252 A | 6/1999 | Truitt et al. |
| 5,912,818 A | 6/1999 | McGrady et al. |
| 5,915,240 A | 6/1999 | Karpf |
| 5,920,054 A | 7/1999 | Uber, III |
| 5,920,263 A | 7/1999 | Huttenhoff et al. |
| 5,924,074 A | 7/1999 | Evans |
| 5,931,764 A | 8/1999 | Freeman et al. |
| 5,935,099 A | 8/1999 | Peterson et al. |
| 5,935,106 A | 8/1999 | Olsen |
| 5,941,846 A | 8/1999 | Duffy et al. |
| 5,956,501 A | 9/1999 | Brown |
| 5,957,885 A | 9/1999 | Bollish et al. |
| 5,960,085 A | 9/1999 | de la Huerga |
| 5,961,448 A | 10/1999 | Swenson et al. |
| 5,967,559 A | 10/1999 | Abramowitz |
| 5,971,594 A | 10/1999 | Sahai et al. |
| 5,975,081 A | 11/1999 | Hood et al. |
| 5,990,838 A | 11/1999 | Burns et al. |
| 5,997,476 A | 12/1999 | Brown |
| 6,000,828 A | 12/1999 | Leet |
| 6,003,006 A | 12/1999 | Colella et al. |
| 6,012,034 A | 1/2000 | Hamparian et al. |
| 6,017,318 A | 1/2000 | Gauthier et al. |
| 6,021,392 A | 2/2000 | Lester et al. |
| 6,024,539 A | 2/2000 | Blomquist |
| 6,024,699 A | 2/2000 | Surwit et al. |
| 6,032,155 A | 2/2000 | de la Huerga |
| 6,032,676 A | 3/2000 | Moore |
| 6,039,251 A | 3/2000 | Holowko et al. |
| 6,070,761 A | 6/2000 | Bloom et al. |
| 6,073,106 A | 6/2000 | Rozen et al. |
| 6,104,295 A | 8/2000 | Gaisser et al. |
| 6,112,182 A | 8/2000 | Akers et al. |
| 6,112,323 A | 8/2000 | Meizlik et al. |
| RE36,871 E | 9/2000 | Epstein et al. |
| 6,115,365 A | 9/2000 | Newberg |
| 6,115,390 A | 9/2000 | Chuah |
| 6,122,536 A | 9/2000 | Sun et al. |
| 6,126,637 A | 10/2000 | Kriesel et al. |
| 6,135,949 A | 10/2000 | Russo et al. |
| 6,150,942 A | 11/2000 | O'Brien |
| 6,151,643 A | 11/2000 | Cheng et al. |
| 6,157,914 A | 12/2000 | Seto et al. |
| 6,159,147 A | 12/2000 | Lichter et al. |
| 6,167,567 A | 12/2000 | Chiles et al. |
| 6,182,667 B1 | 2/2001 | Hanks et al. |
| 6,189,105 B1 | 2/2001 | Lopes |
| 6,195,589 B1 | 2/2001 | Ketcham |
| 6,208,974 B1 | 3/2001 | Campbell et al. |
| 6,222,323 B1 | 4/2001 | Yamashita et al. |
| 6,223,440 B1 | 5/2001 | Rashman |
| 6,226,277 B1 | 5/2001 | Chuah |
| 6,227,371 B1 | 5/2001 | Song |
| 6,234,176 B1 | 5/2001 | Domae et al. |
| 6,241,704 B1 | 6/2001 | Peterson et al. |
| 6,248,067 B1 | 6/2001 | Causey, III et al. |
| 6,249,705 B1 | 6/2001 | Snell |
| 6,257,265 B1 | 7/2001 | Brunner et al. |
| 6,259,355 B1 | 7/2001 | Chaco et al. |
| 6,269,340 B1 | 7/2001 | Ford et al. |
| 6,270,455 B1 | 8/2001 | Brown |
| 6,271,813 B1 | 8/2001 | Palalau |
| 6,277,072 B1 | 8/2001 | Bardy |
| 6,280,380 B1 | 8/2001 | Bardy |
| 6,283,761 B1 | 9/2001 | Joao |
| 6,285,665 B1 | 9/2001 | Chuah |
| 6,292,860 B1 | 9/2001 | Cochcroft, Jr. |
| 6,312,378 B1 | 11/2001 | Bardy |
| 6,327,254 B1 | 12/2001 | Chuah |
| 6,330,008 B1 | 12/2001 | Razdow et al. |
| 6,339,718 B1 | 1/2002 | Zatezalo et al. |
| 6,346,886 B1 | 2/2002 | de la Huerga |
| 6,363,282 B1 | 3/2002 | Nichols et al. |
| 6,371,719 B1 | 4/2002 | Hildebrandt |
| 6,377,548 B1 | 4/2002 | Chuah |
| 6,388,951 B1 | 5/2002 | Matsumoto et al. |
| 6,406,426 B1 | 6/2002 | Reuss et al. |
| 6,408,330 B1 | 6/2002 | de la Huerga |
| 6,418,334 B1 | 7/2002 | Unger et al. |
| 6,427,088 B1 | 7/2002 | Bowman et al. |
| 6,428,483 B1 | 8/2002 | Carlebach |
| 6,442,432 B2 | 8/2002 | Lee |
| 6,469,991 B1 | 10/2002 | Chuah |
| 6,475,180 B2 | 11/2002 | Peterson et al. |
| 6,482,158 B2 | 11/2002 | Mault |
| 6,485,418 B2 | 11/2002 | Yasushi et al. |
| 6,494,694 B2 | 12/2002 | Lawless et al. |
| 6,494,831 B1 | 12/2002 | Koritzinsky |
| 6,497,680 B1 | 12/2002 | Holst et al. |
| 6,514,460 B1 | 2/2003 | Fendrock |
| 6,517,482 B1 | 2/2003 | Eiden et al. |
| 6,519,569 B1 | 2/2003 | White et al. |
| 6,520,930 B2 | 2/2003 | Critchlow et al. |
| 6,540,672 B1 | 4/2003 | Simonsen et al. |
| 6,542,902 B2 | 4/2003 | Dulong et al. |
| 6,544,212 B2 | 4/2003 | Galley et al. |
| 6,544,228 B1 | 4/2003 | Heitmeier |
| 6,546,350 B1 | 4/2003 | Hartmann et al. |
| 6,551,276 B1 | 4/2003 | Mann et al. |
| 6,554,798 B1 | 4/2003 | Mann et al. |
| 6,558,320 B1 | 5/2003 | Causey et al. |
| 6,558,351 B1 | 5/2003 | Steil et al. |
| 6,565,509 B1 | 5/2003 | Say et al. |
| 6,567,416 B1 | 5/2003 | Chuah |
| 6,571,294 B2 | 5/2003 | Simmon et al. |
| 6,572,542 B1 | 6/2003 | Houben et al. |
| 6,572,545 B2 | 6/2003 | Knobbe et al. |
| 6,578,002 B1 | 6/2003 | Derzay et al. |
| 6,581,117 B1 | 6/2003 | Klein et al. |
| 6,587,034 B1 | 7/2003 | Heiman et al. |
| 6,589,229 B1 | 7/2003 | Connelly et al. |

(56) References Cited

U.S. PATENT DOCUMENTS

| | | |
|---|---|---|
| 6,599,281 B1 | 7/2003 | Struys et al. |
| 6,602,191 B2 | 8/2003 | Quy |
| 6,605,072 B2 | 8/2003 | Struys et al. |
| 6,628,809 B1 | 9/2003 | Rowe et al. |
| 6,631,353 B1 | 10/2003 | Davis et al. |
| 6,640,246 B1 | 10/2003 | Gardy, Jr. et al. |
| 6,641,533 B2 | 11/2003 | Causey, III et al. |
| 6,647,299 B2 | 11/2003 | Bourget |
| 6,652,455 B1 | 11/2003 | Kocher |
| 6,653,937 B2 | 11/2003 | Nelson et al. |
| 6,659,947 B1 | 12/2003 | Carter et al. |
| 6,669,630 B1 | 12/2003 | Joliat et al. |
| 6,671,563 B1 | 12/2003 | Engleson et al. |
| 6,673,033 B1 | 1/2004 | Sciulli et al. |
| 6,674,403 B2 | 1/2004 | Gray et al. |
| 6,681,003 B2 | 1/2004 | Linder et al. |
| 6,689,091 B2 | 2/2004 | Bui et al. |
| 6,692,241 B2 | 2/2004 | Watanabe et al. |
| 6,694,191 B2 | 2/2004 | Starkweather et al. |
| 6,694,334 B2 | 2/2004 | DuLong et al. |
| 6,721,286 B1 | 4/2004 | Williams et al. |
| 6,721,582 B2 | 4/2004 | Trepagnier et al. |
| 6,725,200 B1 | 4/2004 | Rost |
| 6,731,989 B2 | 5/2004 | Engleson et al. |
| 6,740,072 B2 | 5/2004 | Starkweather et al. |
| 6,751,651 B2 | 6/2004 | Crockett |
| 6,752,787 B1 | 6/2004 | Causey, III et al. |
| 6,753,830 B2 | 6/2004 | Gelbman |
| 6,758,810 B2 | 7/2004 | Lebel et al. |
| 6,773,396 B2 | 8/2004 | Flach et al. |
| 6,774,786 B1 | 8/2004 | Havekost et al. |
| 6,775,577 B2 | 8/2004 | Crnkovich et al. |
| 6,780,156 B2 | 8/2004 | Haueter et al. |
| 6,790,198 B1 | 9/2004 | White et al. |
| 6,792,470 B2 | 9/2004 | Hakenberg et al. |
| 6,796,956 B2 | 9/2004 | Hartlaub et al. |
| 6,799,149 B2 | 9/2004 | Hartlaub |
| 6,809,653 B1 | 10/2004 | Mann et al. |
| 6,811,534 B2 | 11/2004 | Bowman, IV et al. |
| 6,816,605 B2 | 11/2004 | Rowe et al. |
| 6,839,753 B2 | 1/2005 | Biondi et al. |
| 6,852,104 B2 | 2/2005 | Blomquist |
| 6,859,134 B1 | 2/2005 | Heiman et al. |
| 6,871,211 B2 | 3/2005 | Labounty et al. |
| 6,873,268 B2 | 3/2005 | Lebel et al. |
| 6,876,303 B2 | 4/2005 | Reeder et al. |
| 6,885,881 B2 | 4/2005 | Leonhardt |
| 6,891,525 B2 | 5/2005 | Ogoro |
| 6,892,278 B2 | 5/2005 | Ebergen |
| 6,899,695 B2 | 5/2005 | Herrera |
| 6,915,170 B2 | 7/2005 | Engleson et al. |
| 6,923,763 B1 | 8/2005 | Kovatchev et al. |
| 6,924,781 B1 | 8/2005 | Gelbman |
| 6,928,338 B1 | 8/2005 | Buchser et al. |
| 6,928,490 B1 | 8/2005 | Bucholz et al. |
| 6,936,029 B2 | 8/2005 | Mann et al. |
| 6,945,954 B2 | 9/2005 | Hochman et al. |
| 6,948,492 B2 | 9/2005 | Wermeling et al. |
| 6,958,677 B1 | 10/2005 | Carter |
| 6,958,691 B1 | 10/2005 | Anderson et al. |
| 6,958,705 B2 | 10/2005 | Lebel et al. |
| 6,961,448 B2 | 11/2005 | Nichols et al. |
| 6,969,352 B2 | 11/2005 | Chiang et al. |
| 6,969,865 B2 | 11/2005 | Duchon et al. |
| 6,974,437 B2 | 12/2005 | Lebel et al. |
| 6,979,326 B2 | 12/2005 | Mann et al. |
| 6,980,958 B1 | 12/2005 | Surwit et al. |
| 6,985,870 B2 | 1/2006 | Martucci et al. |
| 6,986,347 B2 | 1/2006 | Hickle |
| 6,997,880 B2 | 2/2006 | Carlebach et al. |
| 6,997,920 B2 | 2/2006 | Mann et al. |
| 6,998,984 B1 | 2/2006 | Zittrain |
| 7,016,752 B1 | 3/2006 | Ruben et al. |
| 7,017,293 B2 | 3/2006 | Riley |
| 7,025,743 B2 | 4/2006 | Mann et al. |
| 7,029,455 B2 | 4/2006 | Flaherty |
| 7,038,584 B2 | 5/2006 | Carter |
| 7,060,031 B2 | 6/2006 | Webb et al. |
| 7,060,059 B2 | 6/2006 | Keith et al. |
| 7,069,552 B2 | 6/2006 | Lindberg et al. |
| 7,072,725 B2 | 7/2006 | Bristol et al. |
| 7,079,035 B2 | 7/2006 | Bock et al. |
| 7,092,943 B2 | 8/2006 | Roese et al. |
| 7,096,072 B2 | 8/2006 | Engleson et al. |
| 7,099,809 B2 | 8/2006 | Dori |
| 7,103,419 B2 | 9/2006 | Engleson et al. |
| 7,103,578 B2 | 9/2006 | Beck et al. |
| 7,107,106 B2 | 9/2006 | Engleson et al. |
| 7,108,680 B2 | 9/2006 | Rohr et al. |
| 7,109,878 B2 | 9/2006 | Mann et al. |
| 7,114,002 B1 | 9/2006 | Okumura et al. |
| 7,117,041 B2 | 10/2006 | Engleson et al. |
| 7,136,645 B2 | 11/2006 | Hanson et al. |
| 7,137,964 B2 | 11/2006 | Flaherty |
| 7,142,190 B2 | 11/2006 | Martinez |
| 7,150,741 B2 | 12/2006 | Erickson et al. |
| 7,153,289 B2 | 12/2006 | Vasko |
| 7,154,397 B2 | 12/2006 | Zerhusen et al. |
| 7,156,807 B2 | 1/2007 | Carter et al. |
| 7,158,030 B2 | 1/2007 | Chung |
| 7,161,484 B2 | 1/2007 | Tsoukalis et al. |
| 7,167,755 B2 | 1/2007 | Seeberger et al. |
| 7,167,920 B2 | 1/2007 | Traversat |
| 7,171,277 B2 | 1/2007 | Engleson et al. |
| 7,171,492 B1 | 1/2007 | Borella et al. |
| 7,181,493 B2 | 2/2007 | English et al. |
| 7,185,288 B2 | 2/2007 | McKeever |
| 7,193,514 B2 | 3/2007 | Ritson |
| 7,197,025 B2 | 3/2007 | Chuah |
| 7,201,734 B2 | 4/2007 | Hickle |
| 7,204,823 B2 | 4/2007 | Estes et al. |
| 7,213,009 B2 | 5/2007 | Pestotnik |
| 7,216,802 B1 | 5/2007 | de la Huerga |
| 7,220,240 B2 | 5/2007 | Struys et al. |
| 7,224,979 B2 | 5/2007 | Singhal et al. |
| 7,229,430 B2 | 6/2007 | Hickle et al. |
| 7,230,529 B2 | 6/2007 | Ketcherside |
| 7,236,936 B2 | 6/2007 | White et al. |
| 7,238,164 B2 | 7/2007 | Childers et al. |
| 7,247,154 B2 | 7/2007 | Hickle |
| 7,248,239 B2 | 7/2007 | Dowling |
| 7,250,856 B2 | 7/2007 | Havekost et al. |
| 7,255,683 B2 | 8/2007 | Vanderveen et al. |
| 7,256,888 B2 | 8/2007 | Staehr et al. |
| 7,258,534 B2 | 8/2007 | Fathallah et al. |
| 7,263,213 B2 | 8/2007 | Rowe |
| 7,267,664 B2 | 9/2007 | Rizzo |
| 7,267,665 B2 | 9/2007 | Steil et al. |
| 7,275,156 B2 | 9/2007 | Balfanz et al. |
| 7,278,983 B2 | 10/2007 | Ireland et al. |
| 7,289,815 B2 | 10/2007 | Gfeller et al. |
| 7,289,948 B1 | 10/2007 | Mohri |
| 7,293,107 B1 | 11/2007 | Hanson et al. |
| 7,295,119 B2 | 11/2007 | Rappaport et al. |
| 7,295,556 B2 | 11/2007 | Roese et al. |
| 7,301,451 B2 | 11/2007 | Hastings |
| 7,308,300 B2 | 12/2007 | Toews et al. |
| 7,315,825 B2 | 1/2008 | Rosenfeld et al. |
| 7,319,386 B2 | 1/2008 | Collins, Jr. et al. |
| 7,324,000 B2 | 1/2008 | Zittrain et al. |
| 7,327,705 B2 | 2/2008 | Fletcher et al. |
| 7,343,224 B2 | 3/2008 | DiGianfilippo et al. |
| 7,346,025 B2 | 3/2008 | Bryson |
| 7,347,836 B2 | 3/2008 | Peterson et al. |
| 7,354,420 B2 | 4/2008 | Steil et al. |
| 7,369,897 B2 | 5/2008 | Boveja et al. |
| 7,369,948 B1 | 5/2008 | Ferenczi et al. |
| 7,383,088 B2 | 6/2008 | Spinelli et al. |
| 7,384,410 B2 | 6/2008 | Eggers et al. |
| 7,398,183 B2 | 7/2008 | Holland et al. |
| 7,398,279 B2 | 7/2008 | Muno, Jr. et al. |
| 7,399,277 B2 | 7/2008 | Saidara et al. |
| 7,402,153 B2 | 7/2008 | Steil et al. |
| 7,420,472 B2 | 9/2008 | Tran |

(56) References Cited

U.S. PATENT DOCUMENTS

| | | |
|---|---|---|
| 7,432,807 B2 | 10/2008 | Schmitt |
| 7,436,454 B2 | 10/2008 | Yamaguchi et al. |
| 7,447,643 B1 | 11/2008 | Olson |
| 7,454,314 B2 | 11/2008 | Holland et al. |
| 7,457,804 B2 | 11/2008 | Uber, III et al. |
| 7,464,040 B2 | 12/2008 | Joao |
| 7,469,213 B1 | 12/2008 | Rao |
| 7,471,994 B2 | 12/2008 | Ford et al. |
| 7,483,756 B2 | 1/2009 | Engleson et al. |
| 7,489,808 B2 | 2/2009 | Gerder |
| 7,490,021 B2 | 2/2009 | Holland et al. |
| 7,490,048 B2 | 2/2009 | Joao |
| 7,491,187 B2 | 2/2009 | Van Den Berghe et al. |
| 7,519,905 B2 | 4/2009 | Kougiouris et al. |
| 7,523,401 B1 | 4/2009 | Aldridge |
| 7,524,304 B2 | 4/2009 | Genosar |
| 7,551,078 B2 | 6/2009 | Carlson |
| 7,559,321 B2 | 7/2009 | Wermeling et al. |
| 7,565,197 B2 | 7/2009 | Haulbrich et al. |
| 7,572,230 B2 | 8/2009 | Neumann et al. |
| 7,578,802 B2 | 8/2009 | Hickle |
| 7,621,009 B2 | 11/2009 | Elhabashy |
| D606,533 S | 12/2009 | de Jong et al. |
| 7,636,718 B1 | 12/2009 | Steen et al. |
| 7,640,172 B2 | 12/2009 | Kuth |
| 7,645,258 B2 | 1/2010 | White et al. |
| 7,647,237 B2 | 1/2010 | Malave et al. |
| 7,662,124 B2 | 2/2010 | Duchon et al. |
| 7,668,731 B2 | 2/2010 | Martucci et al. |
| 7,671,733 B2 | 3/2010 | McNeal et al. |
| 7,678,071 B2 | 3/2010 | Lebel et al. |
| 7,687,678 B2 | 3/2010 | Jacobs |
| 7,697,994 B2 | 4/2010 | VanDanacker et al. |
| 7,698,239 B2 | 4/2010 | Lieuallen |
| 7,705,727 B2 | 4/2010 | Pestotnik |
| 7,724,147 B2 | 5/2010 | Brown et al. |
| 7,739,126 B1 | 6/2010 | Cave |
| 7,746,218 B2 | 6/2010 | Collins, Jr. |
| 7,766,873 B2 | 8/2010 | Moberg et al. |
| 7,776,029 B2 | 8/2010 | Whitehurst et al. |
| 7,776,031 B2 | 8/2010 | Hartlaub et al. |
| 7,785,313 B2 | 8/2010 | Mastrototaro |
| 7,788,369 B2 | 8/2010 | McAllen et al. |
| 7,806,852 B1 | 10/2010 | Jurson |
| 7,806,886 B2 | 10/2010 | Kanderian, Jr. et al. |
| 7,826,981 B2 | 11/2010 | Goode, Jr. et al. |
| 7,835,927 B2 | 11/2010 | Schlotterbeck et al. |
| 7,836,314 B2 | 11/2010 | Chieu |
| 7,856,276 B2 | 12/2010 | Ripart et al. |
| 7,860,583 B2 | 12/2010 | Condurso et al. |
| 7,864,771 B2 | 1/2011 | Tavares et al. |
| 7,868,754 B2 | 1/2011 | Salvat, Jr. |
| 7,871,394 B2 | 1/2011 | Halbert et al. |
| 7,886,231 B2 | 2/2011 | Hopermann et al. |
| 7,895,053 B2 | 2/2011 | Holland et al. |
| 7,896,842 B2 | 3/2011 | Palmroos et al. |
| 7,899,546 B2 | 3/2011 | Sieracki et al. |
| 7,905,710 B2 | 3/2011 | Wang et al. |
| 7,920,061 B2 | 4/2011 | Klein et al. |
| 7,933,780 B2 | 4/2011 | de la Huerga |
| 7,938,796 B2 | 5/2011 | Moubayed |
| 7,945,452 B2 | 5/2011 | Fathallah et al. |
| 7,974,714 B2 | 7/2011 | Hoffberg |
| 7,976,508 B2 | 7/2011 | Hoag |
| 7,996,241 B2 | 8/2011 | Zak |
| 8,034,026 B2 | 10/2011 | Grant |
| 8,038,593 B2 | 10/2011 | Friedman et al. |
| 8,048,040 B2 | 11/2011 | Kiani |
| 8,060,576 B2 | 11/2011 | Chan et al. |
| 8,065,161 B2 | 11/2011 | Howard et al. |
| 8,066,672 B2 | 11/2011 | Mandro |
| 8,075,514 B2 | 12/2011 | Butterfield et al. |
| 8,078,983 B2 | 12/2011 | Davis et al. |
| 8,082,018 B2 | 12/2011 | Duchon et al. |
| 8,082,312 B2 | 12/2011 | Chan et al. |
| 8,095,692 B2 | 1/2012 | Mehta et al. |
| 8,126,730 B2 | 2/2012 | Dicks et al. |
| 8,147,448 B2 | 4/2012 | Sundar et al. |
| 8,149,131 B2 | 4/2012 | Blomquist |
| 8,169,914 B2 | 5/2012 | Bajpai |
| 8,171,094 B2 | 5/2012 | Chan et al. |
| 8,172,798 B2 | 5/2012 | Hungerford et al. |
| 8,185,322 B2 | 5/2012 | Schroeder et al. |
| 8,195,478 B2 | 6/2012 | Petersen et al. |
| 8,206,350 B2 | 6/2012 | Mann et al. |
| 8,219,413 B2 | 7/2012 | Martinez et al. |
| 8,231,578 B2 | 7/2012 | Fathallah et al. |
| 8,234,128 B2 | 7/2012 | Martucci et al. |
| 8,267,892 B2 | 9/2012 | Spencer et al. |
| 8,271,106 B2 | 9/2012 | Wehba et al. |
| 8,287,495 B2 | 10/2012 | Michaud et al. |
| 8,291,337 B2 | 10/2012 | Gannin et al. |
| 8,298,184 B2 | 10/2012 | DiPerna et al. |
| 8,312,272 B1 | 11/2012 | Serenyl et al. |
| 8,352,290 B2 | 1/2013 | Bartz et al. |
| 8,359,338 B2 | 1/2013 | Butterfield et al. |
| 8,380,536 B2 | 2/2013 | Howard et al. |
| 8,387,112 B1 | 2/2013 | Ranjan et al. |
| 8,394,077 B2 | 3/2013 | Jacobson et al. |
| 8,398,592 B2 | 3/2013 | Leibner-Druska |
| 8,403,908 B2 | 3/2013 | Jacobson et al. |
| 8,435,206 B2 | 5/2013 | Evans et al. |
| 8,449,523 B2 | 5/2013 | Brukalo et al. |
| 8,452,953 B2 | 5/2013 | Buck et al. |
| 8,453,645 B2 | 6/2013 | Figueiredo et al. |
| 8,472,630 B2 | 6/2013 | Konrad et al. |
| 8,480,648 B2 | 7/2013 | Burnett et al. |
| 8,486,019 B2 | 7/2013 | White et al. |
| 8,489,427 B2 | 7/2013 | Simpson et al. |
| 8,494,879 B2 | 7/2013 | Davis et al. |
| 8,504,179 B2 | 8/2013 | Blomquist |
| 8,517,990 B2 | 8/2013 | Teel et al. |
| 8,518,021 B2 | 8/2013 | Stewart et al. |
| 8,543,416 B2 | 9/2013 | Palmroos et al. |
| 8,551,038 B2 | 10/2013 | Tsoukalis et al. |
| 8,560,345 B2 | 10/2013 | Wehba et al. |
| 8,567,681 B2 | 10/2013 | Borges et al. |
| 8,577,692 B2 | 11/2013 | Silkaitis et al. |
| 8,579,884 B2 | 11/2013 | Lanier et al. |
| 8,626,530 B1 | 1/2014 | Tran et al. |
| 8,655,676 B2 | 2/2014 | Wehba et al. |
| 8,660,860 B2 | 2/2014 | Wehba et al. |
| 8,662,388 B2 | 3/2014 | Belkin |
| 8,666,769 B2 | 3/2014 | Butler et al. |
| 8,667,293 B2 | 3/2014 | Birtwhistle et al. |
| 8,687,811 B2 | 4/2014 | Nierzwick et al. |
| 8,700,421 B2 | 4/2014 | Feng et al. |
| 8,731,960 B2 | 5/2014 | Butler et al. |
| 8,768,719 B2 | 7/2014 | Wehba et al. |
| 8,771,251 B2 | 7/2014 | Ruchti et al. |
| 8,777,894 B2 | 7/2014 | Butterfield et al. |
| 8,777,895 B2 | 7/2014 | Hsu et al. |
| 8,799,012 B2 | 8/2014 | Butler et al. |
| 8,876,793 B2 | 11/2014 | Ledford et al. |
| 8,886,316 B1 | 11/2014 | Juels |
| 8,922,330 B2 | 12/2014 | Moberg et al. |
| 8,936,565 B2 | 1/2015 | Chawla |
| 8,945,043 B2 | 2/2015 | Lee et al. |
| 8,952,794 B2 | 2/2015 | Blomquist et al. |
| 8,959,617 B2 | 2/2015 | Newlin et al. |
| 8,998,100 B2 | 4/2015 | Halbert et al. |
| 9,026,370 B2 | 5/2015 | Rubalcaba et al. |
| 9,069,887 B2 | 6/2015 | Gupta et al. |
| 9,077,544 B2 | 7/2015 | Baker et al. |
| 9,089,642 B2 | 7/2015 | Murphy et al. |
| 9,114,217 B2 | 8/2015 | Sur et al. |
| 9,123,077 B2 | 9/2015 | Silkaitis et al. |
| 9,192,712 B2 | 11/2015 | DeBelser et al. |
| 9,240,002 B2 | 1/2016 | Hume et al. |
| 9,292,692 B2 | 3/2016 | Wallrabenstein |
| 9,302,035 B2 | 4/2016 | Marseille et al. |
| 9,313,154 B1 | 4/2016 | Son |
| 9,381,296 B2 | 7/2016 | Arrizza et al. |
| 9,393,362 B2 | 7/2016 | Cozmi et al. |

(56) References Cited

U.S. PATENT DOCUMENTS

| | | | |
|---|---|---|---|
| 9,430,655 B1 | 8/2016 | Stockton et al. | |
| 9,438,580 B2 | 9/2016 | Kupper | |
| 9,483,615 B2 | 11/2016 | Roberts | |
| 9,498,583 B2 | 11/2016 | Sur et al. | |
| 9,539,383 B2 | 1/2017 | Kohlbrecher | |
| 9,572,923 B2 | 2/2017 | Howard et al. | |
| 9,594,875 B2 | 3/2017 | Arrizza et al. | |
| 9,604,000 B2 | 3/2017 | Wehba et al. | |
| 9,641,432 B2 | 5/2017 | Jha et al. | |
| 9,649,431 B2 | 5/2017 | Gray et al. | |
| 9,662,436 B2 | 5/2017 | Belkin et al. | |
| 9,690,909 B2 | 6/2017 | Stewart et al. | |
| 9,707,341 B2 | 7/2017 | Dumas, III et al. | |
| 9,717,845 B2 | 8/2017 | Istoc | |
| 9,724,470 B2 | 8/2017 | Day et al. | |
| 9,764,082 B2 | 9/2017 | Day et al. | |
| 9,886,550 B2 | 2/2018 | Lee et al. | |
| 9,943,269 B2 | 4/2018 | Muhsin et al. | |
| 9,967,739 B2 | 5/2018 | Proennecke et al. | |
| 9,971,871 B2 | 5/2018 | Arrizza et al. | |
| 9,995,611 B2 | 6/2018 | Ruchti et al. | |
| 10,022,498 B2 | 7/2018 | Ruchti et al. | |
| 10,042,986 B2 | 8/2018 | Ruchti et al. | |
| 10,046,112 B2 | 8/2018 | Oruklu et al. | |
| 10,097,353 B1* | 10/2018 | Carlson | H04L 67/306 |
| 10,166,328 B2 | 1/2019 | Oruklu et al. | |
| 10,173,008 B2 | 1/2019 | Simpson et al. | |
| 10,188,849 B2 | 1/2019 | Fangrow | |
| 10,233,179 B2 | 3/2019 | Ng et al. | |
| 10,238,799 B2 | 3/2019 | Kohlbrecher | |
| 10,238,801 B2 | 3/2019 | Wehba et al. | |
| 10,242,060 B2 | 3/2019 | Butler et al. | |
| 10,300,194 B2 | 5/2019 | Day et al. | |
| 10,311,972 B2 | 6/2019 | Kohlbrecher et al. | |
| 10,314,974 B2 | 6/2019 | Day et al. | |
| 10,333,843 B2 | 6/2019 | Jha et al. | |
| 10,341,866 B1 | 7/2019 | Spencer et al. | |
| 10,409,995 B1 | 9/2019 | Wasiq | |
| 10,430,761 B2 | 10/2019 | Hume et al. | |
| 10,434,246 B2 | 10/2019 | Silkaitis et al. | |
| 10,438,001 B1 | 10/2019 | Hariprasad | |
| 10,452,842 B2 | 10/2019 | Dhondse | |
| 10,453,157 B2 | 10/2019 | Kamen et al. | |
| 10,463,788 B2 | 11/2019 | Day | |
| 10,516,536 B2 | 12/2019 | Rommel | |
| 10,617,815 B2 | 4/2020 | Day et al. | |
| 10,646,651 B2 | 5/2020 | Day et al. | |
| 10,681,207 B1 | 6/2020 | Johnson et al. | |
| 10,692,595 B2 | 6/2020 | Xavier et al. | |
| 10,728,262 B1 | 7/2020 | Vaswani | |
| 10,740,436 B2 | 8/2020 | Moskal et al. | |
| 10,741,280 B2 | 8/2020 | Xavier et al. | |
| 10,757,219 B2 | 8/2020 | Moskal | |
| 10,765,799 B2 | 9/2020 | Belkin et al. | |
| 10,799,632 B2 | 10/2020 | Kohlbrecher | |
| 10,812,380 B2 | 10/2020 | Jha et al. | |
| 10,861,592 B2 | 12/2020 | Xavier et al. | |
| 10,898,641 B2 | 1/2021 | Day et al. | |
| 10,950,339 B2 | 3/2021 | Xavier et al. | |
| 10,964,428 B2 | 3/2021 | Xavier et al. | |
| 11,013,861 B2 | 5/2021 | Wehba et al. | |
| 11,037,668 B2 | 6/2021 | Ruchti et al. | |
| 11,052,193 B2 | 7/2021 | Day et al. | |
| 11,139,058 B2 | 10/2021 | Xavier et al. | |
| 11,151,290 B2 | 10/2021 | Karakoyunlu et al. | |
| 11,152,108 B2 | 10/2021 | Xavier et al. | |
| 11,152,109 B2 | 10/2021 | Xavier et al. | |
| 11,152,110 B2 | 10/2021 | Xavier et al. | |
| 11,194,810 B2 | 12/2021 | Butler et al. | |
| 11,235,100 B2 | 2/2022 | Howard et al. | |
| 11,289,183 B2 | 3/2022 | Kohlbrecher | |
| 11,309,070 B2 | 4/2022 | Xavier et al. | |
| 11,328,804 B2 | 5/2022 | Xavier et al. | |
| 11,328,805 B2 | 5/2022 | Xavier et al. | |
| 11,373,753 B2 | 6/2022 | Xavier et al. | |
| 11,437,132 B2 | 9/2022 | Xavier et al. | |
| 11,470,000 B2 | 10/2022 | Jha et al. | |
| 11,483,402 B2 | 10/2022 | Xavier et al. | |
| 11,483,403 B2 | 10/2022 | Xavier et al. | |
| 11,501,877 B2 | 11/2022 | Kohlbrecher et al. | |
| 11,571,508 B2 | 2/2023 | Jacobson et al. | |
| 11,574,721 B2 | 2/2023 | Kohlbrecher | |
| 11,574,737 B2 | 2/2023 | Dharwad et al. | |
| 11,587,669 B2 | 2/2023 | Xavier et al. | |
| 11,590,057 B2 | 2/2023 | Tagliamento et al. | |
| 11,594,326 B2 | 2/2023 | Xavier et al. | |
| 11,605,468 B2 | 3/2023 | Jacobson et al. | |
| 11,626,205 B2 | 4/2023 | Arrizza et al. | |
| 11,628,246 B2 | 4/2023 | Day et al. | |
| 11,628,254 B2 | 4/2023 | Day et al. | |
| 11,654,237 B2 | 5/2023 | Wehba et al. | |
| 11,670,416 B2 | 6/2023 | Xavier et al. | |
| 11,763,927 B2 | 9/2023 | Ruchti et al. | |
| 11,783,935 B2 | 10/2023 | Xavier et al. | |
| 11,881,297 B2 | 1/2024 | Xavier et al. | |
| 11,923,076 B2 | 3/2024 | Xavier et al. | |
| 11,986,623 B2 | 5/2024 | Jacobson et al. | |
| 11,996,188 B2 | 5/2024 | Arrizza et al. | |
| 12,002,562 B2 | 6/2024 | Kohlbrecher | |
| 12,036,390 B2 | 7/2024 | Wehba et al. | |
| 12,040,068 B2 | 7/2024 | Xavier et al. | |
| 12,042,623 B2 | 7/2024 | Day et al. | |
| 12,042,631 B2 | 7/2024 | Day et al. | |
| 12,046,361 B2 | 7/2024 | Xavier et al. | |
| 12,047,292 B2 | 7/2024 | Jha et al. | |
| 12,205,699 B1* | 1/2025 | Kim | G16H 40/67 |
| 2001/0016056 A1 | 8/2001 | Westphal et al. | |
| 2001/0029178 A1 | 10/2001 | Criss et al. | |
| 2001/0031944 A1 | 10/2001 | Peterson et al. | |
| 2001/0032099 A1 | 10/2001 | Joao | |
| 2001/0037060 A1 | 11/2001 | Thompson et al. | |
| 2001/0044731 A1 | 11/2001 | Coffman et al. | |
| 2001/0048027 A1 | 12/2001 | Walsh | |
| 2001/0051787 A1 | 12/2001 | Haller et al. | |
| 2001/0056358 A1 | 12/2001 | Dulong et al. | |
| 2002/0010595 A1 | 1/2002 | Kapp | |
| 2002/0013551 A1 | 1/2002 | Zaitsu et al. | |
| 2002/0013723 A1 | 1/2002 | Mise | |
| 2002/0015018 A1 | 2/2002 | Shimazu et al. | |
| 2002/0019584 A1 | 2/2002 | Schulze et al. | |
| 2002/0021700 A1 | 2/2002 | Hata et al. | |
| 2002/0026103 A1 | 2/2002 | Norris et al. | |
| 2002/0029776 A1 | 3/2002 | Blomquist | |
| 2002/0032583 A1 | 3/2002 | Joao | |
| 2002/0040208 A1 | 4/2002 | Flaherty et al. | |
| 2002/0040282 A1 | 4/2002 | Bailey et al. | |
| 2002/0044043 A1 | 4/2002 | Chaco et al. | |
| 2002/0044059 A1 | 4/2002 | Reeder et al. | |
| 2002/0082728 A1 | 6/2002 | Mueller et al. | |
| 2002/0087115 A1 | 7/2002 | Hartlaub | |
| 2002/0087116 A1 | 7/2002 | Hartlaub | |
| 2002/0095486 A1 | 7/2002 | Bahl | |
| 2002/0103675 A1 | 8/2002 | Vanelli | |
| 2002/0123905 A1 | 9/2002 | Goodroe et al. | |
| 2002/0143580 A1 | 10/2002 | Bristol et al. | |
| 2002/0152239 A1 | 10/2002 | Bautista-Lloyd et al. | |
| 2002/0154600 A1 | 10/2002 | Ido et al. | |
| 2002/0173702 A1 | 11/2002 | Lebel et al. | |
| 2002/0173875 A1 | 11/2002 | Wallace et al. | |
| 2002/0193679 A1 | 12/2002 | Malave et al. | |
| 2002/0194329 A1 | 12/2002 | Alling | |
| 2003/0009244 A1 | 1/2003 | Engleson | |
| 2003/0013959 A1 | 1/2003 | Grunwald et al. | |
| 2003/0014222 A1 | 1/2003 | Klass et al. | |
| 2003/0014817 A1 | 1/2003 | Gallant et al. | |
| 2003/0025602 A1 | 2/2003 | Medema et al. | |
| 2003/0028082 A1 | 2/2003 | Thompson | |
| 2003/0036683 A1 | 2/2003 | Kehr et al. | |
| 2003/0036744 A1 | 2/2003 | Struys et al. | |
| 2003/0047126 A1 | 3/2003 | Tomaschko | |
| 2003/0047600 A1 | 3/2003 | Nakanishi et al. | |
| 2003/0050621 A1 | 3/2003 | Lebel et al. | |
| 2003/0059750 A1 | 3/2003 | Bindler et al. | |
| 2003/0060688 A1 | 3/2003 | Ciarniello et al. | |

(56) References Cited

U.S. PATENT DOCUMENTS

| | | |
|---|---|---|
| 2003/0069963 A1 | 4/2003 | Jayant et al. |
| 2003/0079746 A1 | 5/2003 | Hickle |
| 2003/0097529 A1 | 5/2003 | Arimilli et al. |
| 2003/0104982 A1 | 6/2003 | Wittmann et al. |
| 2003/0105389 A1 | 6/2003 | Noonan et al. |
| 2003/0106553 A1 | 6/2003 | Vanderveen |
| 2003/0115358 A1 | 6/2003 | Yun |
| 2003/0120384 A1 | 6/2003 | Haitin et al. |
| 2003/0125662 A1 | 7/2003 | Bui |
| 2003/0130616 A1 | 7/2003 | Steil |
| 2003/0135087 A1 | 7/2003 | Hickle et al. |
| 2003/0139701 A1 | 7/2003 | White et al. |
| 2003/0140928 A1 | 7/2003 | Bui et al. |
| 2003/0140929 A1 | 7/2003 | Wilkes et al. |
| 2003/0141981 A1 | 7/2003 | Bui et al. |
| 2003/0143746 A1 | 7/2003 | Sage, Jr. |
| 2003/0144878 A1 | 7/2003 | Wilkes et al. |
| 2003/0158749 A1 | 8/2003 | Olchanski et al. |
| 2003/0187338 A1 | 10/2003 | Say et al. |
| 2003/0200116 A1 | 10/2003 | Forrester |
| 2003/0204416 A1 | 10/2003 | Acharya |
| 2003/0204781 A1 | 10/2003 | Peebles et al. |
| 2003/0212364 A1 | 11/2003 | Mann et al. |
| 2003/0212379 A1 | 11/2003 | Bylund et al. |
| 2003/0212821 A1 | 11/2003 | Gillies et al. |
| 2003/0216831 A1 | 11/2003 | Hart et al. |
| 2003/0217962 A1 | 11/2003 | Childers et al. |
| 2004/0008123 A1 | 1/2004 | Carrender et al. |
| 2004/0010786 A1 | 1/2004 | Cool et al. |
| 2004/0015132 A1 | 1/2004 | Brown |
| 2004/0019464 A1 | 1/2004 | Martucci et al. |
| 2004/0019607 A1 | 1/2004 | Moubayed et al. |
| 2004/0030323 A1 | 2/2004 | Ullestad et al. |
| 2004/0039257 A1 | 2/2004 | Hickle |
| 2004/0057226 A1 | 3/2004 | Berthou et al. |
| 2004/0064341 A1 | 4/2004 | Langan et al. |
| 2004/0064342 A1 | 4/2004 | Browne et al. |
| 2004/0064435 A1 | 4/2004 | Moubayed et al. |
| 2004/0073161 A1 | 4/2004 | Tachibana |
| 2004/0073811 A1 | 4/2004 | Sanin |
| 2004/0077934 A1 | 4/2004 | Massad |
| 2004/0078231 A1 | 4/2004 | Wilkes et al. |
| 2004/0078236 A1 | 4/2004 | Stoodley et al. |
| 2004/0085186 A1 | 5/2004 | Eveland et al. |
| 2004/0104271 A1 | 6/2004 | Martucci et al. |
| 2004/0122530 A1 | 6/2004 | Hansen |
| 2004/0128162 A1 | 7/2004 | Schlotterbeck et al. |
| 2004/0128163 A1 | 7/2004 | Goodman et al. |
| 2004/0133441 A1 | 7/2004 | Brady et al. |
| 2004/0139004 A1 | 7/2004 | Cohen et al. |
| 2004/0145480 A1 | 7/2004 | Despotis |
| 2004/0147034 A1 | 7/2004 | Gore et al. |
| 2004/0167464 A1 | 8/2004 | Ireland et al. |
| 2004/0167465 A1 | 8/2004 | Kohler |
| 2004/0167804 A1 | 8/2004 | Simpson |
| 2004/0172222 A1 | 9/2004 | Simpson et al. |
| 2004/0172283 A1 | 9/2004 | Vanderveen |
| 2004/0172301 A1 | 9/2004 | Mihai et al. |
| 2004/0172302 A1 | 9/2004 | Martucci et al. |
| 2004/0176667 A1 | 9/2004 | Mihai et al. |
| 2004/0176980 A1 | 9/2004 | Bulitta et al. |
| 2004/0176984 A1 | 9/2004 | White et al. |
| 2004/0181314 A1 | 9/2004 | Zaleski |
| 2004/0189708 A1 | 9/2004 | Larcheveque et al. |
| 2004/0193325 A1 | 9/2004 | Bonderud |
| 2004/0193328 A1 | 9/2004 | Butterfield et al. |
| 2004/0204673 A1 | 10/2004 | Flaherty et al. |
| 2004/0215278 A1 | 10/2004 | Stegink et al. |
| 2004/0220517 A1 | 11/2004 | Starkweather et al. |
| 2004/0225252 A1 | 11/2004 | Gillespie et al. |
| 2004/0236240 A1 | 11/2004 | Kraus et al. |
| 2004/0243438 A1 | 12/2004 | Mintz |
| 2004/0254434 A1 | 12/2004 | Goodnow et al. |
| 2005/0010269 A1 | 1/2005 | Lebel et al. |
| 2005/0020886 A1 | 1/2005 | Hutchinson et al. |
| 2005/0021006 A1 | 1/2005 | Tonnies |
| 2005/0027560 A1 | 2/2005 | Cook |
| 2005/0027567 A1 | 2/2005 | Taha |
| 2005/0038311 A1 | 2/2005 | Kuth |
| 2005/0038669 A1 | 2/2005 | Sachdeva et al. |
| 2005/0038680 A1 | 2/2005 | McMahon |
| 2005/0040226 A1 | 2/2005 | Al-Sheikh |
| 2005/0043620 A1 | 2/2005 | Fallows et al. |
| 2005/0049910 A1 | 3/2005 | Lancaster et al. |
| 2005/0055242 A1 | 3/2005 | Bello et al. |
| 2005/0055244 A1 | 3/2005 | Mullan et al. |
| 2005/0065465 A1 | 3/2005 | Lebel et al. |
| 2005/0065817 A1 | 3/2005 | Mihai et al. |
| 2005/0075544 A1 | 4/2005 | Shapiro et al. |
| 2005/0080801 A1 | 4/2005 | Kothandaraman et al. |
| 2005/0086071 A1 | 4/2005 | Fox, Jr. et al. |
| 2005/0086072 A1 | 4/2005 | Fox |
| 2005/0088704 A1 | 4/2005 | Vaschillo et al. |
| 2005/0090808 A1 | 4/2005 | Malave et al. |
| 2005/0099624 A1 | 5/2005 | Staehr |
| 2005/0102162 A1 | 5/2005 | Blumenfeld |
| 2005/0102165 A1 | 5/2005 | Oshita et al. |
| 2005/0102167 A1* | 5/2005 | Kapoor .................. G16H 40/20 705/3 |
| 2005/0102669 A1 | 5/2005 | Marney et al. |
| 2005/0107923 A1 | 5/2005 | Vanderveen |
| 2005/0108057 A1 | 5/2005 | Cohen et al. |
| 2005/0117529 A1 | 6/2005 | Ramos-Escano |
| 2005/0119788 A1 | 6/2005 | Engleson et al. |
| 2005/0119914 A1 | 6/2005 | Batch |
| 2005/0131739 A1 | 6/2005 | Rabinowitz et al. |
| 2005/0135306 A1 | 6/2005 | McAllen et al. |
| 2005/0137522 A1 | 6/2005 | Aoki |
| 2005/0137573 A1 | 6/2005 | McLaughlin |
| 2005/0138428 A1 | 6/2005 | McAllen et al. |
| 2005/0154769 A1 | 7/2005 | Eckart et al. |
| 2005/0160057 A1 | 7/2005 | Wefers et al. |
| 2005/0171503 A1 | 8/2005 | Van Den Berghe et al. |
| 2005/0171815 A1 | 8/2005 | Vanderveen |
| 2005/0177096 A1 | 8/2005 | Bollish et al. |
| 2005/0177395 A1 | 8/2005 | Blomquist |
| 2005/0182306 A1 | 8/2005 | Sloan |
| 2005/0182355 A1 | 8/2005 | Bui |
| 2005/0187950 A1 | 8/2005 | Parker |
| 2005/0192557 A1 | 9/2005 | Brauker et al. |
| 2005/0197554 A1 | 9/2005 | Polcha |
| 2005/0197621 A1 | 9/2005 | Poulsen et al. |
| 2005/0210037 A1 | 9/2005 | Wefers et al. |
| 2005/0216479 A1 | 9/2005 | Wefers et al. |
| 2005/0216480 A1 | 9/2005 | Wefers et al. |
| 2005/0223045 A1 | 10/2005 | Funahashi et al. |
| 2005/0224083 A1 | 10/2005 | Crass |
| 2005/0234746 A1 | 10/2005 | Funahashi |
| 2005/0240305 A1 | 10/2005 | Bogash et al. |
| 2005/0246416 A1 | 11/2005 | Blomquist |
| 2005/0251418 A1 | 11/2005 | Fox et al. |
| 2005/0261660 A1 | 11/2005 | Choi |
| 2005/0273059 A1 | 12/2005 | Mernoe et al. |
| 2005/0273367 A1 | 12/2005 | Nourie et al. |
| 2005/0277873 A1 | 12/2005 | Stewart et al. |
| 2005/0277890 A1 | 12/2005 | Stewart et al. |
| 2005/0278194 A1 | 12/2005 | Holland et al. |
| 2006/0004772 A1 | 1/2006 | Hagan et al. |
| 2006/0009727 A1 | 1/2006 | O'Mahony et al. |
| 2006/0009734 A1 | 1/2006 | Martin |
| 2006/0010098 A1 | 1/2006 | Goodnow et al. |
| 2006/0042139 A1 | 3/2006 | Mendes |
| 2006/0047270 A1 | 3/2006 | Shelton |
| 2006/0053036 A1 | 3/2006 | Coffman et al. |
| 2006/0064020 A1 | 3/2006 | Burnes et al. |
| 2006/0074633 A1 | 4/2006 | Mahesh et al. |
| 2006/0074920 A1 | 4/2006 | Wefers et al. |
| 2006/0079831 A1 | 4/2006 | Gilbert |
| 2006/0089539 A1 | 4/2006 | Miodownik et al. |
| 2006/0089854 A1 | 4/2006 | Holland et al. |
| 2006/0089855 A1 | 4/2006 | Holland et al. |
| 2006/0100746 A1 | 5/2006 | Leibner-Druska |
| 2006/0100907 A1 | 5/2006 | Holland et al. |
| 2006/0106649 A1 | 5/2006 | Eggers et al. |

(56) References Cited

U.S. PATENT DOCUMENTS

| | | |
|---|---|---|
| 2006/0111943 A1 | 5/2006 | Wu |
| 2006/0116904 A1 | 6/2006 | Brem |
| 2006/0116907 A1 | 6/2006 | Rhodes et al. |
| 2006/0122481 A1 | 6/2006 | Sievenpiper et al. |
| 2006/0122867 A1 | 6/2006 | Eggers et al. |
| 2006/0129140 A1 | 6/2006 | Todd et al. |
| 2006/0129429 A1 | 6/2006 | Moubayed et al. |
| 2006/0129434 A1 | 6/2006 | Smitherman et al. |
| 2006/0129435 A1 | 6/2006 | Smitherman et al. |
| 2006/0136266 A1 | 6/2006 | Tarassenko et al. |
| 2006/0136271 A1 | 6/2006 | Eggers et al. |
| 2006/0143051 A1 | 6/2006 | Eggers et al. |
| 2006/0173260 A1 | 8/2006 | Gaoni et al. |
| 2006/0173406 A1 | 8/2006 | Hayes et al. |
| 2006/0173715 A1 | 8/2006 | Wang et al. |
| 2006/0173927 A1 | 8/2006 | Beyer et al. |
| 2006/0190302 A1 | 8/2006 | Eggers et al. |
| 2006/0195022 A1 | 8/2006 | Trepagnier et al. |
| 2006/0200007 A1 | 9/2006 | Brockway et al. |
| 2006/0200369 A1 | 9/2006 | Batch et al. |
| 2006/0211404 A1 | 9/2006 | Cromp et al. |
| 2006/0224141 A1 | 10/2006 | Rush et al. |
| 2006/0229918 A1 | 10/2006 | Fotsch et al. |
| 2006/0236373 A1 | 10/2006 | Graves et al. |
| 2006/0247606 A1 | 11/2006 | Batch |
| 2006/0253554 A1 | 11/2006 | Uwais |
| 2006/0258985 A1 | 11/2006 | Russell |
| 2006/0259327 A1 | 11/2006 | Hoag |
| 2006/0264895 A1 | 11/2006 | Flanders |
| 2006/0267753 A1 | 11/2006 | Hussey et al. |
| 2006/0268710 A1 | 11/2006 | Appanna et al. |
| 2006/0270971 A1 | 11/2006 | Gelfand et al. |
| 2006/0277206 A1 | 12/2006 | Bailey et al. |
| 2006/0287885 A1 | 12/2006 | Frick |
| 2007/0015972 A1 | 1/2007 | Wang et al. |
| 2007/0016443 A1 | 1/2007 | Wachman et al. |
| 2007/0021715 A1 | 1/2007 | Kohlbrenner et al. |
| 2007/0027506 A1 | 2/2007 | Stender et al. |
| 2007/0060796 A1 | 3/2007 | Kim |
| 2007/0060870 A1 | 3/2007 | Tolle et al. |
| 2007/0060871 A1 | 3/2007 | Istoc |
| 2007/0061393 A1 | 3/2007 | Moore |
| 2007/0065363 A1 | 3/2007 | Dalal et al. |
| 2007/0073419 A1 | 3/2007 | Sesay |
| 2007/0073822 A1 | 3/2007 | Bennett et al. |
| 2007/0078314 A1 | 4/2007 | Grounsell |
| 2007/0083870 A1 | 4/2007 | Kanakogi |
| 2007/0088333 A1 | 4/2007 | Levin et al. |
| 2007/0093786 A1 | 4/2007 | Goldsmith et al. |
| 2007/0100665 A1 | 5/2007 | Brown |
| 2007/0100667 A1 | 5/2007 | Bardy |
| 2007/0106126 A1 | 5/2007 | Mannheimer et al. |
| 2007/0112298 A1 | 5/2007 | Mueller et al. |
| 2007/0116037 A1 | 5/2007 | Moore |
| 2007/0118405 A1 | 5/2007 | Campbell et al. |
| 2007/0135866 A1 | 6/2007 | Baker et al. |
| 2007/0136098 A1 | 6/2007 | Smythe et al. |
| 2007/0142822 A1 | 6/2007 | Remde |
| 2007/0156282 A1 | 7/2007 | Dunn |
| 2007/0156452 A1 | 7/2007 | Batch |
| 2007/0169008 A1 | 7/2007 | Varanasi et al. |
| 2007/0179448 A1 | 8/2007 | Lim et al. |
| 2007/0186923 A1 | 8/2007 | Poutiatine et al. |
| 2007/0191817 A1 | 8/2007 | Martin |
| 2007/0191973 A1 | 8/2007 | Holzbauer et al. |
| 2007/0213657 A1 | 9/2007 | Jennewine et al. |
| 2007/0213684 A1 | 9/2007 | Hickle et al. |
| 2007/0214003 A1 | 9/2007 | Holland et al. |
| 2007/0215545 A1 | 9/2007 | Bissler et al. |
| 2007/0232867 A1 | 10/2007 | Hansmann |
| 2007/0233035 A1 | 10/2007 | Wehba et al. |
| 2007/0233049 A1 | 10/2007 | Wehba et al. |
| 2007/0233206 A1 | 10/2007 | Frikart |
| 2007/0240215 A1 | 10/2007 | Flores |
| 2007/0251835 A1 | 11/2007 | Mehta et al. |
| 2007/0253021 A1 | 11/2007 | Mehta et al. |
| 2007/0254593 A1 | 11/2007 | Jollota et al. |
| 2007/0255125 A1 | 11/2007 | Moberg et al. |
| 2007/0257788 A1 | 11/2007 | Carlson |
| 2007/0258395 A1 | 11/2007 | Jollota et al. |
| 2007/0299687 A1 | 12/2007 | Palmer et al. |
| 2007/0299695 A1 | 12/2007 | Jung et al. |
| 2008/0001771 A1 | 1/2008 | Faoro et al. |
| 2008/0004904 A1 | 1/2008 | Tran |
| 2008/0009684 A1 | 1/2008 | Corsetti et al. |
| 2008/0033361 A1 | 2/2008 | Evans et al. |
| 2008/0033966 A1 | 2/2008 | Wahl |
| 2008/0034323 A1 | 2/2008 | Blomquist |
| 2008/0041942 A1 | 2/2008 | Aissa |
| 2008/0052704 A1 | 2/2008 | Wysocki |
| 2008/0065007 A1 | 3/2008 | Peterson et al. |
| 2008/0065417 A1 | 3/2008 | Jung et al. |
| 2008/0071217 A1 | 3/2008 | Moubayed et al. |
| 2008/0071251 A1 | 3/2008 | Moubayed et al. |
| 2008/0086088 A1 | 4/2008 | Malcolm |
| 2008/0091466 A1 | 4/2008 | Butler et al. |
| 2008/0095339 A1 | 4/2008 | Elliott |
| 2008/0097289 A1 | 4/2008 | Steil et al. |
| 2008/0097552 A1 | 4/2008 | Dicks et al. |
| 2008/0126969 A1 | 5/2008 | Blomquist |
| 2008/0139907 A1 | 6/2008 | Rao et al. |
| 2008/0148047 A1 | 6/2008 | Appenzeller et al. |
| 2008/0149117 A1 | 6/2008 | Raghuram |
| 2008/0154177 A1 | 6/2008 | Moubayed et al. |
| 2008/0172337 A1 | 7/2008 | Banfield et al. |
| 2008/0184219 A1 | 7/2008 | Matsumoto |
| 2008/0188796 A1 | 8/2008 | Steil et al. |
| 2008/0214919 A1 | 9/2008 | Harmon et al. |
| 2008/0246748 A1 | 10/2008 | Cassidy et al. |
| 2008/0256305 A1 | 10/2008 | Kwon |
| 2008/0259926 A1 | 10/2008 | Tavares et al. |
| 2008/0260149 A1* | 10/2008 | Gehrmann ......... G06Q 20/3821 380/247 |
| 2008/0262469 A1 | 10/2008 | Bristol et al. |
| 2008/0269714 A1 | 10/2008 | Mastrototaro et al. |
| 2008/0269723 A1 | 10/2008 | Mastrototaro et al. |
| 2008/0275384 A1 | 11/2008 | Mastrototaro et al. |
| 2008/0300572 A1 | 12/2008 | Rankers et al. |
| 2008/0301298 A1 | 12/2008 | Bernardi et al. |
| 2008/0320387 A1 | 12/2008 | Sasaki et al. |
| 2008/0320466 A1 | 12/2008 | Dias |
| 2009/0003554 A1 | 1/2009 | Katis et al. |
| 2009/0005703 A1 | 1/2009 | Fasciano |
| 2009/0005728 A1 | 1/2009 | Weinert et al. |
| 2009/0006061 A1 | 1/2009 | Thukral et al. |
| 2009/0006129 A1 | 1/2009 | Thukral |
| 2009/0006133 A1 | 1/2009 | Weinert |
| 2009/0018495 A1 | 1/2009 | Panduro |
| 2009/0036750 A1 | 2/2009 | Weinstein et al. |
| 2009/0051560 A1 | 2/2009 | Manning et al. |
| 2009/0054743 A1 | 2/2009 | Stewart |
| 2009/0054754 A1 | 2/2009 | McMahon et al. |
| 2009/0057399 A1 | 3/2009 | Sajkowsky |
| 2009/0063187 A1 | 3/2009 | Johnson et al. |
| 2009/0069785 A1 | 3/2009 | Miller et al. |
| 2009/0099867 A1 | 4/2009 | Newman |
| 2009/0135196 A1 | 5/2009 | Holland et al. |
| 2009/0143662 A1 | 6/2009 | Estes et al. |
| 2009/0149743 A1 | 6/2009 | Barron et al. |
| 2009/0150174 A1 | 6/2009 | Buck et al. |
| 2009/0150439 A1 | 6/2009 | Gejdos et al. |
| 2009/0150878 A1 | 6/2009 | Pathak et al. |
| 2009/0157695 A1 | 6/2009 | Roberts |
| 2009/0158274 A1 | 6/2009 | Roberts |
| 2009/0177146 A1 | 7/2009 | Nesbitt et al. |
| 2009/0177769 A1 | 7/2009 | Roberts |
| 2009/0183147 A1 | 7/2009 | Davis et al. |
| 2009/0209938 A1 | 8/2009 | Aalto-Setala |
| 2009/0210250 A1 | 8/2009 | Prax et al. |
| 2009/0221890 A1 | 9/2009 | Saffer et al. |
| 2009/0231249 A1 | 9/2009 | Wang et al. |
| 2009/0270833 A1 | 10/2009 | DeBelser |
| 2009/0275886 A1 | 11/2009 | Blomquist et al. |
| 2009/0275896 A1 | 11/2009 | Kamen et al. |

(56) References Cited

U.S. PATENT DOCUMENTS

| | | |
|---|---|---|
| 2009/0284691 A1 | 11/2009 | Marhefka et al. |
| 2009/0292340 A1 | 11/2009 | Mass et al. |
| 2009/0306573 A1 | 12/2009 | Gagner et al. |
| 2009/0326340 A1 | 12/2009 | Wang |
| 2009/0326516 A1 | 12/2009 | Bangera et al. |
| 2010/0008377 A1 | 1/2010 | Hasti et al. |
| 2010/0022988 A1 | 1/2010 | Wochner |
| 2010/0036310 A1 | 2/2010 | Hillman |
| 2010/0056992 A1 | 3/2010 | Hayter |
| 2010/0083060 A1 | 4/2010 | Rahman |
| 2010/0095229 A1 | 4/2010 | Dixon et al. |
| 2010/0121170 A1 | 5/2010 | Rule |
| 2010/0121246 A1 | 5/2010 | Peters et al. |
| 2010/0121415 A1 | 5/2010 | Skelton et al. |
| 2010/0121654 A1 | 5/2010 | Portnoy et al. |
| 2010/0121752 A1 | 5/2010 | Banigan et al. |
| 2010/0130933 A1 | 5/2010 | Holland et al. |
| 2010/0131434 A1 | 5/2010 | Magent et al. |
| 2010/0138523 A1 | 6/2010 | Umess et al. |
| 2010/0146137 A1 | 6/2010 | Wu et al. |
| 2010/0156633 A1 | 6/2010 | Buck et al. |
| 2010/0160854 A1 | 6/2010 | Gauthier |
| 2010/0160860 A1 | 6/2010 | Celentano et al. |
| 2010/0174266 A1 | 7/2010 | Estes |
| 2010/0191525 A1 | 7/2010 | Rabenko et al. |
| 2010/0198034 A1 | 8/2010 | Thomas et al. |
| 2010/0198196 A1 | 8/2010 | Wei |
| 2010/0200506 A1 | 8/2010 | Ware et al. |
| 2010/0205459 A1* | 8/2010 | Schwarz .............. G06F 21/554 713/189 |
| 2010/0209268 A1 | 8/2010 | Davis |
| 2010/0212675 A1 | 8/2010 | Walling et al. |
| 2010/0217621 A1 | 8/2010 | Schoenberg |
| 2010/0234708 A1 | 9/2010 | Buck et al. |
| 2010/0250732 A1 | 9/2010 | Bucknell |
| 2010/0271479 A1 | 10/2010 | Heydlauf |
| 2010/0273738 A1 | 10/2010 | Valcke et al. |
| 2010/0274218 A1 | 10/2010 | Yodfat et al. |
| 2010/0280486 A1 | 11/2010 | Khair et al. |
| 2010/0292634 A1 | 11/2010 | Kircher |
| 2010/0298765 A1 | 11/2010 | Budiman et al. |
| 2010/0318025 A1 | 12/2010 | John |
| 2011/0001605 A1 | 1/2011 | Kiani et al. |
| 2011/0021898 A1 | 1/2011 | Wei et al. |
| 2011/0028885 A1 | 2/2011 | Eggers et al. |
| 2011/0040158 A1 | 2/2011 | Katz et al. |
| 2011/0060758 A1 | 3/2011 | Schlotterbeck et al. |
| 2011/0071844 A1 | 3/2011 | Cannon et al. |
| 2011/0072379 A1 | 3/2011 | Gannon |
| 2011/0078253 A1 | 3/2011 | Chan et al. |
| 2011/0078608 A1 | 3/2011 | Gannon et al. |
| 2011/0093284 A1 | 4/2011 | Dicks et al. |
| 2011/0099313 A1 | 4/2011 | Bolanowski |
| 2011/0106318 A1 | 5/2011 | Ledford et al. |
| 2011/0125095 A1 | 5/2011 | Lebel et al. |
| 2011/0138185 A1 | 6/2011 | Ju et al. |
| 2011/0166628 A1 | 7/2011 | Jain |
| 2011/0170692 A1* | 7/2011 | Konrad ................ G06F 21/606 380/260 |
| 2011/0175728 A1 | 7/2011 | Baker, Jr. |
| 2011/0178462 A1 | 7/2011 | Moberg et al. |
| 2011/0185010 A1 | 7/2011 | Shatsky et al. |
| 2011/0196748 A1 | 8/2011 | Caron et al. |
| 2011/0231216 A1 | 9/2011 | Fyke et al. |
| 2011/0252230 A1 | 10/2011 | Segre et al. |
| 2011/0257496 A1 | 10/2011 | Terashima et al. |
| 2011/0257798 A1 | 10/2011 | Ali et al. |
| 2011/0259954 A1 | 10/2011 | Bartz et al. |
| 2011/0264043 A1 | 10/2011 | Kotnick et al. |
| 2011/0264044 A1 | 10/2011 | Bartz et al. |
| 2011/0266221 A1 | 11/2011 | Ware et al. |
| 2011/0270045 A1 | 11/2011 | Lebel et al. |
| 2011/0275904 A1 | 11/2011 | Lebel et al. |
| 2011/0286457 A1 | 11/2011 | Ee |
| 2011/0289314 A1 | 11/2011 | Whitcomb |
| 2011/0289497 A1 | 11/2011 | Kiaie et al. |
| 2011/0295196 A1 | 12/2011 | Chazot et al. |
| 2011/0295341 A1 | 12/2011 | Estes et al. |
| 2011/0296051 A1 | 12/2011 | Vange |
| 2011/0296411 A1 | 12/2011 | Tang et al. |
| 2011/0313789 A1 | 12/2011 | Karmen et al. |
| 2011/0319813 A1 | 12/2011 | Kamen et al. |
| 2011/0320049 A1 | 12/2011 | Chossat et al. |
| 2012/0005680 A1 | 1/2012 | Dolby et al. |
| 2012/0011253 A1 | 1/2012 | Friedman et al. |
| 2012/0016305 A1 | 1/2012 | Jollota |
| 2012/0029941 A1 | 2/2012 | Malave et al. |
| 2012/0036102 A1 | 2/2012 | Fletcher et al. |
| 2012/0036550 A1 | 2/2012 | Rodriguez |
| 2012/0066501 A1 | 3/2012 | Xiong |
| 2012/0070045 A1 | 3/2012 | Vesper et al. |
| 2012/0095437 A1 | 4/2012 | Hemmerling |
| 2012/0102568 A1* | 4/2012 | Tarbotton .............. G06F 21/552 726/23 |
| 2012/0112903 A1 | 5/2012 | Kaib et al. |
| 2012/0130198 A1 | 5/2012 | Beaule |
| 2012/0143116 A1 | 6/2012 | Ware et al. |
| 2012/0150556 A1 | 6/2012 | Galasso et al. |
| 2012/0157920 A1 | 6/2012 | Flachbart et al. |
| 2012/0179135 A1 | 7/2012 | Rinehart et al. |
| 2012/0179136 A1 | 7/2012 | Rinehart et al. |
| 2012/0185267 A1 | 7/2012 | Kamen et al. |
| 2012/0203177 A1 | 8/2012 | Lanier |
| 2012/0245554 A1 | 9/2012 | Kawamura |
| 2012/0259978 A1 | 10/2012 | Petersen et al. |
| 2012/0260012 A1 | 10/2012 | Gao-Saari et al. |
| 2012/0277716 A1 | 11/2012 | Ali et al. |
| 2012/0283630 A1 | 11/2012 | Lee et al. |
| 2012/0284734 A1 | 11/2012 | McQuaid et al. |
| 2012/0323212 A1 | 12/2012 | Murphy |
| 2012/0330380 A1 | 12/2012 | Corndorf |
| 2013/0006666 A1 | 1/2013 | Schneider |
| 2013/0006702 A1 | 1/2013 | Wu |
| 2013/0012877 A1 | 1/2013 | Debelser et al. |
| 2013/0012879 A1 | 1/2013 | Debelser et al. |
| 2013/0012880 A1 | 1/2013 | Blomquist |
| 2013/0015980 A1 | 1/2013 | Evans et al. |
| 2013/0036403 A1 | 2/2013 | Geist |
| 2013/0036412 A1 | 2/2013 | Birtwhistle et al. |
| 2013/0066265 A1 | 3/2013 | Grant |
| 2013/0072872 A1 | 3/2013 | Yodfat et al. |
| 2013/0091350 A1 | 4/2013 | Gluck |
| 2013/0096444 A1 | 4/2013 | Condurso et al. |
| 2013/0096648 A1 | 4/2013 | Benson |
| 2013/0102963 A1 | 4/2013 | Marsh et al. |
| 2013/0114594 A1 | 5/2013 | Van Zijst |
| 2013/0116578 A1 | 5/2013 | An |
| 2013/0133083 A1 | 5/2013 | Kurumai |
| 2013/0138452 A1 | 5/2013 | Cork et al. |
| 2013/0150824 A1 | 6/2013 | Estes et al. |
| 2013/0167245 A1 | 6/2013 | Birtwhistle et al. |
| 2013/0173473 A1 | 7/2013 | Birtwhistle et al. |
| 2013/0191770 A1 | 7/2013 | Bartz et al. |
| 2013/0204188 A1 | 8/2013 | Kamen et al. |
| 2013/0218080 A1 | 8/2013 | Peterfreund et al. |
| 2013/0274669 A1 | 10/2013 | Stempfle et al. |
| 2013/0275539 A1 | 10/2013 | Gross et al. |
| 2013/0291116 A1 | 10/2013 | Homer |
| 2013/0296823 A1 | 11/2013 | Melker et al. |
| 2013/0296984 A1 | 11/2013 | Burnett et al. |
| 2013/0317753 A1 | 11/2013 | Kamen et al. |
| 2013/0346108 A1 | 12/2013 | Kamen et al. |
| 2014/0025392 A1 | 1/2014 | Chandrasenan |
| 2014/0108783 A1 | 4/2014 | Suzuki |
| 2014/0142540 A1 | 5/2014 | Imhof |
| 2014/0142963 A1 | 5/2014 | Hill et al. |
| 2014/0163517 A1 | 6/2014 | Finan et al. |
| 2014/0172994 A1 | 6/2014 | Raumann et al. |
| 2014/0180711 A1 | 6/2014 | Kamen et al. |
| 2014/0197950 A1 | 7/2014 | Shupp et al. |
| 2014/0215490 A1 | 7/2014 | Mathur et al. |
| 2014/0223181 A1* | 8/2014 | Bernsen .............. H04L 63/0428 713/168 |
| 2014/0257251 A1 | 9/2014 | Bush et al. |

(56) References Cited

U.S. PATENT DOCUMENTS

| | | |
|---|---|---|
| 2014/0266790 A1 | 9/2014 | Al-Ali et al. |
| 2014/0266794 A1 | 9/2014 | Brown et al. |
| 2014/0269643 A1 | 9/2014 | Sun |
| 2014/0276571 A1 | 9/2014 | Ludolph |
| 2014/0280522 A1 | 9/2014 | Watte |
| 2014/0294177 A1 | 10/2014 | Shastry et al. |
| 2014/0297329 A1 | 10/2014 | Rock |
| 2014/0316819 A1 | 10/2014 | Dunsirn et al. |
| 2014/0318639 A1 | 10/2014 | Peret et al. |
| 2014/0366878 A1 | 12/2014 | Baron |
| 2014/0371543 A1 | 12/2014 | Steinhauer et al. |
| 2015/0005935 A1 | 1/2015 | Bae et al. |
| 2015/0006907 A1 | 1/2015 | Brouwer et al. |
| 2015/0045729 A1 | 2/2015 | Denzer et al. |
| 2015/0058960 A1 | 2/2015 | Schmoyer et al. |
| 2015/0066531 A1 | 3/2015 | Jacobson et al. |
| 2015/0081894 A1 | 3/2015 | Blomquist |
| 2015/0100038 A1 | 4/2015 | McCann et al. |
| 2015/0100787 A1 | 4/2015 | Westin et al. |
| 2015/0117234 A1 | 4/2015 | Raman et al. |
| 2015/0151051 A1 | 6/2015 | Tsoukalis |
| 2015/0161354 A1 | 6/2015 | Blomquist |
| 2015/0199192 A1 | 7/2015 | Borges et al. |
| 2015/0199485 A1 | 7/2015 | Borges et al. |
| 2015/0207626 A1 | 7/2015 | Neftel et al. |
| 2015/0220890 A1 | 8/2015 | Seshadri et al. |
| 2015/0230760 A1 | 8/2015 | Schneider |
| 2015/0281128 A1 | 10/2015 | Sindhu |
| 2015/0325064 A1 | 11/2015 | Downey |
| 2015/0328396 A1 | 11/2015 | Adams et al. |
| 2015/0352301 A1 | 12/2015 | Stedman et al. |
| 2015/0371004 A1 | 12/2015 | Jones |
| 2015/0379237 A1 | 12/2015 | Mills et al. |
| 2016/0001003 A1 | 1/2016 | Perazzo et al. |
| 2016/0006695 A1 | 1/2016 | Prodoehl et al. |
| 2016/0015885 A1 | 1/2016 | Pananen et al. |
| 2016/0034655 A1 | 2/2016 | Gray et al. |
| 2016/0045661 A1 | 2/2016 | Gray et al. |
| 2016/0063471 A1 | 3/2016 | Kobres et al. |
| 2016/0158437 A1 | 6/2016 | Biasi et al. |
| 2016/0228633 A1 | 8/2016 | Welsch et al. |
| 2016/0241391 A1 | 8/2016 | Fenster |
| 2016/0277152 A1 | 9/2016 | Xiang et al. |
| 2016/0285876 A1 | 9/2016 | Perez et al. |
| 2016/0317742 A1 | 11/2016 | Gannon et al. |
| 2016/0337124 A1* | 11/2016 | Rozman ............... G06F 21/6209 |
| 2016/0350513 A1 | 12/2016 | Jacobson et al. |
| 2016/0378618 A1 | 12/2016 | Cmielowski |
| 2017/0034277 A1 | 2/2017 | Jackson et al. |
| 2017/0063559 A1 | 3/2017 | Wallrabenstein |
| 2017/0099148 A1 | 4/2017 | Ochmanski et al. |
| 2017/0104645 A1 | 4/2017 | Wooton et al. |
| 2017/0111301 A1 | 4/2017 | Robinson |
| 2017/0140134 A1 | 5/2017 | Brough et al. |
| 2017/0146381 A1 | 5/2017 | Eckel et al. |
| 2017/0149567 A1 | 5/2017 | Moskal |
| 2017/0149929 A1 | 5/2017 | Moskal |
| 2017/0214762 A1 | 7/2017 | Swain et al. |
| 2017/0258401 A1 | 9/2017 | Volpe |
| 2017/0258986 A1 | 9/2017 | Tsoiukalis |
| 2017/0262590 A1 | 9/2017 | Karakosta et al. |
| 2017/0274140 A1 | 9/2017 | Howard et al. |
| 2017/0286637 A1 | 10/2017 | Arrizza et al. |
| 2017/0325091 A1 | 11/2017 | Freeman et al. |
| 2017/0331804 A1 | 11/2017 | Jellison et al. |
| 2017/0351841 A1 | 12/2017 | Moskal |
| 2018/0063724 A1 | 3/2018 | Zhang et al. |
| 2018/0121613 A1 | 5/2018 | Connely, IV et al. |
| 2018/0122502 A1 | 5/2018 | Jones et al. |
| 2018/0126067 A1 | 5/2018 | Ledford et al. |
| 2018/0157821 A1 | 6/2018 | Fan |
| 2018/0181712 A1 | 6/2018 | Ensey et al. |
| 2018/0247712 A1 | 8/2018 | Muhsin et al. |
| 2018/0272117 A1 | 9/2018 | Fangrow |
| 2018/0278594 A1 | 9/2018 | Schiffman et al. |
| 2018/0317826 A1 | 11/2018 | Muhsin et al. |
| 2018/0322948 A1 | 11/2018 | Drost et al. |
| 2018/0359085 A1 | 12/2018 | Dervyn |
| 2018/0373881 A1* | 12/2018 | Thom ................... H04L 9/0643 |
| 2019/0006044 A1 | 1/2019 | Brask |
| 2019/0030329 A1 | 1/2019 | Hannaman et al. |
| 2019/0036688 A1 | 1/2019 | Wasily et al. |
| 2019/0096518 A1 | 3/2019 | Pace |
| 2019/0132196 A1 | 5/2019 | Trivedi et al. |
| 2019/0166501 A1 | 5/2019 | Debates et al. |
| 2019/0172590 A1 | 6/2019 | Vesto et al. |
| 2019/0182216 A1* | 6/2019 | Gulak ................. H04L 63/0414 |
| 2019/0207965 A1 | 7/2019 | Espinosa |
| 2019/0228863 A1 | 7/2019 | Dharwad et al. |
| 2019/0229982 A1 | 7/2019 | Ikuta et al. |
| 2019/0244689 A1 | 8/2019 | Atkin |
| 2019/0245942 A1 | 8/2019 | Moskal |
| 2019/0311803 A1 | 10/2019 | Kohlbrecher et al. |
| 2019/0328618 A1* | 10/2019 | Hasegawa ............. A61J 7/0076 |
| 2019/0348160 A1 | 11/2019 | Heavelyn et al. |
| 2019/0392929 A1 | 12/2019 | Gassman |
| 2020/0023127 A1 | 1/2020 | Simpson et al. |
| 2020/0027541 A1 | 1/2020 | Xavier et al. |
| 2020/0027548 A1 | 1/2020 | Xavier et al. |
| 2020/0027550 A1 | 1/2020 | Xavier et al. |
| 2020/0027551 A1 | 1/2020 | Xavier et al. |
| 2020/0035355 A1 | 1/2020 | Xavier et al. |
| 2020/0054825 A1 | 2/2020 | Kamen et al. |
| 2020/0153627 A1 | 5/2020 | Wentz |
| 2020/0206413 A1 | 7/2020 | Silkaitis et al. |
| 2020/0220865 A1 | 7/2020 | Finger et al. |
| 2020/0282139 A1 | 9/2020 | Susi |
| 2020/0334497 A1 | 10/2020 | Barrett et al. |
| 2020/0335194 A1 | 10/2020 | Jacobson et al. |
| 2020/0351376 A1 | 11/2020 | Moskal |
| 2020/0353167 A1 | 11/2020 | Vivek et al. |
| 2020/0353168 A1 | 11/2020 | Keenan et al. |
| 2021/0014259 A1 | 1/2021 | Harris et al. |
| 2021/0043296 A1 | 2/2021 | Xavier et al. |
| 2021/0045640 A1 | 2/2021 | Poltorak |
| 2021/0050085 A1* | 2/2021 | Hayter ................... G16H 10/60 |
| 2021/0085855 A1 | 3/2021 | Belkin et al. |
| 2021/0098106 A1 | 4/2021 | Kohlbrecher et al. |
| 2021/0098107 A1 | 4/2021 | Xavier et al. |
| 2021/0105206 A1 | 4/2021 | Jha et al. |
| 2021/0252210 A1 | 8/2021 | Day et al. |
| 2021/0358603 A1 | 11/2021 | Xavier et al. |
| 2021/0375421 A1 | 12/2021 | Ruchti et al. |
| 2021/0375438 A1 | 12/2021 | Xavier et al. |
| 2021/0409362 A1 | 12/2021 | Katis et al. |
| 2022/0021531 A1* | 1/2022 | Zach ....................... G06F 21/81 |
| 2022/0037011 A1 | 2/2022 | Fryman |
| 2022/0037012 A1 | 2/2022 | Fryman |
| 2022/0054746 A1* | 2/2022 | Patel ................... G06F 21/6245 |
| 2022/0062541 A1 | 3/2022 | Kamen et al. |
| 2022/0070221 A1* | 3/2022 | Labudde ............... H04L 9/0841 |
| 2022/0129452 A1 | 4/2022 | Butler et al. |
| 2022/0150307 A1 | 5/2022 | Walsh et al. |
| 2022/0189605 A1 | 6/2022 | Kelly et al. |
| 2022/0223283 A1 | 7/2022 | Biasi et al. |
| 2022/0331513 A1 | 10/2022 | Howard et al. |
| 2022/0384059 A1 | 12/2022 | Xavier et al. |
| 2023/0009417 A1 | 1/2023 | Xavier et al. |
| 2023/0108034 A1* | 4/2023 | Fischer ................. H04L 9/3242 713/183 |
| 2023/0139360 A1 | 5/2023 | Kohlbrecher et al. |
| 2023/0145267 A1 | 5/2023 | Xavier et al. |
| 2023/0147762 A1 | 5/2023 | Xavier et al. |
| 2023/0253108 A1 | 8/2023 | Dharwad et al. |
| 2023/0298768 A1 | 9/2023 | Jacobson et al. |
| 2023/0320935 A1 | 10/2023 | Tagliamento |
| 2023/0410989 A1 | 12/2023 | Xavier et al. |
| 2024/0038358 A1 | 2/2024 | Xavier et al. |

(56) References Cited

U.S. PATENT DOCUMENTS

| | | |
|---|---|---|
| 2024/0047035 A1 | 2/2024 | Ruchti et al. |
| 2024/0071609 A1 | 2/2024 | Rohlwing |

FOREIGN PATENT DOCUMENTS

| | | |
|---|---|---|
| CA | 2 060 151 | 8/1997 |
| CA | 2 125 300 | 10/1999 |
| CA | 2 630 102 | 10/2008 |
| CA | 2 687 587 | 12/2008 |
| CA | 2 897 897 | 7/2014 |
| CA | 2 898 825 | 7/2014 |
| CA | 2 900 564 | 10/2014 |
| CA | 2 606 968 | 1/2020 |
| CN | 1759398 | 4/2006 |
| CN | 102521474 | 6/2012 |
| CN | 103816582 | 5/2014 |
| CN | 103920206 | 7/2014 |
| CN | 102300501 | 4/2015 |
| CN | 104487976 | 4/2015 |
| CN | 107810536 | 1/2023 |
| DE | 31 12 762 | 1/1983 |
| DE | 34 35 647 | 7/1985 |
| DE | 198 44 252 | 3/2000 |
| DE | 199 32 147 | 1/2001 |
| DE | 103 52 456 | 7/2005 |
| EP | 0 319 267 | 6/1989 |
| EP | 0 380 061 | 8/1990 |
| EP | 0 384 155 | 8/1990 |
| EP | 0 460 533 | 12/1991 |
| EP | 0 564 127 | 6/1993 |
| EP | 0 633 035 | 1/1995 |
| EP | 0 652 528 | 5/1995 |
| EP | 0 672 427 | 9/1995 |
| EP | 0 683 465 | 11/1995 |
| EP | 0 880 936 | 12/1998 |
| EP | 1 050 993 | 11/2000 |
| EP | 1 157 711 | 11/2001 |
| EP | 1 174 817 | 1/2002 |
| EP | 0 664 102 | 4/2002 |
| EP | 1 197 178 | 4/2002 |
| EP | 0 830 775 | 8/2002 |
| EP | 1 500 025 | 4/2003 |
| EP | 1 487 171 | 7/2007 |
| EP | 1 933 497 | 6/2008 |
| EP | 2 026 223 | 2/2009 |
| EP | 2 113 842 | 11/2009 |
| EP | 2 228 004 | 9/2010 |
| EP | 2 243 506 | 10/2010 |
| EP | 2 410 448 | 1/2012 |
| EP | 2 742 961 | 6/2014 |
| EP | 2 874 087 | 5/2015 |
| ES | 2 371 995 | 1/2012 |
| FR | 2 717 919 | 9/1995 |
| GB | 2 285 135 | 6/1995 |
| JP | 04-161139 | 6/1992 |
| JP | 07-502678 | 3/1995 |
| JP | 11-500643 | 1/1999 |
| JP | 2000-316820 | 11/2000 |
| JP | 2002-531154 | 9/2002 |
| JP | 2003-016183 | 1/2003 |
| JP | 2003-296173 | 10/2003 |
| JP | 2003-308586 | 10/2003 |
| JP | 2005-021463 | 1/2005 |
| JP | 2005-527284 | 9/2005 |
| JP | 2005-284846 | 10/2005 |
| JP | 2006-047319 | 2/2006 |
| JP | 2006-520949 | 9/2006 |
| JP | 2007-518479 | 7/2007 |
| JP | 2007-525256 | 9/2007 |
| JP | 2008-080036 | 4/2008 |
| JP | 2008-516303 | 5/2008 |
| JP | 2008-158622 | 7/2008 |
| JP | 2008-529675 | 8/2008 |
| JP | 2009-163534 | 7/2009 |
| JP | 2010-502361 | 1/2010 |
| JP | 2011-506048 | 3/2011 |
| JP | 2012-011204 | 1/2012 |
| JP | 2012-070991 | 4/2012 |
| JP | 2012-523895 | 10/2012 |
| JP | 2014-068283 | 4/2014 |
| JP | 5647644 | 1/2015 |
| TW | 200426656 | 12/2004 |
| TW | 1631966 | 8/2018 |
| WO | WO 84/001719 | 5/1984 |
| WO | WO 91/016416 | 10/1991 |
| WO | WO 92/010985 | 7/1992 |
| WO | WO 92/013322 | 8/1992 |
| WO | WO 94/005355 | 3/1994 |
| WO | WO 96/008755 | 3/1996 |
| WO | WO 96/025186 | 8/1996 |
| WO | WO 96/025963 | 8/1996 |
| WO | WO 98/012670 | 3/1998 |
| WO | WO 98/019263 | 5/1998 |
| WO | WO 99/051003 | 10/1999 |
| WO | WO 00/013580 | 3/2000 |
| WO | WO 00/053243 | 9/2000 |
| WO | WO 01/014974 | 3/2001 |
| WO | WO 01/033484 | 5/2001 |
| WO | WO 01/045014 | 6/2001 |
| WO | WO 01/083007 | 11/2001 |
| WO | WO 02/005702 | 1/2002 |
| WO | WO 02/036044 | 5/2002 |
| WO | WO 02/049153 | 6/2002 |
| WO | WO 02/049279 | 6/2002 |
| WO | WO 02/069099 | 9/2002 |
| WO | WO 02/081015 | 10/2002 |
| WO | WO 02/088875 | 11/2002 |
| WO | WO 03/006091 | 1/2003 |
| WO | WO 03/023551 | 3/2003 |
| WO | WO 03/050917 | 6/2003 |
| WO | WO 03/091836 | 11/2003 |
| WO | WO 03/094092 | 11/2003 |
| WO | WO 2004/060455 | 7/2004 |
| WO | WO 2004/070557 | 8/2004 |
| WO | WO 2004/070562 | 8/2004 |
| WO | WO 2004/072828 | 8/2004 |
| WO | WO 2005/036447 | 4/2005 |
| WO | WO 2005/057175 | 6/2005 |
| WO | WO 2005/066872 | 7/2005 |
| WO | WO 2007/087443 | 8/2007 |
| WO | WO 2007/117705 | 10/2007 |
| WO | WO 2007/127879 | 11/2007 |
| WO | WO 2007/127880 | 11/2007 |
| WO | WO 2008/059495 | 5/2008 |
| WO | WO 2008/064254 | 5/2008 |
| WO | WO 2008/067245 | 6/2008 |
| WO | WO 2008/082854 | 7/2008 |
| WO | WO 2008/088490 | 7/2008 |
| WO | WO 2008/097316 | 8/2008 |
| WO | WO 2008/103915 | 8/2008 |
| WO | WO 2008/124478 | 10/2008 |
| WO | WO 2008/134146 | 11/2008 |
| WO | WO 2009/016504 | 2/2009 |
| WO | WO 2009/023406 | 2/2009 |
| WO | WO 2009/023407 | 2/2009 |
| WO | WO 2009/023634 | 2/2009 |
| WO | WO 2009/036327 | 3/2009 |
| WO | WO 2009/049252 | 4/2009 |
| WO | WO 2010/017279 | 2/2010 |
| WO | WO 2010/033919 | 3/2010 |
| WO | WO 2010/053703 | 5/2010 |
| WO | WO 2010/075371 | 7/2010 |
| WO | WO 2010/099313 | 9/2010 |
| WO | WO 2010/114929 | 10/2010 |
| WO | WO 2010/119409 | 10/2010 |
| WO | WO 2010/124127 | 10/2010 |
| WO | WO 2010/130992 | 11/2010 |
| WO | WO 2010/135646 | 11/2010 |
| WO | WO 2010/135654 | 11/2010 |
| WO | WO 2010/135686 | 11/2010 |
| WO | WO 2011/005633 | 1/2011 |
| WO | WO 2011/022549 | 2/2011 |
| WO | WO 2012/048833 | 4/2012 |
| WO | WO 2012/049214 | 4/2012 |

(56) References Cited

FOREIGN PATENT DOCUMENTS

| WO | WO 2012/049218 | 4/2012 |
|---|---|---|
| WO | WO 2012/120078 | 9/2012 |
| WO | WO 2012/140547 | 10/2012 |
| WO | WO 2012/164556 | 12/2012 |
| WO | WO 2012/170942 | 12/2012 |
| WO | WO 2013/045506 | 4/2013 |
| WO | WO 2014/100736 | 6/2014 |
| WO | WO 2014/131729 | 9/2014 |
| WO | WO 2014/131730 | 9/2014 |
| WO | WO 2015/047595 | 4/2015 |
| WO | WO 2015/124569 | 8/2015 |
| WO | WO 2016/179389 | 11/2016 |
| WO | WO 2017/200989 | 11/2017 |
| WO | WO 2019/219290 | 11/2019 |
| WO | WO 00/003344 | 1/2020 |
| WO | WO 2020/227403 | 11/2020 |
| WO | WO 2021/201884 | 10/2021 |
| WO | WO 2022/051230 | 3/2022 |
| WO | WO 2023/159134 | 8/2023 |

OTHER PUBLICATIONS

Akridge, Jeannie, "New Pumps Outsmart User Error", Healthcare Purchasing News, Apr. 2011, pp. 10, http://web.archive.org/web/20110426122450/http://www.hpnonline.com/inside/2011-04/1104-OR-Pumps.html.

Alur et al., "Formal Specifications and Analysis of the Computer-Assisted Resuscitation Algorithm (CARA) Infusion Pump Control System", International Journal on Software Tools for Technology Transfer, Feb. 2004, vol. 5, No. 4, pp. 308-319.

Aragon, Daleen RN, Ph.D., CCRN, "Evaluation of Nursing Work Effort and Perceptions About Blood Glucose Testing in Tight Glycemic Control", American Journal of Critical Care, Jul. 2006, vol. 15, No. 4, pp. 370-377.

ASHP Advantage, "Improving Medication Safety in Health Systems Through Innovations in Automation Technology", Proceedings of Educational Symposium and Educational Sessions during the 39th ASHP Midyear Clinical Meeting, Dec. 5-9, 2004, Orlando, FL, pp. 28.

Beard et al., "Total Quality Pain Management: History, Background, Resources", Abbott Laboratories, TQPM Survey History, available Feb. 2015 or earlier, pp. 1-3.

Bektas et al., "Bluetooth Communication Employing Antenna Diversity", Proceedings of Eight IEEE International Symposium on Computers and Communication, Jul. 2003, pp. 6.

Bequette, Ph.D., "A Critical Assessment of Algorithms and Challenges in the Development of a Closed-Loop Artificial Pancreas", Diabetes Technology & Therapeutics, Feb. 28, 2005, vol. 7, No. 1, pp. 28-47.

Bequette, B. Wayne, Ph.D., "Analysis of Algorithms for Intensive Care Unit Blood Glucose Control", Journal of Diabetes Science and Technology, Nov. 2007, vol. 1, No. 6, pp. 813-824.

Braun, "Infusomat® Space and Accessories", Instructions for Use, Nov. 2010, pp. 68. http://corp.bbraun.ee/Extranet/Infusionipumbad/Kasutusjuhendid/Vanad/Kasutusjuhend-Infusomat_Space(vers688J,inglise_k).pdf.

Brownlee, Seth, "Product Spotlight: The Plum A+ with Hospira MedNet Infusion System", PP&P Magazine, Dec. 2005, vol. 2, No. 7, pp. 2.

Cannon, MD et al., "Automated Heparin-Delivery System to Control Activated Partial Thromboplastin Time", Circulation, Feb. 16, 1999, vol. 99, pp. 751-756.

Cardinal Health, "Alaris® Syringe Pumps" Technical Service Manual, Copyright 2002-2006, Issue 9, pp. 1-88, http://www.frankshospitalworkshop.com/equipment/documents/infusion_pumps/service_manuals/Cardinal_Alaris_-_Service_Manual.pdf.

"CareAware® Infusion Management", Cerner Store, as printed May 12, 2011, pp. 3, https://store.cerner.com/items/7.

Chen et al., "Enabling Location-Based Services on Wireless LANs", The 11th IEEE International Conference on Networks, ICON 2003, Sep. 28-Oct. 1, 2003, pp. 567-572.

"Computer Dictionary", Microsoft Press, Third Edition, Microsoft Press, 1997, pp. 430 & 506.

"Context-Free Grammar", Wikipedia.org, as last modified Mar. 5, 2010 in 11 pages, https://en.wikipedia.org/w/index.php/?title=Context-free_grammar&oldid=347915989.

Crawford, Anne J., MSN, RNC, "Building a Successful Quality Pain Service: Using Patient Satisfaction Data and the Clinical Practice Guideline", USA, 1995, pp. 1-6.

Crocker et al., "Augmented BNF for Syntax Specifications: ABNF", Network Working Group, Standards Track, Jan. 2008, pp. 16.

Davidson et al., "A Computer-Directed Intravenous Insulin System Shown to be Safe, Simple, and Effective in 120,618 h of Operation", Diabetes Care, Oct. 2005, vol. 28, No. 10, pp. 2418-2423.

Davies, T., "Cordless Data Acquisition in a Hospital Environment", IEE Colloquium on Cordless Computing—Systems and User Experience, 1993, pp. 4.

Dayhoff et al., "Medical Data Capture and Display: The Importance of Clinicians' Workstation Design", AMIA, Inc., 1994, pp. 541-545.

Diabetes Close Up, Close Concerns AACE Inpatient Management Conference Report, Consensus Development Conference on Inpatient Diabetes and Metabolic Control, Washington, D.C., Dec. 14-16, 2003, pp. 1-32.

Doesburg et al., "Improved Usability of a Multi-Infusion Setup Using a Centralized Control Interface: A Task-Based Usability Test", Aug. 11, 2017, PLoS ONE, vol. 12, No. 8, pp. 10.

"Download", Free On-Line Dictionary of Computing, as archived Jun. 16, 2010 in 1 page, http://web.archive.org/web/20100616010314/https://foldoc.org/download.

East PhD et al., "Digital Electronic Communication Between ICU Ventilators and Computers and Printers", Respiratory Care, Sep. 1992, vol. 37, No. 9, pp. 1113-1122.

Edworthy, Judy, "Medical Audible Alarms: A Review", Journal of the American Medical Informatics Association, vol. 20, No. 3, 2013, pp. 584-589.

Einhorn, George W., "Total Quality Pain Management: A Computerized Quality Assessment Tool for Postoperative Pain Management", Abbott Laboratories, Chicago, IL, Mar. 2, 2000, pp. 1-4.

Eskew et al., "Using Innovative Technologies to Set New Safety Standards for the Infusion of Intravenous Medications", Hospital Pharmacy, 2002, vol. 37, No. 11, pp. 1179-1189.

Felleiter et al., "Data Processing in Prehospital Emergency Medicine", International journal of Clinical Monitoring and Computing, Feb. 1995, vol. 12, No. 1, pp. 37-41.

"File Verification", Wikipedia.org, as last modified Oct. 11, 2011 in 2 pages, https://en.wikipedia.org/w/index.php?title=File_verification&oldid=455048290.

Fogt et al., Development and Evaluation of a Glucose Analyzer for a Glucose-Controlled Insulin Infusion System (Biostator®), Clinical Chemistry, 1978, vol. 24, No. 8, pp. 1366-1372.

Gabel et al., "Camp: A Common API for Measuring Performance", 21st Large Installations System Administration Conference (LISA '07), 2007, pp. 49-61.

Gage et al., "Automated Anesthesia Surgery Medical Record System", International Journal of Clinical Monitoring and Computing, Dec. 1990, vol. 7, No. 4, pp. 259-263.

Galt et al., "Personal Digital Assistant-Based Drug Information Sources: Potential to Improve Medication Safety", Journal of Medical Library Association, Apr. 2005, vol. 93, No. 2, pp. 229-236.

Gardner, Ph.D et al., "Real Time Data Acquisition: Recommendations for the Medical Information Bus (MIB)", 1992, pp. 813-817.

"General-Purpose Infusion Pumps", Health Devices, EXRI Institute, Oct. 1, 2002, vol. 31, No. 10, pp. 353-387.

Givens et al., "Exploring the Internal State of User Interfaces by Combining Computer Vision Techniques with Grammatical Inference", Proceedings of the 2013 International Conference on Software Engineering, San Francisco, CA, May 18-26, 2013, pp. 1165-1168.

Glaeser, "A Hierarchical Minicomputer System for Continuous Post-Surgical Monitoring", Computers and Biomedical Research, Aug. 31, 1975, pp. 336-361.

(56) References Cited

OTHER PUBLICATIONS

Goldberg et al., "Clinical Results of an Updated Insulin Infusion Protocol in Critically III Patients", Diabetes Spectrum, 2005, vol. 18, No. 3, pp. 188-191.
Gomez et al., "CLAM: Connection-Less, Lightweight, and Multiway Communication Support for Distributed Computing", Computer Science, 1997, vol. 1199, pp. 227-240.
"GPS Tracker for Medical Equipment", http://www.trackingsystem.com/forbusinesses/corporate-trackingsystem/1098-gps-tracker-formedicalequipment.html, Mar. 15, 2015, pp. 2.
Graseby, "Model 3000/500 and Micro 3100/505: Volumetric Infusion Pump", Technical Service Manual, Graseby Medical Ltd., Apr. 2002, Issue A, pp. 160.
Graseby, "Model 3000/500 and Micro 3100/505: Volumetric Infusion Pump: Illustrated Parts List for Pump Serial Numbers from 3000 to 59,999", Technical Service Manual, Graseby Medical Ltd., Apr. 2002, Issue A, pp. 71.
Halpern et al., "Changes in Critical Care Beds and Occupancy in the United States 1985-2000: Differences Attributable to Hospital Size", Critical Care Medical, Aug. 2006, vol. 34, No. 8, pp. 2105-2112.
Hamann et al., "PUMPSIM: A Software Package for Simulating Computer-Controlled Drug Infusion Pumps", Annual International Conference of the IEEE Engineering in Medicine and Biology Society, 1990, vol. 12, No. 5, pp. 2019-2020.
Hasegawa et al., "On a Portable Memory Device for Physical Activities and Informations of Maternal Perception", Journal of Perinatal Medicine, 1988, vol. 16, No. 4, pp. 349-356.
Hawley et al., "Clinical Implementation of an Automated Medical Information Bus in an Intensive Care Unit", Proceedings of the Annual Symposium on Computer Application in Medical Care, Nov. 9, 1988, pp. 621-624.
Hayes-Roth et al., "Guardian: A Prototype Intelligent Agent for Intensive-Care Monitoring", Artificial Intelligence in Medicine, vol. 4, Dec. 31, 1992, pp. 165-185.
Hospira, GemStar® Pain Management Infusion System 9-084-PR1-2-2, www.hospira.com/products/gemstar_painmanagement.aspx, Jan. 28, 2010, pp. 1-2.
Huang et al., "Secure Identity-Based Data Sharing and Profile Matching for Mobile Healthcare Social Networks in Cloud Computing", vol. 6, Jul. 2018, pp. 36584-36594.
International Search Report and Written Opinion received in PCT Application No. PCT Application No. PCT/US2021/048262, dated Dec. 8, 2021 in 7 pages.
Introducing Abbott TQPM (Total Quality Pain Management), Abbott Laboratories, Abbott Park, IL, May 2000, pp. 1-4.
"Infusion Pump", Wikipedia.org, as last modified Mar. 27, 2014, in 3 pages, https://web.archive.org/web/20140703024932/https://en.wikipedia.org/wiki/Infusion_pump.
Isaka et al., "Control Strategies for Arterial Blood Pressure Regulation", IEEE Transactions on Biomedical Engineering, Apr. 1993, vol. 40, No. 4, pp. 353-363.
Johnson et al., "Using BCMA Software to Improve Patient Safety In Veterans Administration Medical Centers", Journal of Healthcare Information Management, Dec. 6, 2004, vol. 16, No. 1, pp. 46-51.
Kent Displays, "Reflex™ Electronic Skins", Product Brief 25127B, 2009, pp. 2.
Kent Displays, "Reflex Electronic Skins Engineering Evaluation Kit", 25136A, Mar. 10, 2009.
Lefkowitz et al., "A Trial of the Use of Bar Code Technology to Restructure a Drug Distribution and Administration System", Hospital Pharmacy, Mar. 31, 1991, vol. 26, No. 3, pp. 239-242.
Lenssen et al., "Bright Color Electronic Paper Technology and Applications", IDS '09 Publication EP1-2 (Phillips Research), 2009, pp. 529-532.
Leveson, Nancy, "Medical Devices: The Therac-25", Appendix A, University of Washington, 1995, pp. 49.
Linkens, D.A. "Computer Control for Patient Care", Computer Control of Real-Time Processes, IEE Control Engineering Series 41, 1990, Ch. 13, pp. 216-238.

Mako Hill et al., "The Official Ubuntu Book", Shoeisha Co., Ltd., 1st Edition, Jun. 11, 2007, pp. 115 to 125.
Marshall, et al., "New Microprocessor-Based Insulin Controller", IEEE Transactions on Biomedical Engineering, Nov. 1983, vol. BME-30, No. 11, pp. 689-695.
Martino et al., "Automation of a Medical Intensive Care Environment with a Flexible Configuration of Computer Systems", Proceedings of the Annual Symposium on Computer Application in Medical Care, Nov. 5, 1980, vol. 3, pp. 1562-1568.
Matsunaga et al., "On the Use of Machine Learning to Predict the Time and Resources Consumed by Applications", 2010 10th IEEE/ACM International Conference on Cluster, Cloud and Grid Computing (CCGrid), May 17-20, 2010, pp. 495-504.
Mauseth et al., "Proposed Clinical Application for Tuning Fuzzy Logic Controller of Artificial Pancreas Utilizing a Personalization Factor", Journal of Diabetes Science and Technology, Jul. 2010, vol. 4, No. 4, pp. 913-922.
"McKesson Automation and ALARIS Medical Systems Developing Point-of-Care Bar Coding Solution to Improve IV Medication Safety", PR Newswire, NY, Dec. 9, 2002, pp. 4.
Medfusion™, "Medfusion Syringe Infusion Pump Model 4000", Operator's Manual, Software Version V1.1, Sep. 2011, pp. 154. http://www.medfusionpump.com/assets/literature/manuals/Operators_Manual_4000_40-5760-51A.pdf.
Metnitz et al., "Computer Assisted Data Analysis in Intensive Care: the ICDEV Project-Development of a Scientific Database System for Intensive Care", International Journal of Clinical Monitoring and Computing, Aug. 1995, vol. 12, No. 3, pp. 147-159.
Michienzi, Kelly, "Managing Drug Library Updates", Pharmacy Purchasing Products, https://www.pppmag.com/article/1061, Feb. 2012, vol. 9, pp. 22-23.
Micrel Medical Devices, "MP Daily +" http://web.archive.org/web/20130803235715/http://www.micrelmed.com/index.aspx?productid=9 as archived Aug. 3, 2013 in 1 page.
Moghissi, Etie, MD, FACP, FACE, "Hyperglycemia in Hospitalized Patients", A Supplement to ACP Hospitalist, Jun. 15, 2008, pp. 32.
Murray, Jr. et al., "Automated Drug Identification System (during surgery)", IEEE Proceedings of Southeastcon '91, Apr. 7-10, 1991, pp. 265.
Nicholson et al., "'Smart' Infusion Apparatus for Computation and Automated Delivery of Loading, Tapering, and Maintenance Infusion Regimens of Lidocaine, Procainamide, and Theophylline", Proceedings of The Seventh Annual Symposium on Computer Applications in Medical Care, Oct. 1983, pp. 212-213.
Nolan et al., "The P1073 Medical Information Bus Standard: Overview and Benefits for Clinical Users", 1990, pp. 216-219.
Omnilink Systems, Inc., "Portable Medical Equipment Tracking", http://www.omnilink.com/portablemedicalequipmenttracking/, Mar. 15, 2015, pp. 2.
O'Shea, Kristen L., "Infusion Management: Working Smarter, Not Harder", Hospital Pharmacy, Apr. 2013, vol. 48, No. 3, pp. S1-S14.
Package Management in Debian GNU/Linux, Debian GNU/Linux Expert Desktop Use Special, Giutsu-Hyohron Co., Ltd., First Edition, Sep. 25, 2004, pp. 183-185.
Passos et al., "Distributed Software Platform for Automation and Control of General Anaesthesia", Eighth International Symposium on Parallel and Distributed Computing, ISPDC '09, Jun. 30-Jul. 4, 2009, pp. 8.
Philips, "IntelliSpace Event Management and IntelliVue Patient Monitoring", Release 10, 2011, http://incenter.medical.philips.com/doclib/enc/fetch/2000/4504/577242/577243/577247/582646/583147/8359175/Philips_Patient_Monitoring_and_IntelliSpace_Event_Management_Interoperability.pdf%3fnodeid%3d8508574%26vernum%3d-2, pp. 2.
Pretty et al., "Hypoglycemia Detection in Critical Care Using Continuous Glucose Monitors: An in Silico Proof of Concept Analysis", Journal of Diabetes Science and Technology, Jan. 2010, vol. 4, No. 1, pp. 15-24.
Rappoport, Arthur E., "A Hospital Patient and Laboratory machine-Readable Identification System (MRIS) Revisited", Journal of Medical Systems, Apr. 1984, vol. 8, Nos. 1/2, pp. 133-156.

(56) References Cited

OTHER PUBLICATIONS

Ritchie et al., "A Microcomputer Based Controller for Neuromuscular Block During Surgery", Annals of Biomedical Engineering, Jan. 1985, vol. 13, No. 1, pp. 3-15.
Saager et al., "Computer-Guided Versus Standard Protocol for Insulin Administration in Diabetic Patients Undergoing Cardiac Surgery", Annual Meeting of the American Society of Critical Care Anesthesiologists, Oct. 13, 2006.
Sanders et al., "The Computer in a Programmable Implantable Medication System (PIMS)", Proceedings of the Annual Symposium on Computer Application in Medical Care, Nov. 2, 1982, pp. 682-685.
Schilling et al., "Optimizing Outcomes! Error Prevention and Evidence-Based Practice with IV Medications", A Pro-Ce Publication, Hospira, Inc., Feb. 6, 2012, pp. 56.
Schulze et al., "Advanced Sensors Technology Survey", Final Report, Feb. 10, 1992, pp. 161.
Scott, et al., "Using Bar-Code Technology to Capture Clinical Intervention Data in a Hospital with a Stand-Alone Pharmacy Computer System", Mar. 15, 1996, American Journal of Health-System Pharmacy, vol. 53, No. 6, pp. 651-654.
Sebald et al., "Numerical Analysis of a Comprehensive in Silico Subcutaneous Insulin Absorption Compartmental Model", 31st Annual International Conference of the IEEE Engineering in Medicine and Biology Society, Sep. 2-6, 2009, pp. 3901-3904.
Shabot, M. Michael, "Standardized Acquisition of Bedside Data: The IEEE P1073 Medical Information Bus", International Journal of Clinical Monitoring and Computing, vol. 6, Sep. 27, 1989, pp. 197-204.
Sheppard, Louis, Ph.D., "Automation of the Infusion of Drugs Using Feedback Control", Journal of Cardiothoracic and Vascular Anesthesia, Feb. 28, 1989, vol. 3, No. 1, pp. 1-3.
Sheppard, Louis, Ph.D., "Computer Control of the Infusion of Vasoactive Drugs", Annals of Biomedical Engineering, Jul. 1980, vol. 8, No. 4-6, pp. 431-444.
Sheppard, Louis, Ph.D., "The Application of Computers to the Measurement, Analysis, and Treatment of Patients Following Cardiac Surgical Procedures", The University of Alabama in Birmingham, Oct. 31, 1977, pp. 297-300.
Sheppard, Louis, Ph.D., "The Computer in the Care of Critically III Patients", Proceedings of the IEEE, Sep. 1979, vol. 67, No. 9, pp. 1300-1306.
"Sigma Spectrum: Operator's Manual", Oct. 2009, pp. 72. http://static.medonecapital.com/manuals/userManuals/Sigma-Spectrum-Operator-Manual-October-2009.pdf.
Simonsen, Michael Ph.D., POC Testing, New Monitoring Strategies on Fast Growth Paths in European Healthcare Arenas, Biomedical Business & Technology, Jan. 2007, vol. 30, No. 1, pp. 1-36.
Siv-Lee et al., "Implementation of Wireless 'Intelligent' Pump IV Infusion Technology in a Not-for-Profit Academic Hospital Setting", Hospital Pharmacy, Sep. 2007, vol. 42, No. 9, pp. 832-840. http://www.thomasland.com/hpj4209-832.pdf.
Slack, W.V., "Information Technologies for Transforming Health Care", https://www.andrew.cmu.edu/course/90-853/medis.dir/otadocs.dir/03ch2.pdf, Ch. 2, 1995, pp. 29-78.
Smith, Joe, "Infusion Pump Informatics", CatalyzeCare: Transforming Healthcare, as printed May 12, 2011, pp. 2.
Sodders, Lisa, "VA Center Keeps Medicine in Right Hands", The Capital-Journal, Dec. 4, 1999, pp. 1-2.
"Software Versioning", Wikipedia.org, dated Oct. 16, 2011 in 11 pages, https://en.wikipedia.org/w/index.php?title=Software_versioning&oldid=455859110.
Stitt, F.W., "The Problem-Oriented Medical Synopsis: a Patient-Centered Clinical Information System", Proceedings of the Annual Symposium on Computer Application in Medical Care, 1994, pp. 88-92.
Stokowski, Laura A. RN, MS, "Using Technology to Improve Medication Safety in the Newborn Intensive Care Unit", Advances in Neonatal Care, Dec. 2001, vol. 1, No. 2, pp. 70-83.
Sutton et al., "The Syntax and Semantics of the PROforma Guideline Modeling Language", Journal of the American Medical Informatics Association, Sep./Oct. 2003, vol. 10, No. 5, pp. 433-443.
Szeinbach et al., "Automated Dispensing Technologies: Effect on Managed Care", Journal of Managed Care Pharmacy (JMCP), Sep./Oct. 1995, vol. 1, No. 2, pp. 121-127.
Szolovits et al., "Guardian Angel: Patient-Centered Health Information Systems", Technical Report MIT/LCS/TR-604, Massachusetts Institute of Technology Laboratory for Computer Science, May 1994, pp. 39.
Van Den Berghe, M.D., Ph.D., et al., "Intensive Insulin Therapy in Critically III Patients", The New England Journal of Medicine, Nov. 8, 2001, vol. 345, No. 19, pp. 1359-1367.
Van Den Berghe, M.D., Ph.D., et al., "Intensive Insulin Therapy in the Medical ICU", The New England Journal of Medicine, Feb. 2, 2006, vol. 354, No. 5, pp. 449-461.
Van Der Maas et al., "Requirements for Medical Modeling Languages", Journal of the American Medical Informatics Association, Mar./Apr. 2001, vol. 8, No. 2, pp. 146-162.
Villalobos et al., "Computerized System in Intensive Care medicine", Medical Informatics, vol. 11, No. 3, 1986, pp. 269-275.
Wilkins et al., "A Regular Language: The Annotated Case Report Form", PPD Inc., PharmaSUG2011—Paper CD18, 2011, pp. 1-9.
Ying et al., "Regulating Mean Arterial Pressure in Postsurgical Cardiac Patients. A Fuzzy Logic System to Control Administration of Sodium Nitroprusside", IEEE Engineering in Medicine and Biology Magazine, vol. 13, No. 5, Nov.-Dec. 1994, pp. 671-677.
Yue, Ying Kwan, "A Healthcare Failure Mode and Effect Analysis on the Safety of Secondary Infusions", Thesis, Institute of Biomaterials and Biomedical Engineering, University of Toronto, 2012, pp. 168.
Yurkonis et al., "Computer Simulation of Adaptive Drug Infusion", IEEE Transactions on Biomedical Engineering, vol. BME-34, No. 8, Aug. 1987, pp. 633-635.
Zakariah et al., "Combination of Biphasic Transmittance Waveform with Blood Procalcitonin Levels for Diagnosis of Sepsis in Acutely III Patients", Critical Care Medicine, 2008, vol. 36, No. 5, pp. 1507-1512.
Bellare et al., "Security Proofs for Identity-Based Identification and Signature Schemes", Lecture Notes in Computer Science, Jan. 2009, vol. 22, No. 1, pp. 18.
Block, Alexander, "Secret Sharing and 1-11 Threshold Signatures with BLS", Jul. 2, 2018, https://blog.dash.org/secret-sharing-and-threshold-signatures-with-bls-954d1587b5f, in 8 pages.
Gutwin et al., "Gone But Not Forgotten: Designing for Disconnection in Synchronous Groupware", CSCW 2010, Feb. 6-10, 2010, Savannah, Georgia, USA., pp. 179-188.
Li et al., "Hijacking an Insulin Pump: Security Attacks and Defenses for a Diabetes Therapy System", 2011 IEEE 13th International Conference on e-Health Networking, Applications and Services, 2011, pp. 150-156.
Murphy, Robert, "The Design of Safety-Critical Medical Infusion Devices", May 30, 2007, Doctor of Philosophy submission, pp. 317.
Nojoumian et al., "Social Secret Sharing in Cloud Computing Using a New Trust Function", 2012 Tenth Annual International Conference on Privacy, Security and Trust, pp. 161-167.
Rahmani et al., "Smart e-Health Gateway: Bringing Intelligence to Internet-of-Things Based Ubiquitous Healthcare Systems", 2015 12th Annual IEEE Consumer Communications and Networking Conference (CCNC), Jul. 2015, pp. 826-834.
Sethia et al., "Security Framework for Portable NFC Mobile Based Health Record System", Oct. 2016, IEEE 12th International Conference on Wireless and Mobile Computing, Networking and Communications, pp. 1-8.
"Sigma Spectrum: Operator's Manual", May 15, 2008, pp. 63. <https://usme.com/content/manuals/sigma-spectrum-operator-manual.pdf>.
Solapurkar et al., "Building Secure Healthcare Services Using OAuth 2.0 and JSON Web Token in IOT Cloud Scenario", Dec. 2016, 2nd International Conference on Contemporary Computing and Informatics, pp. 99-10.
"TCG TPM v2.0 Provisioning Guidance", Reference, Version 1, Revision 1, Mar. 15, 2017, pp. 1-43.

(56) References Cited

OTHER PUBLICATIONS

Yoo et al., "Code-Based Authentication Scheme for Lightweight Integrity Checking of Smart Vehicles", IEEE Access, 2018, vol. 6, pp. 46731-46741.

* cited by examiner

IDENTITY-BASED SECURE MEDICAL DEVICE COMMUNICATIONS

CROSS-REFERENCE TO RELATED APPLICATIONS

The present application is a continuation of PCT Application No. PCT/US2021/048262, filed on Aug. 30, 2021 and titled "Identity-Based Secure Medical Device Communications," which claims priority to Indian Provisional Patent Application Number 202011038396, filed on Sep. 5, 2020 and titled "Identity-Based Secure Medical Device Communications," and U.S. Provisional Patent Application No. 63/108,141, filed on Oct. 30, 2020 and titled "Identity-Based Secure Medical Device Communications," the contents of each of which are incorporated by reference herein and made part of this specification.

TECHNICAL FIELD

This disclosure relates to the field of medical device management, and particularly to systems and methods for secure use of medical devices.

BACKGROUND

Electronic medical devices often have processors and other computing components. Such medical devices may execute software and communicate with other computing systems via a network. Secure network communication may involve the encryption of communications transmitted from a medical device and/or decryption of communications received by the medical device. For example, a processor of the medical device may execute encryption/decryption operations on data to be transmitted via or received via the network.

SUMMARY

Various techniques for managing the operation of devices using identity-based cryptography are described herein. These techniques may include provisioning a master public key to each system that will communicate with a medical device using device-identifier specific cryptography. A master secret key is provisioned in a trusted processor of the medical device, and the medical device provisions its own device identifier-specific secret key using the master secret key. This setup facilitates several management features, including automatic initial configuration, signed logging, signed backup files, and secure binding of medication containers to the medical device. These and other embodiments are described in greater detail below with reference to FIGS. 1-9. Although many of the examples are described in the context of medical devices, functions, and environments (including infusion pumps, medication dispensing functions, and hospital or clinical environments), the techniques described herein can be applied to other types of devices, functions, and environments.

BRIEF DESCRIPTION OF DRAWINGS

Throughout the drawings, reference numbers may be re-used to indicate correspondence between referenced elements. The drawings are provided to illustrate example embodiments described herein and are not intended to limit the scope of the disclosure.

DETAILED DESCRIPTION OF ILLUSTRATIVE EMBODIMENTS

Figure 1:
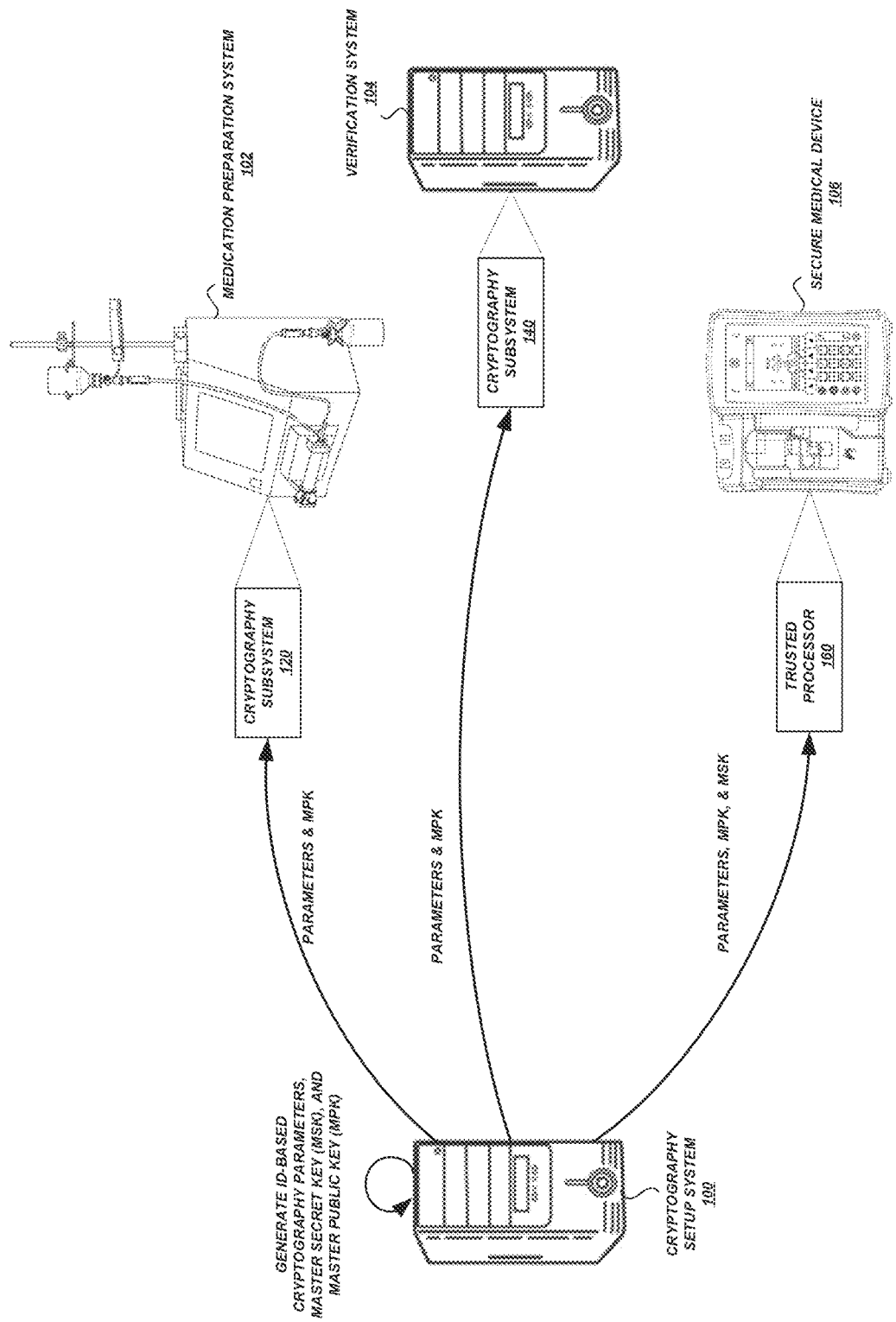
FIG. 1 is a block diagram of an example cryptography setup system, medication preparation system, verification system, and secure medical device according to some embodiments.

The present disclosure is directed to secure management of medical device communications using device identity-based encryption. A group of medical devices may each include a trusted processor in which the same master secret cryptographic key has been provisioned. The trusted processor is "trusted" in the sense that the master secret key is not accessible from outside of the trusted processor, and therefore the trusted processor may encrypt and decrypt data without exposing the master secret key. To generate a device identifier-specific secret cryptographic key for a medical device, the trusted processor executing within the medical device may use the master secret key and a device identifier uniquely associated with the medical device. Like the master secret key, each medical device stores their own device identifier-specific secret key such that it is not accessible from outside the trusted processor. Other devices and systems can communicate with a particular medical device using the device identifier for that medical device and a master public cryptographic key. The master public key is associated with the master secret key that has been provisioned in the trusted processors of each medical device. The master public key is also well-known or otherwise not kept secret among the devices and systems that communicate with the medical devices. Communications to a particular medical device can be encrypted using the device's identifier and the master public key such that only the device in possession of the device identifier-specific secret key generated using the same device identifier can decrypt the messages. Thus, other medical devices with different device identifiers cannot successfully decrypt the messages that have been encrypted using the device identifier, and devices that do not have access to the master secret key cannot derive the device identifier-specific secret key necessary to decrypt messages that are encrypted using the device identifier and master public key. In a similar manner, the medical device can sign, encrypt, and perform other cryptographic functions with the device identifier-specific secret key to ensure the authenticity of certain data, such as log files, backup files, and the like.

Some existing methods of secure communication require participating devices to exchange or agree on cryptographic keys. This pre-communication process may introduce a delay in the communications, and may expose the cryptographic keys to third parties thereby compromising the security of the communications. Identity-based encryption addresses some of these issues by deriving identifier-specific secret keys from a master secret key. In order to communicate securely with a particular device, a party need only know the identifier of the device and have access to the master public key that corresponds to the master secret key from which the identifier-specific secret key was derived. However, the device associated with the identifier must obtain the identifier-specific secret key for the device from a key generator. This may require network connection and communication with the key generator, and may expose the identifier-specific secret key during transmission. Moreover, even after the identifier-specific secret key is obtained by the device, it may be exposed to non-secure components of the device or to outside devices.

Some aspects of the present disclosure address the issues noted above, among others, by including a trusted processor in the medical devices for which device identifier-specific secret keys are generated. Within a particular medical device, the trusted processor may store the master secret key such that it is not accessible outside of the trusted processor. Moreover, the trusted processor may be configured to generate a device identifier-specific secret key for the medical device using the master secret key and a device identifier for the device. Thus, by including a trusted processor configured in this manner, the medical device effectively includes its own secret key generator and can self-provision a device identifier-specific secret key without requiring any communication with a separate secret key generator. Moreover, the device identifier may be any token that uniquely (or substantially uniquely) identifies the device, such as a serial number. Therefore, any number of medical devices may be manufactured with trusted processors and provisioned with the same master secret key. When deployed, each of the medical devices can self-provision their own unique device identifier-specific secret key that can be used to conduct secure communications and other secure data operations as described herein.

Additional aspects of the present disclosure relate to using device identifier-specific cryptography to verify the identity of a device. A verification system can initiate a procedure to verify the identity of a particular medical device by sending to the medical device verification data (e.g., a randomly-generated nonce) that has been encrypted using the medical device's identifier and the master public key. If the medical device successfully decrypts the verification data and sends it back to the verification system, then the medical device has proven that it has the device identifier-specific secret key that corresponds to the device identifier used to encrypt the data. In some embodiments, the verification system may send unencrypted verification data to the medical device, and the medical device may sign the verification data with its device identifier-specific secret key and return the signed verification data to the verification system. The verification system can then verify the signed verification data by decrypting it using the medical device's identifier and the master public key. In either implementation, the medical device may be considered to have proven its identity to the verification system assuming the following preconditions are satisfied: (1) the master secret key is not available outside of any of the medical devices' trusted processors, and (2) the trusted processors each self-provision their own device identifier-specific secret key based on the master secret key and their unique device identifier.

Further aspects of the present disclosure relate to using device identifier-specific cryptography to ensure medication is administered by only the specific medical device to which it is assigned. A medication preparation system may generate control data to assign a medication container to a specific medical device. The control data may be generated using the master public key and the device identifier for the medical device to which the medication container is to be assigned. The control data may be associated with the medication container such that it can be accessed by the medical device for authorization prior to administration. For example, the control data may be encoded into a visually reproducible and automatically readable form (e.g., a barcode on a label that is applied to the medication container) or encoded into electronic medium (e.g., a radio frequency identification or "RFID" tag of the medication container). Only the medical device to which the medication container has been assigned may decrypt the control data using the device identifier-specific secret key. Successful decryption and verification of the contents of the control data (e.g., medication identifier, patient identifier, device identifier, other data, or some combination thereof) may be required in order for the medical device to be operated to administer medication from the medication container.

Still further aspects of the present disclosure relate to using device identity-based cryptography to ensure the authenticity of medical device data, such as logs, backup files, and the like. A medical device may generate data regarding operation of the medical device, such as data regarding each medication administration procedure, each identification verification procedure, or the like. Such data may be logged for use in analyzing issues, such as those involving medication administered by the device (e.g., to detect overrides, administration irregularities, errors, and the like). In order to ensure the authenticity of such log data, the medical device may sign the log data using the device identifier-specific secret key. This signature may then be verified by any other system that has access to the master public key and the device identifier of the medical device. Successful verification of the signed log data ensures that the medical device associated with the device identifier is the source of the log data, and that the log data has not been altered after being signed by the medical device. A similar process may be used to encrypt or sign backup files, such as configuration backup files.

Additional aspects of the present disclosure relate to using identity-based cryptography to securely configure a medical device. An initial configuration system may provide a network connection—such as a Wi-Fi connection—to medical devices. In some embodiments, the medical devices may be configured to, upon initial startup after deployment, connect to the initial configuration system by default. When a medical device connects to the initial configuration system, the initial configuration system may begin an identity verification protocol. If the medical device proves its identity, then the initial configuration system may provide a configuration file to the medical device. The configuration file may include various configuration information to be used by the medical device, such as network connectivity information. In this way, medical devices can be automatically configured in a secure, verified manner.

Various aspects of the disclosure will now be described with regard to certain examples and embodiments, which are intended to illustrate but not limit the disclosure. Although aspects of some embodiments described in the disclosure will focus, for the purpose of illustration, on particular examples of medical devices, cryptographic key generation algorithms, and the like, the examples are illustrative only and are not intended to be limiting. In some embodiments, the systems and methods described herein may be applied to additional or alternative medical devices, cryptographic algorithms, etc.

Overview of Example Setup Environment

FIG. 1 illustrates an example environment in which a cryptography setup system 100 conducts a setup process to provision cryptographic keys, parameters, and the like to various devices that will be deployed in a network environment. As shown, the devices that are set up by the cryptography setup system 100 may include (but are not limited to) a medication preparation system 102, a verification system 104, and a secure medical device 106. Illustratively, the devices may be set up to be deployed in one or more healthcare facilities (e.g., hospitals) in which the secure medical device 106 is a medication administration device configured to administer medication prepared by the medication preparation system 102. In such an implementation, the verification system 104 may be (or be part of) an in-facility cloud-based system to manage use of the secure medical device 106, medication preparation system 102, etc. Although only one instance of a medication preparation system 102, verification system 104, and secure medical device 106 are shown in FIG. 1, in practice any number or combination of devices and systems may be set up by the cryptography setup system 100 and deployed to a network environment. For example, a single health care facility may have dozens, hundreds, or more individual secure medical devices 106 and/or medication preparation systems 102. The secure medical devices 106 may be the same as or different than each other, and the medication preparation systems 102 may be the same as or different than each other.

In some embodiments, the cryptography setup system 100 (also referred to simply as the "setup system") may communicate with the medication preparation system 102, verification system 104, and secure medical device 106 via a communication network (also referred to simply as a "network"). The network may be a publicly-accessible network of linked networks, possibly operated by various distinct parties, such as the Internet. In some cases, the network may be or include a private network, personal area network, local area network, wide area network, global area network, cable network, satellite network, cellular data network, etc., or a combination thereof, some or all of which may or may not have access to and/or from the Internet. A medical device manufacturer, distributor, administrator, or other entity may operate the setup system 100 as described in greater detail below to provision cryptographic keys, cryptography algorithm parameters, and the like to the various systems and devices that are to be deployed. The cryptography setup system 100 may be a single physical computing device or logical association of multiple computing devices.

To perform the setup operation for devices to be deployed to a particular network environment, the cryptography setup system 100 may generate a set of data elements, including identity-based cryptography parameters, a master secret key, and a master public key. These data elements, once deployed, can be used to encrypt and decrypt data communicated between the devices that have been set up. More specifically, the encryption and decryption operations may be identity-based cryptographic operations that are based on an identifier of a particular device that is performing encryption or is to perform decryption. This feature ties the encryption/decryption operations to specific device identifiers, and therefore ties the operations to specific devices. For example, the cryptography parameters and master public key may be used with a device identifier to encrypt data that is sent to the device associated with the device identifier. The data encrypted in this manner may only be decrypted using a device identifier-specific secret key that has been generated using the same device identifier and parameters, and also the master secret key. A device that does not have access to the device identifier-specific secret key will therefore be unable (for practical purposes) to successfully decrypt the data. This aspect of device identifier-specific cryptography allows implementation of various identity verification and function authorization features as described in greater detail herein.

Table 1 below provides abbreviations that will be used herein for ease of description:

TABLE 1

Abbreviations

DID: device identifier
DISK: device identifier-specific secret key
MSK: master secret key
MPK: master public key
Params: identity-based cryptography parameters other than keys In one specific, non-limiting embodiment, the cryptography setup system 100 may generate the params, MSK, and MPK using an algorithm such as that described in ISO/IEC 18033-5: 2015, which is incorporated by reference herein. An example implementation is set forth in Table 2 below:

TABLE 2

Generation of Parameters and Master Keys

Establish base groups $G_1$, $G_2$, $G_3$ and a pairing e: $G_1 \times G_2 \rightarrow G_3$, where $G_1$ and $G_2$ are in the form $E(GF(q))[p]$ (an Elliptic curve over a finite Galois Field of order p), where $G_3$ is a multiplicative group of order p, where e is a bilinear pairing that maps two elements from $G_1$ and $G_2$ to $G_3$, and where p and q are primes
Select a random generator Q in $G_2$, where Q is a primitive element in $G_2$
Generate the params as {Q, $G_1$, $G_2$, $G_3$, e}
Generate a random MSK in $Z^*_p$, where $Z^*_p$ is the set of integers [1 to p − 1])
Generate the corresponding MPK as Q (MSK)

The medication preparation system 102, verification system 104, and secure medical device 106 may include various computing components, such as processors, network interface cards, volatile memory, long term storage, input/output components, displays, and the like. These systems and devices may also include components for performing device identity-based cryptography. For example, the medication preparation system 102 may include an identity-based cryptography subsystem 120, the verification system 104 may include an identity-based cryptography subsystem 140, and the secure medical device 106 may include a trusted processor 160. The identity-based cryptography subsystems 120, 140 may also be referred to simply as cryptography subsystems 120, 140, respectively. The cryptography subsystems 120, 140 and trusted processor 160 may be configured to perform cryptography using parameters and keys provided by the setup system 100.

As shown in FIG. 1, the setup system 100 may provide the parameters and MPK to the cryptography subsystems 120, 140 of the medication preparation system(s) 102 and/or verification system(s) 104, respectively. Due to the public nature of the MPK and the inability to decrypt data without a DISK that corresponds to the DID used to encrypt the data, the params and MPK may be made well-known to all devices that participate in identity-based cryptography communications. As long as the MSK and DISKs are kept secure, there may be no need for special security measures to maintain the parameters and MPK within the various devices.

The setup system 100 can also provide the parameters and MPK to the trusted processor 160 of each medical device 106 that is to be deployed in the same environment as the medication preparation system(s) 102 and/or verification system(s) 104. In addition, the setup system 100 can provide the MSK to the trusted processor 160 of each medical device 106. The trusted processor 160 may be implemented as a secure processor or a secure component of another processor. The trusted processor 160 is considered "secure" in the sense that it guarantees, for practical purposes, that the data stored inside is protected and not accessible from outside of the trusted processor 160. Thus, the MSK—and the DISK, once it is provisioned—in the trusted processor 160 are not accessible from outside the trusted processor 160, providing security for identity-based cryptography operations. The trusted processor 160 uses the DISK to generate output (e.g., output of an encryption/decryption operation). The output is provided to other portions of the secure medical device 106 or to other devices without exposing the DISK used to generate the output.

In some embodiments, the trusted processor 160 is a trusted platform module ("TPM") that is a discrete hardware processor specifically designed to perform cryptographic operations. The TPM is physically isolated from the rest of the processing system of the secure medical device 106. For example, the TPM may be implemented on a discrete integrated circuit separate from other processing components of the secure medical device 106 (e.g., separate from the central processing unit and memory). In some embodiments, the trusted processor is a trusted execution environment ("TEE") that is a component of a processor chipset (e.g., the chipset of the central processing unit). The TEE is therefore not physically isolated from the rest of the chipset, but may nevertheless be logically isolated such that access to data within the TEE is restricted.

Because each secure medical device 106 receives the MSK, each secure medical device 106 can dynamically self-provision their own DISK at a later time. As a result, secure medical devices 106 may be deployed without DISKs, and can self-provision their DISKs upon initial startup, as needed, or at some other time without requiring any additional data. Advantageously, this allows multiple medical devices to be deployed into an environment, potentially at different times, and without DISKs. These medical devices are nevertheless able to participate in identity-based cryptographic operations once they self-provision their own DISKs, and other systems and devices need only have access to the MPK and the publically-available DIDs of the medical devices.

Figure 2:
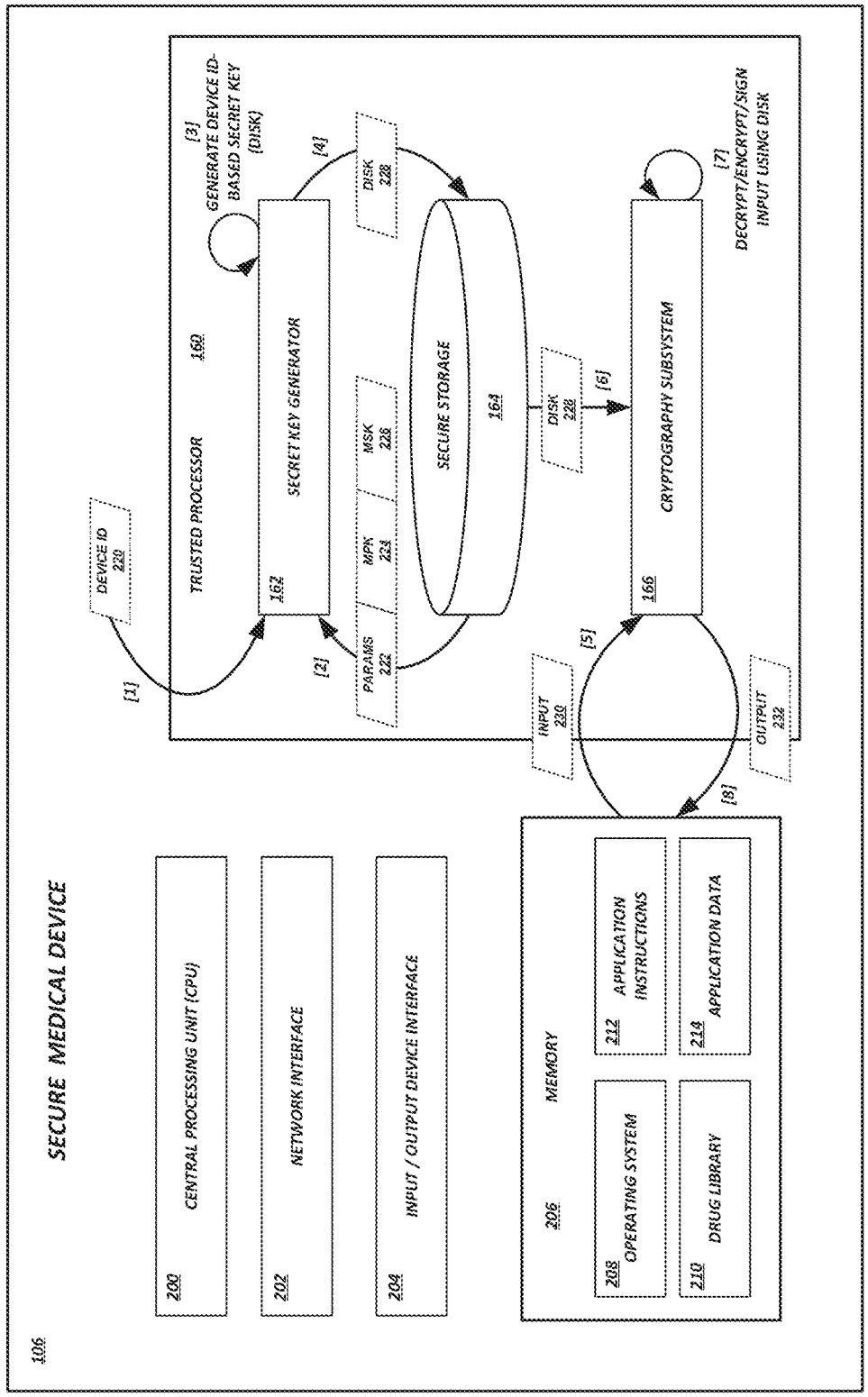
FIG. 2 is a block diagram illustrating data flows and processing performed by components of a secure medical device during a secret key generation procedure according to some embodiments.

FIG. 2 illustrates an example of a secure medical device 106 showing interactions between various internal components of the secure medical device 106 to self-provision a DISK, and subsequent use of the DISK in identity-based cryptography operations. In some embodiments, as shown, the secure medical device 106 may include: one or more computer processors 200, such as physical central processing units ("CPUs"); one or more network interfaces 202, such as a network interface cards ("NICs"); one or more input/output device interfaces 204, and one or more computer readable memories 206, such as random access memory ("RAM") and/or other non-transitory computer-readable media. The computer readable memory 206 may include computer program instructions that the computer processor 200 executes in order to implement one or more embodiments. For example, the computer readable memory 206 can store an operating system 208 that provides computer program instructions for use by the computer processor 200 in the general administration and operation of the secure medical device 106. The computer readable memory 206 may also include a drug library 210 with data regarding medications that may be administered using the secure medical device 106. The computer readable memory 206 may also include application instructions 212 and application data 214 for implementing medication administration operations, logging operations, and the like.

In some embodiments, the secure medical device 106 may be or include an infusion pump with various components to perform infusion pump operations. For example, an infusion pump may include a motor controller unit ("MCU") configured to control a motor (not shown) that dispenses medication.

The secure medical device 106 includes a trusted processor 160. Although the trusted processor 160 is shown in FIG. 2 as being physically separate from other components of the secure medical device 106, in some embodiments the trusted processor 160 may be implemented as a discrete component of another processor as described above. The trusted processor 160 may include various physical or logical components. In some embodiments, as shown, the trusted processor 160 may include a secret key generator 162 to generate a DISK. The secret key generator 162 may be implemented in hardware, or as a combination of software and hardware to execute the software. The trusted processor 160 may include a secure storage 164 to store the parameters and keys used by the trusted processor 160. In some embodiments, the secure storage 164 may be a non-volatile secure element that stores the parameters and keys persistently, even after the medical device 106 is powered off. The trusted processor 160 may also include an identity-based cryptography subsystem 166 to perform identity-based cryptographic operations using the parameters and keys stored in the secure storage 164. The identity-based cryptography subsystem may be referred to simply as a cryptography subsystem 166. The cryptography subsystem 166 may be implemented in hardware, or as a combination of software and hardware to execute the software.

Device Identifier-Specific Secret Key Generation Process

The params 222, MPK 224, and MSK 226 that have been provisioned by the setup system 100 may be stored in the secure storage 164. To perform identity-based cryptography, the trusted processor may first self-provision the DISK 228 based on a unique or substantially-unique identifier of the secure medical device 106 or a component thereof. In some embodiments, some or all of the components of the secure medical device 106 may be associated with identifiers. For example, the processor 200 (or motherboard on which the processor 200 is located) may have a serial number assigned to it, and that unique serial number may serve as a DID 220 in the identity-based encryption and decryption processes described herein.

The trusted processor 160 may self-provision the DISK 228 in response to one or more events. For example, the first time the secure medical device 106 is powered on (or the first time the secure medical device 106 is powered on after being provisioned with the params 222, MPK 224, and MSK 226), the secret key generator 162 may generate the DISK. As another example, the secret key generator 162 may generate the DISK each time the secure medical device 106 is powered on, or each time a cryptographic operation is to be performed by the cryptography subsystem 166. As a further example, the DISK may be maintained in the secure storage 164 for a predetermined or dynamically determined period of time, after which it is removed. The secret key generator 162 may re-generate the DISK the next time it is to be used by the cryptography subsystem 166 or in response to some other event.

As shown in FIG. 2, at [1] the secret key generator 162 may obtain the DID 220. The DID 220 may be an identifier provided by a particular component (e.g., the processor 200), or retrieved from a particular storage location (e.g., storage in the basic input-output system or "BIOS" of the secure medical device 106). At [2] the secret key generator 162 may obtain from the secure storage 164 the params 222, MPK 224, and MSK 226 that have been provisioned by the setup system 100. At [3] the secret key generator 162 may generate the DISK using the DID 220, params 222, MPK 224, and MSK 226.

In one specific, non-limiting embodiment, the secret key generator 162 may generate the DISK using an algorithm such as that described in ISO/IEC 18033-5: 2015, which is incorporated by reference herein. An example implementation is set forth in Table 3 below:

TABLE 3

Generation of Device Identifier-Specific Secret Key

Generate an identity element $M = H_1(DID)$, where $H_1$ is a hash function that maps identity strings to a group element, $H_1: \{0, 1\}^* \rightarrow G_1$
Generate DISK = MSK(M)

After the secret key generator 162 generates the DISK 228, the DISK 228 may be stored in the secure storage 164 at [4].

The cryptography subsystem 166 may use the DISK to perform encryption and/or decryption operations. At [5], the cryptography subsystem 166 may obtain input 230 to be encrypted or decrypted. For example, the verification system 104 may provide an encrypted nonce to the secure medical device 106 during an identification protocol, such as that shown in FIG. 3 and described in greater detail below. The nonce may have been encrypted using the MPK and the DID, and therefore may only be decrypted using the DISK that corresponds to the same DID.

At [6], the cryptography subsystem 166 may obtain the DISK 228 from the secure storage. At [7], the cryptography subsystem 166 may perform a cryptographic operation in the input 230 using the DISK 228. Returning to the example above, if the input 230 is an encrypted nonce, the cryptography subsystem 166 may decrypt the input 230 to generate decrypted output 232. At [8], the cryptography subsystem 166 may provide the output 232 outside of the trusted processor 160. For example, the output 232 may be provided to an application of the secure medical device 106 and stored in the application data 214.

Identification Protocol

Figure 3:
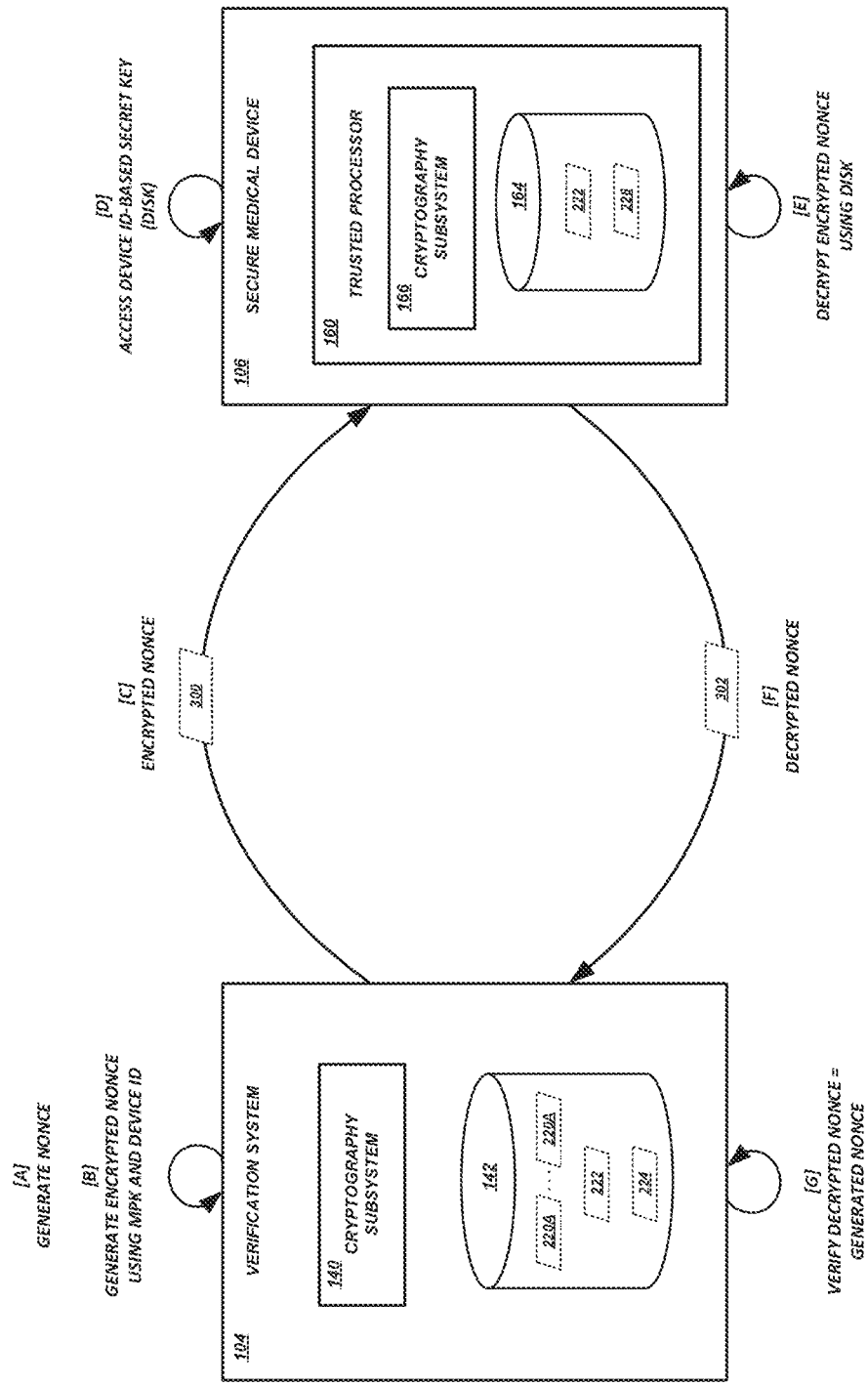
FIG. 3 is a block diagram illustrating data flows and interactions between a secure medical device and a verification system during an identity verification protocol according to some embodiments.

FIG. 3 is a block diagram of illustrative data flows and interactions during an identification protocol between a verification system 104 and a secure medical device 106. The identification protocol may be performed to verify the identity of the secure medical device 106. To do so, the verification system 104 may encrypt data using the DID of the secure medical device 106. Only if the secure medical device 106 has the DISK associated with the DID will the secure medical device 106 be able to decrypt the data and provide the unencrypted data back to the verification system 104.

At [A], the cryptography subsystem 140 or some other component of the verification system 104 can generate or otherwise obtain verification data to be used in the identification protocol. In some embodiments, the verification data may be a random data element, such as a randomly-generated nonce that is used only once. In some embodiments, the verification data may not be a nonce, but may instead be a meaningful value, such as a network address, another identifier, or the like.

At [B], the cryptography subsystem 140 can generate encrypted verification data using the verification data generated at [A], the params 222, MPK 224, and DID 220A associated with the secure medical device 106. In some embodiments, verification system 104 may have a data store 142 to store DIDs 220A-220N for each device with which the verification system 104 will perform the identification protocol. Params 222 and MPK 224 may also be stored in the data store 142. The data store 142 may be part of the cryptographic subsystem 140 or it may be a separate component or device of the verification system 104.

In one specific, non-limiting embodiment, a cryptography subsystem may encrypt data using an algorithm such as that described in ISO/IEC 18033-5: 2015, which is incorporated by reference herein. An example implementation is set forth in Table 4 below, where Msg is the input to be encrypted (e.g., the verification data or some other plain text):

TABLE 4

Encryption Using Device Identifier and Master Public Key

Define $H_1, H_2, H_3, H_4$ as cryptographic hash functions:
$H_1: \{0, 1\}^* \rightarrow G_1$, which maps an arbitrary string to an element in $G_1$.
$H_2: G_3 \rightarrow \{0, 1\}^\delta$, which maps an element in $G_1$ to a string of size $\delta$
$H_3: \{0, 1\}^\delta \times \{0, 1\}^\delta \rightarrow Z^*_p$, which maps two strings of length $\delta$ to $Z^*_p$
$H_3: \{0, 1\}^\delta \times \{0, 1\}^\delta$, which maps a string of length $\delta$ to another
Obtain an input Msg of length $\delta$
Generate a $\delta$-bit randomizer o using MPK, where "$\delta$-bit randomizer o" means o is a random string of length $\delta$ $\{0, 1\}^\delta$
Generate an identity element $M = H_1(DID)$
Generate $r = H_3(o, Msg)$
Generate $C_1 = rQ$
Generate $B = e(rM, MPK)$, where e is a bilinear pairing that maps two elements from $G_1$ and $G_2$ to $G_3$
Generate $C_2 = o \oplus H_2(B)$
Generate $C_3 = Msg \oplus H_4(o)$
Generate output = $(C_1, C_2, C_3)$ At [C], the verification system 104 can send the encrypted verification data to the secure medical device 106. For example, if the verification data is a nonce and the encrypted verification data is an encrypted nonce 300, the verification system 104 can transmit the encrypted nonce 300 to the secure medical device 106.

At [D], the cryptography subsystem 166 of the secure medical device 106 can access the DISK 228 from the secure storage 164 to decrypt the encrypted verification data. At

[E], the cryptography subsystem 166 can decrypt the encrypted verification data using the DISK 228.

In one specific, non-limiting embodiment, a cryptography subsystem may decrypt encrypted data using an algorithm such as that described in ISO/IEC 18033-5: 2015, which is incorporated by reference herein. An example implementation is set forth in Table 5 below, where CT is the input to be decrypted (e.g., the encrypted verification data or some other cypher text):

TABLE 5

Decryption Using Device Identifier-Specific Secret Key

Define $H_1, H_2, H_3, H_4$ as cryptographic hash functions:
$H_1: \{0, 1\}^* \to G_1$, which maps arbitrary string to an element in $G_1$
$H_2: G_3 \to \{0, 1\}^\delta$, which maps an element in $G_1$ to a string of size $\delta$
$H_3: \{0, 1\}^\delta \times \{0, 1\}^\delta \to Z^*_p$, which maps two strings of length $\delta$ to $Z^*_p$
$H_3: \{0, 1\}^\delta \to \{0, 1\}^\delta$, which maps a string of length $\delta$ to another
Parse CT as a tuple $\{C_1, C_2, C_3\}$
Generate $B = e(DISK, C_1)$, where e is a bilinear pairing that maps two elements from $G_1$ and $G_2$ to $G_3$
Generate $o = C_2 \oplus H_2 (B)$
Generate $Msg = C_3 \oplus H_4 (o)$
Generate $r = H_3(o, Msg)$
Determine whether $C_1 = rQ$
If yes, output Msg
If no, output "error"

At [F], the secure medical device 106 can respond to the verification system 104 by sending the decrypted verification data to the verification system 104. For example, if the encrypted verification data was an encrypted nonce 300 and the secure medical device 106 successfully decrypted the encrypted nonce 300, the secure medical device 106 may transmit the decrypted nonce 302 to the verification system 104. In some embodiments, the secure medical device 106 may include additional information in the response. For example, the secure medical device 106 may include its DID 220A or other identifying information.

At [G], the verification system 104 can verify whether the response from the secure medical device 106 satisfies one or more identification verification criteria. An identification verification criterion may be a requirement that the response include a decrypted version of the encrypted verification data that was sent to the secure medical device 106 at [C]. For example, the verification system 104 may maintain a record of the unencrypted nonce generated at [A]. The record may associate the nonce with the specific secure medical device 106 (e.g., the record may reference the DID 220A of the secure medical device 106). Upon receipt of the decrypted nonce 302 from the secure medical device 106, the verification system 104 may access the record of the unencrypted nonce associated with the DID 220A of the secure medical device 106 from which the response was received, and compare the stored nonce to the decrypted nonce 302. If the decrypted nonce 302 matches the stored nonce, then the secure medical device 106 has proven that it has the DISK that corresponds the DID 220A. The medical device 106 may be considered to have proven its identity by virtue of proving that it has the DISK that corresponds to the DID 220A. In some embodiments, alternative or additional identification verification criteria may be required to be satisfied in order to complete the identification protocol successfully. For example, a timestamp may be stored in connection with the nonce 300, indicating when it was provided to the secure medical device 106. The medical device 106 may be required to respond within predetermined or dynamically determined threshold period of time after the time represented by the timestamp.

At [H], if the response from the secure medical device 106 has satisfied the one or more identification verification criteria, then the verification system 104 may authorize the secure medical device 106 to perform a function, or the verification system 104 may initiate a function. For example, the secure medical device 106 may be authorized to connect to a network, administer medication, receive a software update, receive a drug library update, initiate an override during a medication administration operation, or the like.

Figure 4:
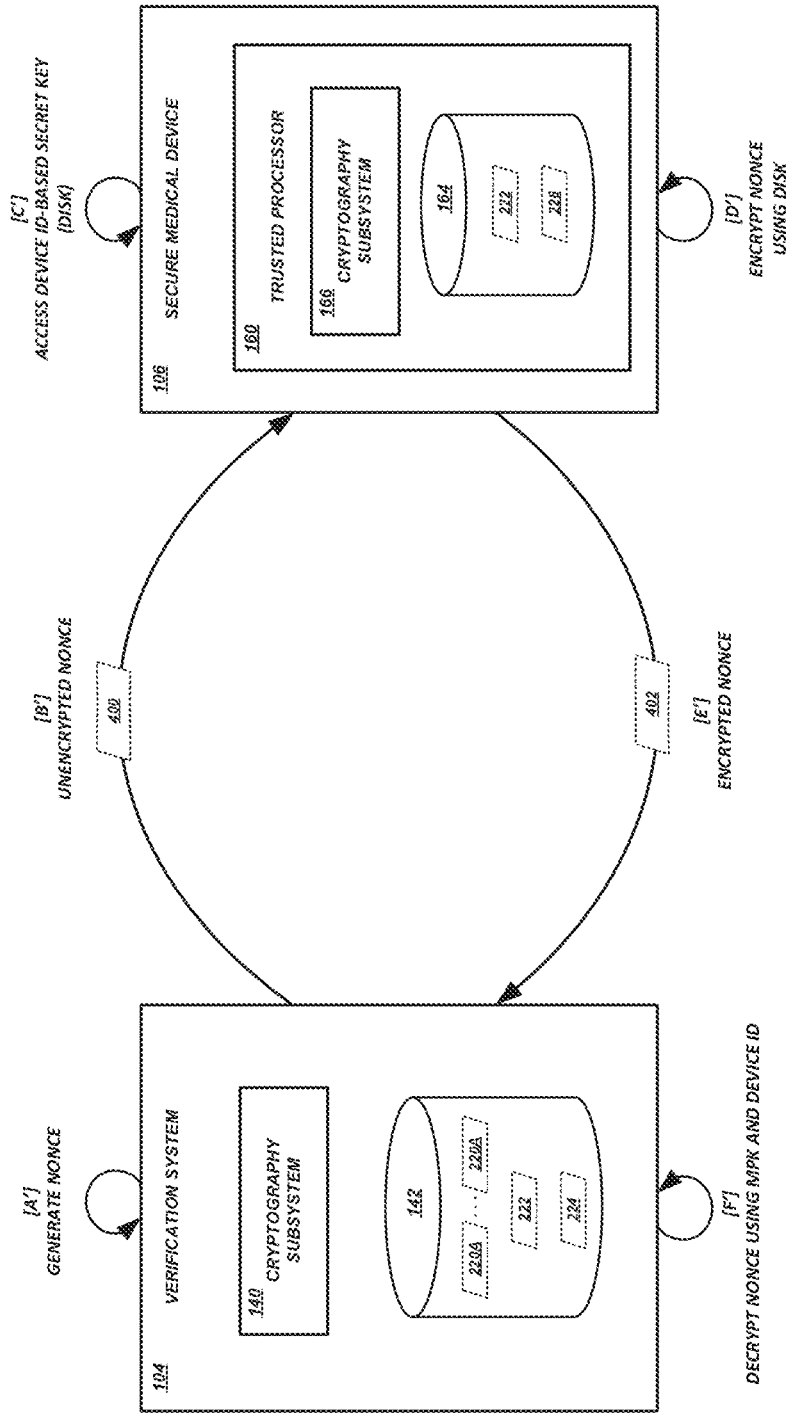
FIG. 4 is a block diagram illustrating data flows and interactions between a secure medical device and a verification system during a different identity verification protocol according to some embodiments.

In some embodiments, the verification system 104 may not encrypt the verification data prior to transmitting it to the secure medical device 106. As shown in FIG. 4, the verification system 104 may generate verification data at [A'], and transmit the unencrypted verification data (e.g., the unencrypted nonce 400) to the secure medical device at [B']. The verification system 104 does not necessarily get notified of—or otherwise determine in advance—the DID 220A of the secure medical device 106 to which the unencrypted verification data is sent. In this implementation, the secure medical device 106 may access the DISK at [C'], and encrypts the unencrypted verification data using the DISK at [D'] to generate encrypted verification data. The secure medical device 106 may transit a response to the verification system 104 at [E']. The response includes the encrypted (signed) verification data, such as an encrypted nonce 402. In some embodiments, the response may also include the unencrypted verification data and/or the DID of the secure medical device 106. The verification system 104 decrypts the encrypted verification using the DID (either known in advance or provided by the secure medical device 106) and the MPK at [F']. At [G'] the verification system 104 determines whether the response satisfies one or more identification verification criteria (e.g., the decrypted verification data matches the unencrypted verification data, either stored previously or included in the response from the secure medical device 106). At [H'], if the response has satisfied the one or more identification verification criteria, then the verification system 104 may authorize the secure medical device 106 to perform a function, or the verification system 104 may initiate a function.

Identity-Based Medication Administration Authorization Process

Identity-based cryptography may be used to control which devices are able to perform operations using particular objects. In a health care setting, the devices may be secure medical devices 106, such as infusion pumps as described above. The objects may be medication containers, such as vials or intravenous ("IV") fluid bags containing medical fluid that may be administered to patients using the secure medical devices. When a medication container is prepared for use, control information may be generated that assigns the medication container to a particular secure medical device 106 (or subset of secure medical devices 106). Advantageously, the control information may be encrypted using a DID of a medical device 106 to which the medication container is assigned. Only the medical device 106 with the DISK that corresponds to the DID will be able to decrypt the control information and administer the medication in the medication container. Thus, medication containers can be assigned to particular medication devices and only used by those secure medical devices 106; secure medical devices 106 may be prevented from using medication containers other than those to which they have been assigned.

Figure 5:
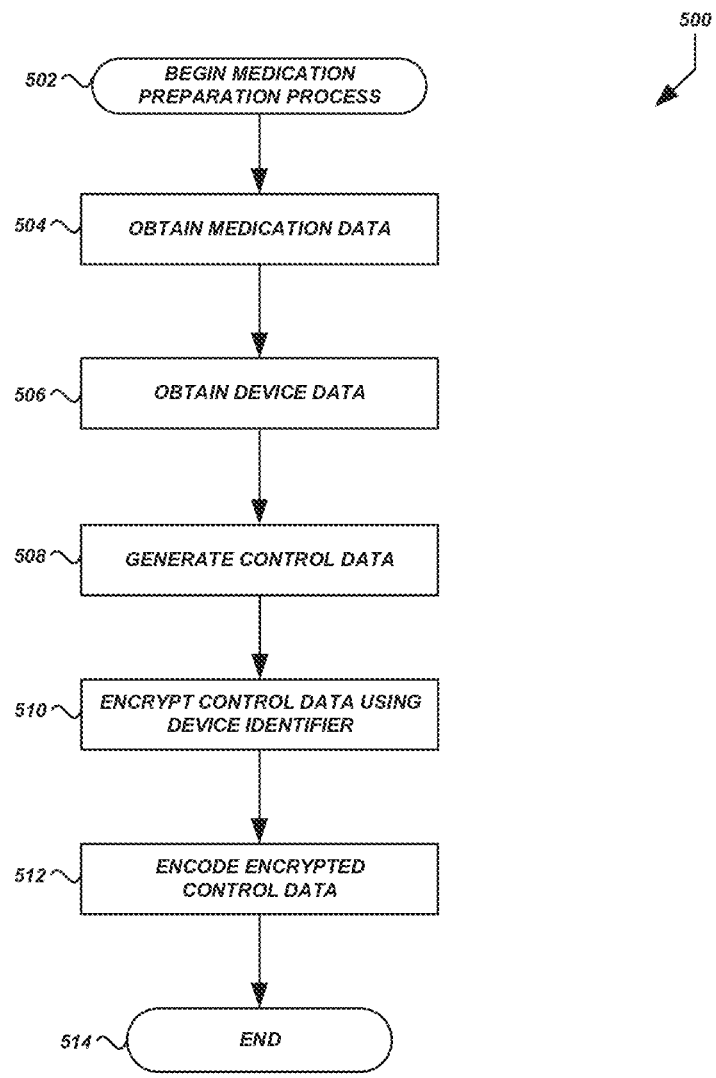
FIG. 5 is a flow diagram of an illustrative routine for secure medication preparation according to some embodiments.
Figure 6:
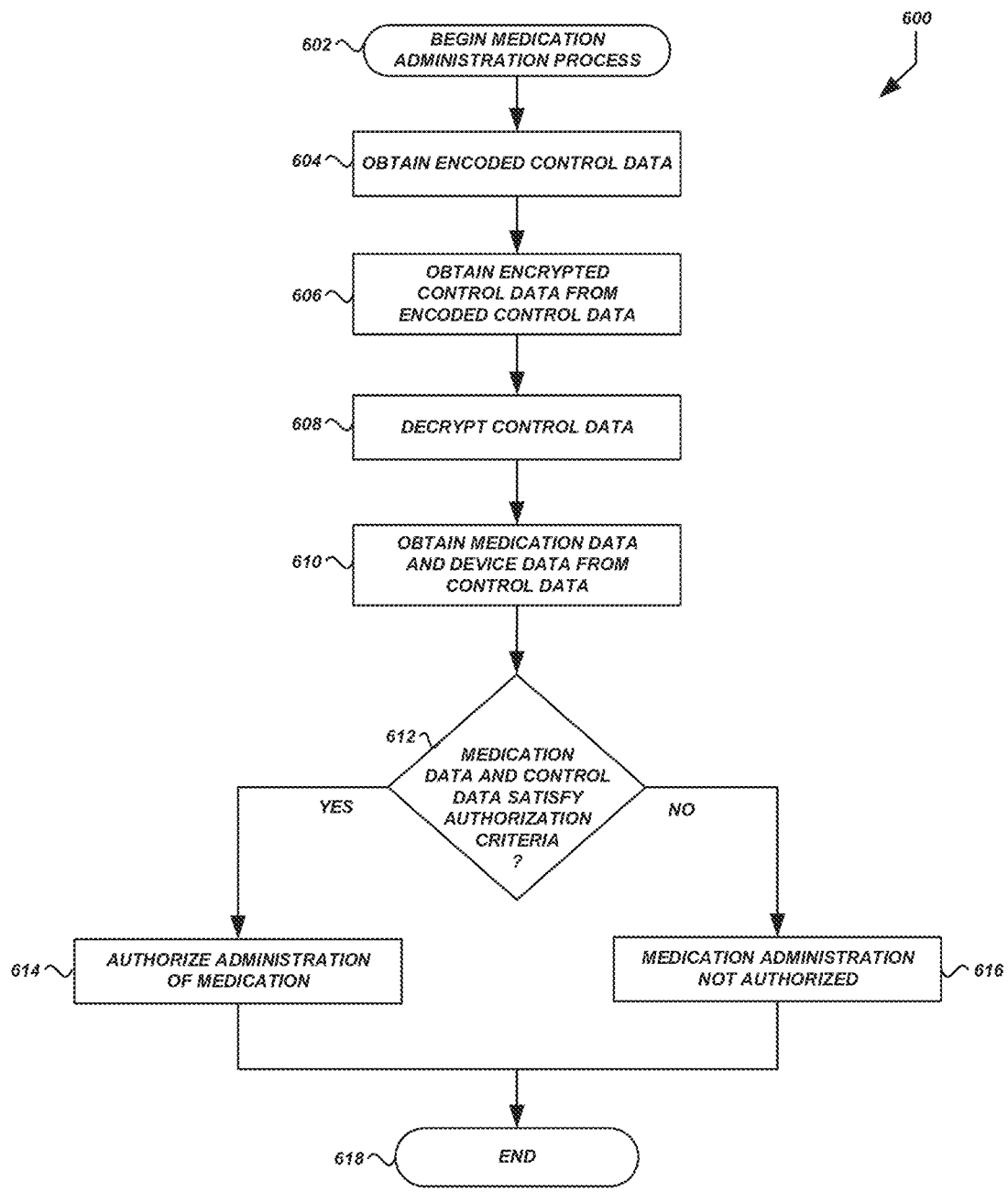
FIG. 6 is a flow diagram of an illustrative routine for secure medication administration according to some embodiments.
Figure 7:
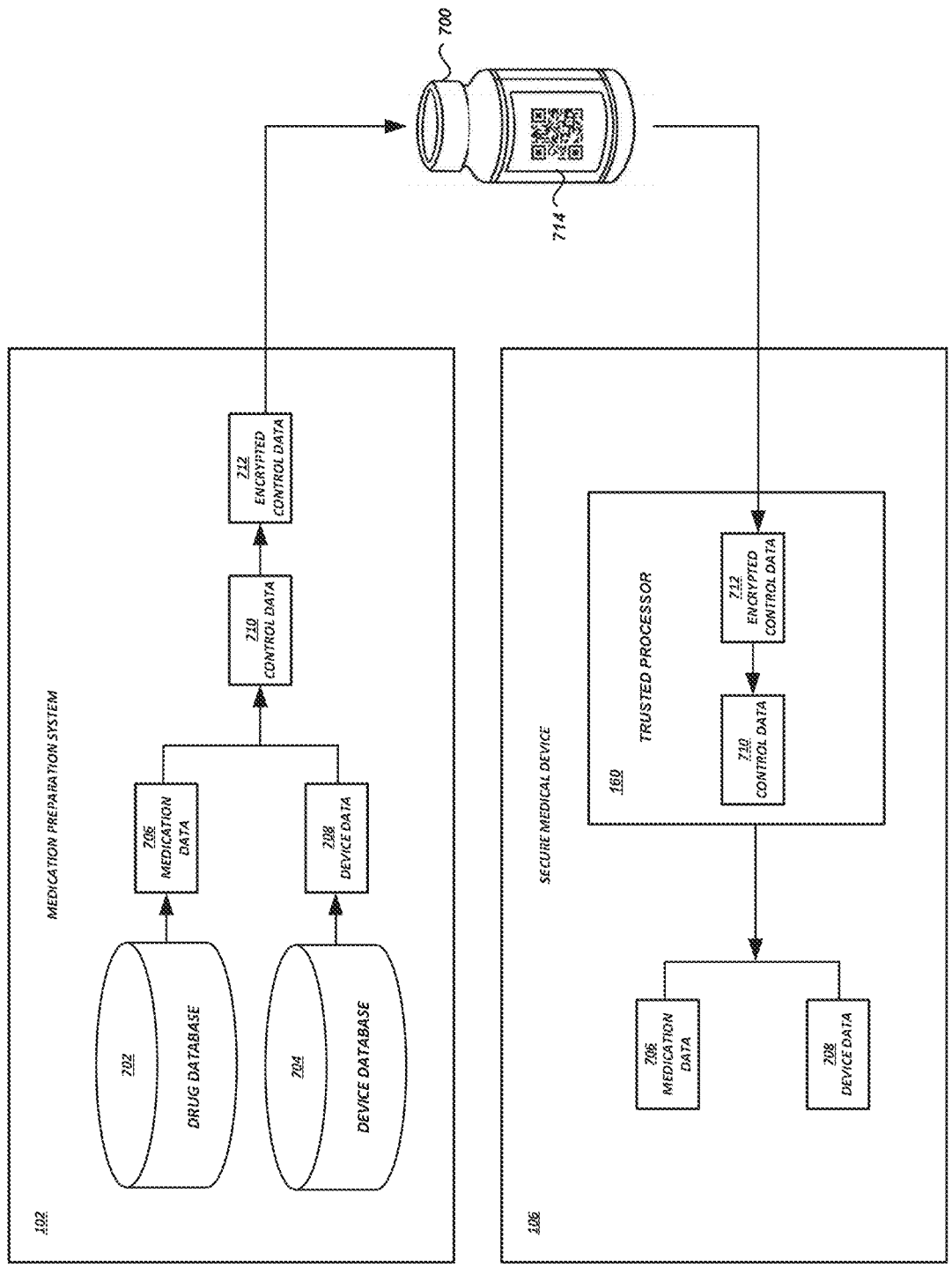
FIG. 7 is a block diagram illustrating data flows and processing performed during secure medication preparation and administration according to some embodiments.

FIGS. 5 and 6 are flow diagrams of illustrative routines performed by the medication preparation system 102 and secure medical device 106, respectively, during an identity-based medication administration authorization process. The routines 500 and 600 of FIGS. 5 and 6 will be described with further reference to FIG. 7, which is a block diagram illustrating the generation of control information by a medication preparation system 102 to assign a medication container 700 to a particular secure medical device 106.

The routine 500 shown in FIG. 5 begins at block 502. The routine 500 may begin in response to an event, such as when a pharmacist or medication preparation technician accesses a software application of the medication preparation system 102 to initiate preparation of a medication container for administration by a particular secure medical device 106. When the routine 500 is initiated, a set of executable program instructions stored on one or more non-transitory computer-readable media (e.g., hard drive, flash memory, removable media, etc.) may be loaded into memory (e.g., random access memory or "RAM") of the medication preparation system 102. The executable instructions may be executed by a hardware-based computer processor (e.g., a central processing unit or "CPU") of the medication preparation system 102. In some embodiments, the routine 500 or portions thereof may be implemented on multiple processors, serially or in parallel.

At block 504, the medication preparation system 102 may obtain medication data 706 regarding the medication that is in (or is being compounded into) the medication container 700. The medication data 706 may include an identifier of the medication, a name of the medication, dosing information, other data, or some combination thereof. In some embodiments, the medication data 706 may be obtained from a drug database 702 of the medication preparation system 102.

At block 506, the medication preparation system 102 may obtain device data 708 regarding the secure medical device 106 to which the medication container is being assigned. The device data 708 may include the DID and/or other data regarding the secure medical device 106. In some embodiments, the device data 708 may be obtained from a device database 704 of the medication preparation system 102.

At block 508, the medication preparation system 102 generate control data 710 using the medication data 706 and device data 708. The control data 710 may be a data structure comprising a data element for the medication data 706 and a data element for the device data 708. In some embodiments, the device data 708 may be concatenated to the medication data 706 to generate the control data 710. For example, the first m bytes of control data 710 may be reserved for the medication data 706, and the next n bytes may be reserved for device data 708 (or vice versa). As another example, the portion of control data 710 preceding a particular character or value may be medication data 706, and next portion of control data 710 may be device data 708 (or vice versa). In some embodiments, the control data 710 may also include other data, such as patient data (e.g., an identifier of the patient to whom the medication is prescribed), unit data (e.g., an identifier of the unit of the health care facility in which the medication may be administered), etc. The additional data may be included in the control data 710 at other locations in the same manner as the medication data 706 and device data 708. The example structures of control data 710 described herein are illustrative only, and are not meant to be limiting. In some embodiments, other configurations of control data 710 may be used. In some embodiments, the control data 710 may not include both medication data 706 and device data 708, but may instead include medication data 706 or device data 708 (and, optionally, other data such as patient data).

At block 510, the cryptography subsystem 120 of the medication preparation system 102 may generate encrypted control data 712 by encrypting the control data 710 using the DID of the secure medical device 106 to which the medication container 700 is assigned. In some embodiments, the encryption operation may be performed using the encryption algorithm set forth above.

At block 512, the cryptography subsystem 120 or some other component of the medication preparation system 102 may encode the encrypted control data 712 into a form that may be represented by a control item 714. The control item 714 may be coupled to or integrated with the medication container 700, and may include the encoded control data. For example, the control item 714 may be a label and the encoded control data may be a barcode or quick response ("QR") code. In this case, the medication preparation system 102 may encode the encrypted control data 712 into a barcode or QR code, and the encoded control data may be printed onto the label such that it may be scanned by the secure medical device 106 to recover the encrypted control data 712. in some embodiments, the control item may be an electronic data store accessible via wired or wireless communication. For example, the control item may be a radio frequency identification ("RFID") tag or a microchip. The encrypted control data may be encoded into a form that is stored by control item and accessible from the control item by the secure medical device 106. The process 500 may terminate at block 514.

Once the control item 714 has been provisioned with encoded control data and affixed to the medication container 700 (if necessary), the medication container 700 may be delivered for use by the secure medical device 106. The secure medical device 106 may then perform a routine, such as routine 600 shown in FIG. 6, to read and process the control data and determine whether to proceed with administration of the medication within the medication container 700.

The routine 600 begins at block 602. The routine 600 may begin in response to an event, such as when a health care provider accesses a software application of the secure medical device 106 to initiate administration of medication from the medication container 700. When the routine 600 is initiated, a set of executable program instructions stored on one or more non-transitory computer-readable media (e.g., hard drive, flash memory, removable media, etc.) may be loaded into memory (e.g., random access memory or "RAM") of the secure medical device 106. The executable instructions may be executed by one or more hardware-based computer processors of the secure medical device 106, such as the processor 200 and trusted processor 160.

At block 604, the secure medical device 106 may obtain the encoded control data from the control item 714 of the medication container 700. If the control item 714 is a label with a barcode or QR code, a scanning device may be used to read the encoded control data and provide it—in encoded or decoded form—to the secure medical device 106. Other types of control items may be accessed depending upon the implementation (e.g., an RFID tag may be read by an RFID reader, a microchip may be read by a chip reader, etc.).

At block 606, the secure medical device 106 may obtain the encrypted control data 712 from the encoded control data, if the encoded control data is read from the control item 714 without being automatically decoded as part of the reading process. For example, a barcode may be automatically decoded when read by a barcode reader such that decoded data represented by the barcode (encrypted control data 712 in this example) is output by the barcode reader to other components of the secure medical device 106. If such decoding is not performed automatically, the secure medical device 106 may be configured (e.g., via application instructions 212) to perform the necessary decoding to recover the encrypted control data 712 represented by the encoded control data read from the control item 714.

At block 608, the trusted processor 160 of the secure medical device 106 may generate decrypted control data 710 from the encrypted control data 712. The cryptography subsystem 166 may obtain the DISK 228 from the secure storage 164, and use the DISK 228 to decrypt the encrypted control data 712. In some embodiments, the decryption operation may be performed using the algorithm set forth above.

At block 610, the secure medical device 106 may obtain medication data 706 and device data 708 from the decrypted control data 710. The secure medical device 106 may be configured (e.g., via application instructions 212) to parse the medication data 706 and device data 708 from the control data 710. For example, the first m bytes of decrypted control data 710 may be reserved for the medication data 706, and the next n bytes may be reserved for device data 708 (or vice versa). As another example, the portion of control data 710 preceding a particular character or value may be medication data 706, and next portion of control data may be device data 708 (or vice versa). In some embodiments, as described above, the control data 710 may also include other data, such as patient data (e.g., an identifier of the patient to whom the medication is prescribed), unit data (e.g., an identifier of the unit of the health care facility in which the medication may be administrated), etc. The additional data may be included in the control data 710 at other locations in the same manner as the medication data 706 and device data 708. The example structures of control data 710 described herein are illustrative only, and are not meant to be limiting. In some embodiments, other configurations of control data 710 may be used. In some embodiments, the control data 710 may not include both medication data 706 and device data 708, but may instead include medication data 706 or device data 708 (and, optionally, other data such as patient data).

At decision block 612, the secure medical device 106 may determine whether the medication data 706 and device data 708 satisfy one or more authorization criteria to authorize administration of the medication. The one or more authorization criterion may include: successfully decrypting the encrypted control data and obtaining the control data therefrom; determining that a DID from the device data 708 matches the DID 220 of the current secure medical device 106; determining that a medication ID from the medication data 706 matches a medication in a drug library 210 of the secure medical device 106; determining that the medication represented by the medication data 706 is permitted to be administered by the secure medical device 106; determining that a patient ID from patient data matches a particular patient ID (e.g., a patent ID of a patient whose admittance bracelet or other medical identification has been scanned or entered); other authorization criteria; or any combination thereof. If the one or more authorization criteria have been satisfied, the routine 600 may proceed to block 614, wherein the medication administration operation is authorized and proceeds. Otherwise, if an authorization criterion has not been satisfied, the routine 600 may proceed to block 616 where an unauthorized state is entered. The process 600 may terminate at block 618.

Logging and Backup Verification

Figure 8:
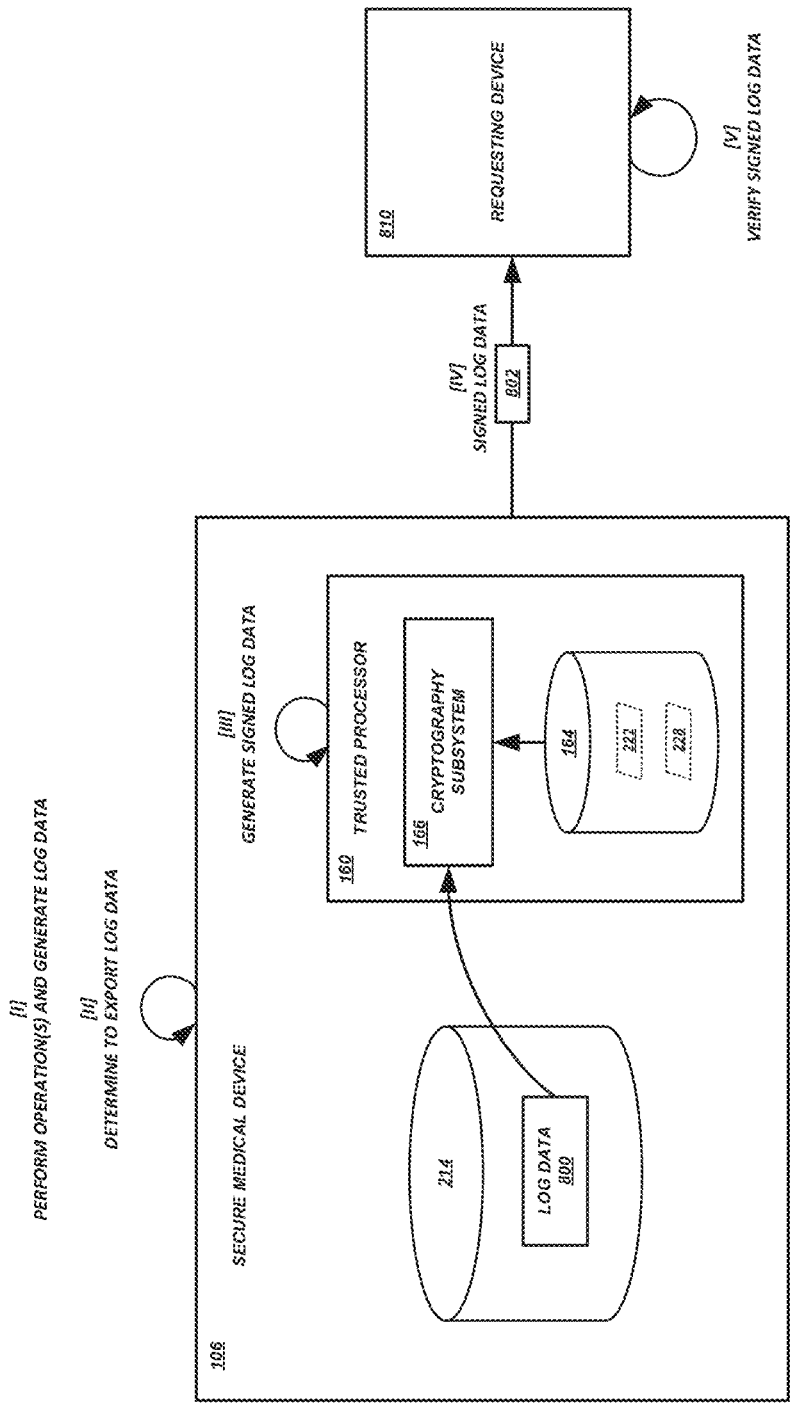
FIG. 8 is a block diagram illustrating data flows and processing performed to securely manage logs and backup files according to some embodiments.

FIG. 8 is a block diagram of illustrative data flows and operations during log file generation, export, and consumption. During operation, a secure medical device 106 may generate log data regarding the functions that the secure medical device 106 performs. For example, the secure medical device 106 may generate one or more records regarding a medication administration process, such as the medication administration process described above. Such records may be stored in a log file. Under certain circumstances, a forensic analysis of the log file may be performed, such as when an issue with a particular medication administration process occurs. In order to ensure that the logged record of the process is an authentic, accurate record of the operations performed by the secure medical device 106, the log file data may be signed using the DISK before being exported by—or otherwise provided outside of—the secure medical device 106. Advantageously, the signing of log data using the DISK facilitates verification, by a third party, of the authenticity of the source of the log data and the integrity of the data within the log.

At [I], the secure medical device 106 performs various operations and generates log data 800 regarding the operations. The log data 800 may be stored within the secure medical device 106, such as the application data 214 area of memory, in a persistent data store, or the like.

At [II], the secure medical device 106 may determine that log data 800 is to be exported. In some embodiments, the secure medical device 106 may receive a request or a command to export the log data. In some embodiments, the secure medical device 106 may export the log data 800 on a predetermined or dynamically determined schedule, or in response to some other event. The log data 800 to be exported may be all log data currently stored in the secure medical device 106, the log data that has been added since the last export, or a subset of log data associated with the current export process (e.g., log data satisfying a filter or other criteria specified in the request or export configuration).

At [III], the cryptography subsystem 166 may obtain the DISK 228 from the secure data store 164 and sign the log data 800 to be exported. To sign the log data 800, the cryptography subsystem 166 may encrypt the log data 800 using the DISK 228. The signed data 802 may also include an unencrypted version of the log data 800. Thus, a recipient of the signed log data 802 can decrypt the encrypted version using the MPK and the DID associated with the secure medical device 106, and determine whether the decrypted log data matches the unencrypted log data. If so, the unencrypted log data is considered to be authentic.

At [IV], the secure medical device 106 can export the signed log data 802 to a third-party device or system. For example, as shown, the signed log data 802 may be exported to a requesting device 810. In some embodiments, the signed log data 802 may be exported to an intermediary data store, where it is stored and accessible to third party devices or systems.

At [V], the requesting device 810 (or some other third-party deice or system) can decrypt the signed data 802 using the MPK and the DID associated with the secure medical device 106. The requesting device 810 may then compare the decrypted signed data to the unencrypted log data. If the two data sets match, then the requesting device 810 can be assured that the log data did originate from the secure medical device 106 and has not been tampered with.

In some embodiments, data other than log data may be signed by the secure medical device 106 before being exported. For example, the secure medical device 106 may generate a backup of its configuration settings, such as data regarding networks and devices with which the secure medical device 106 is to interact. In order to ensure the authenticity of the configuration data and that it has not been tampered with, the secure medical device 106 may sign the backup file before exporting the backup file for storage. Subsequently, when the secure medical device 106 is to restore a backup file, the secure medical device 106 can decrypt the signed data using its own DID and the MPK. If the decrypted data matches the unencrypted data, then the backup file is considered to be authentic and not tampered with.

Initial Communication and Configuration

Figure 9:
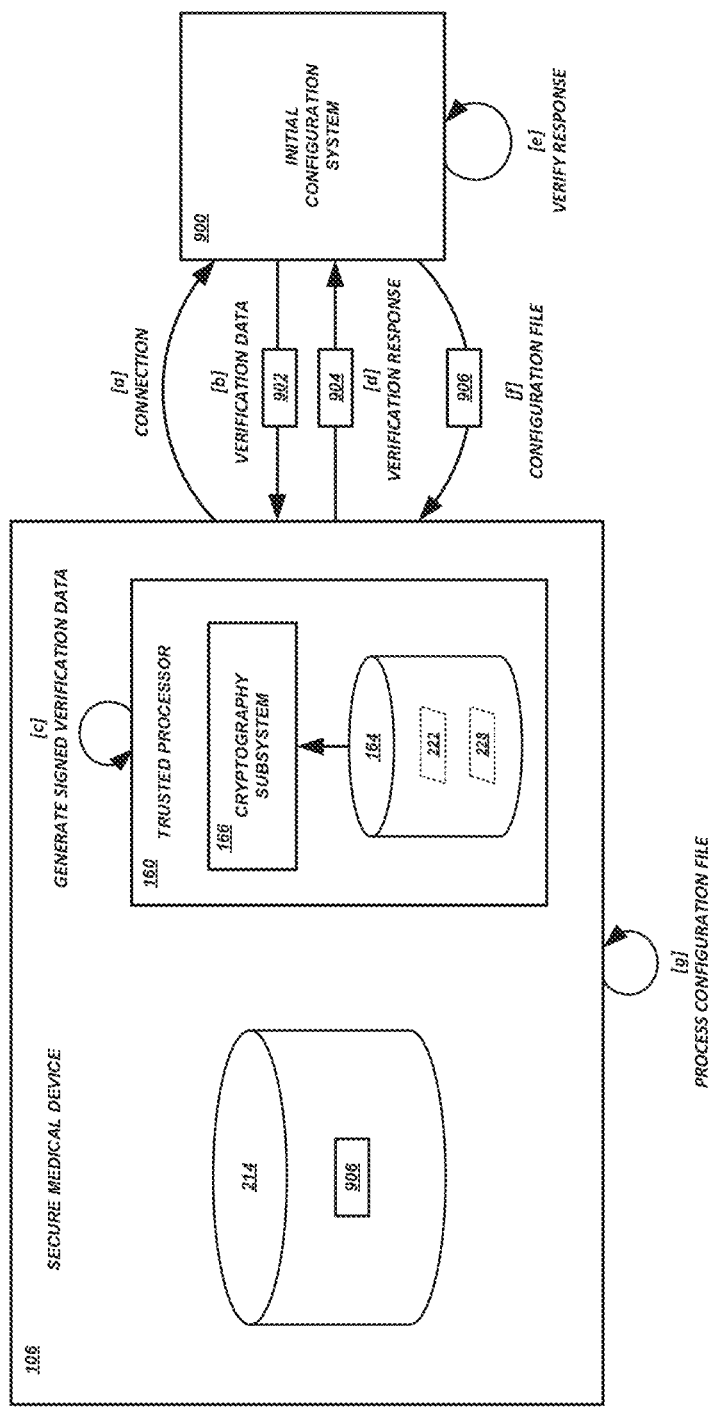
FIG. 9 is a block diagram illustrating data flows and processing performed to securely configure a secure medical device according to some embodiments.

FIG. 9 is a block diagram of illustrative data flows and operations during an initial communication and configuration of the secure medical device 106. The secure medical device 106 may be configured to, upon initial startup after deployment, connect by default to an initial configuration system and obtain a configuration file. The configuration file may include various configuration information to be used by the medical device 106, such as network connectivity information. In this way, the medical device can be automatically configured in a secure, verified manner.

At [a], the secure medical device 106 connects to the initial configuration system 900. The initial configuration system 900 may include a verification system 104 or vice versa. In some embodiments, the initial configuration system 900 may be a separate device or system from the verification system 104. The initial configuration system may provide a network connection—such as a Wi-Fi connection—for secure medical devices to connect to for configuration data.

At [b], the initial configuration system 900 responds by initiating an identity verification protocol, such as a one of the protocols described above. For example, the initial configuration system 900 may generate verification data such as a random nonce 902, and send the nonce to the secure medical device 106. The secure medical device 106 may sign the nonce 902 using the DISK 228 at [c], and respond to the initial configuration system 900 by sending back the signed nonce 904 at [d]. In some embodiments, the response may include additional data, such as the DID of the secure medical device 106.

The initial configuration system 900 may decrypt the signed response using the DID and the MPK. If the signed response satisfies one or more identification criteria at [e], the initial configuration system 900 may determine that secure medical device 106 has successfully proven its identity. In response, the initial configuration system 900 may provide a configuration file 906 to the secure medical device 106 at [f]. The secure medical device 106 may process the configuration file 906 at [g]. For example, the secure medical device 106 may read configuration settings (e.g., a network address of a system to which the medical device 106 is to connect with) from the configuration file 906 and the settings during operation.

Other Considerations

It is to be understood that not necessarily all objects or advantages may be achieved in accordance with any particular embodiment described herein. Thus, for example, those skilled in the art will recognize that certain embodiments may be configured to operate in a manner that achieves or optimizes one advantage or group of advantages as taught herein without necessarily achieving other objects or advantages as may be taught or suggested herein.

Many other variations than those described herein will be apparent from this disclosure. For example, depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together.

The various illustrative logical blocks, modules, and algorithm elements described in connection with the embodiments disclosed herein can be implemented as electronic hardware, computer software, or combinations of both. To clearly illustrate this interchangeability of hardware and software, various illustrative components, blocks, modules, and elements have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a computer processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A computer processor can be a microprocessor, but in the alternative, the processor can be a controller, microcontroller, or state machine, combinations of the same, or the like. A processor can include electrical circuitry configured to process computer-executable instructions. In another embodiment, a processor includes an FPGA or other programmable device that performs logic operations without processing computer-executable instructions. A processor can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor may also include primarily analog components. For example, some or all of the signal processing algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, or algorithm described in connection with the embodiments disclosed herein can be embodied directly in hardware, in a software module stored in one or more memory devices and executed by one or more processors, or in a combination of the two. A software module can reside in RAM memory, flash memory, ROM memory, EPROM memory, EEPROM memory, registers, hard disk, a removable disk, a CD ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile. The processor and the storage medium can reside in an ASIC. The ASIC can reside in a user terminal. In the alternative, the processor and the storage medium can reside as discrete components in a user terminal.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements, and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Unless otherwise explicitly stated, articles such as "a", "an", or "the" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B, and C" can include a first processor configured to carry out recitation A working in conjunction with a second processor configured to carry out recitations B and C.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments described herein can be implemented within a form that does not provide all of the features and benefits set forth herein, as some features can be used or practiced separately from others. All such modifications and variations are intended to be included herein within the scope of this disclosure. Further, additional embodiments created by combining any two or more features or techniques of one or more embodiments described herein are also intended to be included herein within the scope of this disclosure.

What is claimed is:

1. A system comprising:
a plurality of medical devices, wherein a medical device of the plurality of medical devices comprises:
an input device configured to:
read encoded control data from a medication container; and
decode the encoded control data to obtain encrypted control data;
a trusted processor comprising:
a secure data store storing a master secret key and a master public key;
a secret key generator configured to self-provision a device identifier-specific secret key, wherein to self-provision the device identifier-specific secret key, the secret key generator is configured to:
generate the device identifier-specific secret key using the master secret key and an identifier uniquely associated with the medical device; and
store the device identifier-specific secret key in the secure data store; and
a cryptography subsystem configured to:
receive the encrypted control data; and
generate decrypted control data using the encrypted control data and the device identifier-specific secret key, wherein the decrypted control data comprises a control device identifier;
wherein the trusted processor is configured to prohibit output, from the trusted processor, of the device identifier-specific secret key and the master secret key; and
a motor configured to cause fluid to be administered from the medication container, wherein the motor is permitted to be activated based at least partly on the control device identifier matching the identifier uniquely associated with the medical device; and
a setup system comprising computer-readable memory and one or more computer processors, wherein the setup system is configured to:
generate the master secret key and the master public key; and
provision the master secret key and the master public key to the trusted processor of each of the plurality of medical devices.

2. The system of claim 1, further comprising a verification system comprising computer-readable memory and one or more computer processors, wherein the verification system is configured to:
generate a random nonce;
encrypt the random nonce to generate an encrypted nonce based at least partly on the master public key and an identifier of the medical device;
send the encrypted nonce to the medical device;
receive a response from the medical device; and
determine whether the response satisfies one or more identification verification criteria.

3. The system of claim 1, further comprising a verification system comprising computer-readable memory and one or more computer processors, wherein the verification system is configured to:
generate a random nonce;
send the random nonce to the medical device;
receive a response from the medical device, wherein the response comprises encrypted data;
decrypt the encrypted data using the master public key and an identifier of the medical device; and determine whether the response satisfies one or more identification verification criteria.

4. The system of claim 1, further comprising an initial configuration system comprising computer-readable memory and one or more computer processors, wherein the initial configuration system is configured to:
  execute an identification verification protocol with the medical device based at least partly on the master public key and an identifier of the medical device; and
  in response to successful completion of the identification verification protocol, send a configuration file to the medical device.

5. The system of claim 1, further comprising a medication preparation system comprising computer-readable memory and one or more computer processors, wherein the one or more computer processors are configured to:
  generate control data comprising:
    a device identifier associated with the medical device; and
    a medication identifier associated with a medication container;
  generate encrypted control data using the control data, the master public key, and the device identifier; and
  generate an encoded label for the medication container using the encrypted control data.

6. The system of claim 1, wherein the medical device is further configured to:
  generate log data;
  sign the log data using the cryptography subsystem to generate signed log data; and
  export the signed log data to a third-party device.

7. The system of claim 1, wherein the medical device is further configured to:
  generate a configuration backup file;
  sign the configuration backup file using the cryptography subsystem to generate a signed configuration backup file; and
  export the signed configuration backup file.

8. A system comprising:
  an infusion pump comprising:
    an input device configured to:
      read encoded control data from a medication container; and
      decode the encoded control data to obtain encrypted control data;
    a trusted processor comprising:
      a secure data store storing a master secret key;
      a secret key generator configured to self-provision an identifier-specific secret key associated with an identifier of the infusion pump, wherein to self-provision the identifier-specific secret key, the secret key generator is configured to:
        generate the identifier-specific secret key using the master secret key and the identifier of the infusion pump; and
        store the identifier-specific secret key in the secure data store such that the identifier-specific secret key is not accessible outside the trusted processor; and
      a cryptography subsystem configured to:
        receive the encrypted control data; and
        decrypt the encrypted control data using the identifier-specific secret key to generate decrypted control data comprising a control device identifier; and
    a motor configured to cause fluid to be administered from the medication container, wherein the motor is permitted to be activated based at least partly on the control device identifier matching the identifier of the infusion pump; and
  a setup system comprising computer-readable memory and one or more computer processors, wherein the setup system is configured to:
    generate the master secret key and a master public key; and
    provision the master secret key and the master public key to the trusted processor.

9. The system of claim 8, the infusion pump further comprising a network interface configured to receive a nonce from a verification system,
  wherein the cryptography subsystem is further configured to encrypt the nonce using the identifier-specific secret key to generate an encrypted nonce, and
  wherein the network interface is further configured to send the encrypted nonce to the verification system.

10. The system of claim 8, the infusion pump further comprising a network interface configured to receive an encrypted nonce from a verification system,
  wherein the cryptography subsystem is further configured to decrypt the encrypted nonce using the identifier-specific secret key to generate a decrypted nonce, and
  wherein the network interface is further configured to send the decrypted nonce to the verification system.

11. The system of claim 8, the infusion pump further comprising a network interface configured to:
  execute an identification verification protocol with an initial configuration system based at least partly on the identifier-specific secret key; and
  in response to successful completion of the identification verification protocol, receive a configuration file from a verification system.

12. The system of claim 8, the infusion pump further configured to:
  generate log data;
  sign the log data using the cryptography subsystem to generate signed log data; and
  export the signed log data to a third-party device.

13. The system of claim 8, the infusion pump further configured to:
  generate a configuration backup file;
  sign the configuration backup file using the cryptography subsystem to generate a signed configuration backup file; and
  export the signed configuration backup file.

* * * * *